United States Patent
Adler et al.

(10) Patent No.: US 9,198,900 B2
(45) Date of Patent: Dec. 1, 2015

(54) TREATMENT OF PERITONEAL INJURY USING JAK INHIBITORS

(71) Applicant: Los Angeles Biomedical Research Institute at Harbor-UCLA Medical Center, Torrance, CA (US)

(72) Inventors: Sharon Adler, Los Angeles, CA (US); Bancha Satirapoj, Bangkok (TH); Ying Wang, Torrance, CA (US); Cynthia C. Nast, Rancho Palos Verdes, CA (US); Tiane Dai, Torrance, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 0 days.

(21) Appl. No.: 13/829,163

(22) Filed: Mar. 14, 2013

(65) Prior Publication Data
US 2013/0303563 A1 Nov. 14, 2013

Related U.S. Application Data

(63) Continuation-in-part of application No. 13/665,283, filed on Oct. 31, 2012, now abandoned.

(60) Provisional application No. 61/558,292, filed on Nov. 10, 2011.

(51) Int. Cl.
*A61K 31/437* (2006.01)

(52) U.S. Cl.
CPC .................... *A61K 31/437* (2013.01)

(58) Field of Classification Search
None
See application file for complete search history.

(56) References Cited

U.S. PATENT DOCUMENTS

| | | | |
|---|---|---|---|
| 7,087,727 | B2 | 8/2006 | Chen et al. |
| 8,592,223 | B2 | 11/2013 | Adler et al. |
| 2005/0266437 | A1 | 12/2005 | Veiby |
| 2010/0221752 | A2 | 9/2010 | Gold et al. |
| 2010/0266531 | A1 | 10/2010 | Hsieh et al. |
| 2011/0067123 | A1 | 3/2011 | Andersen et al. |
| 2011/0177613 | A1 | 7/2011 | Adler et al. |
| 2012/0266260 | A1 | 10/2012 | Suzuki et al. |
| 2012/0295361 | A1 | 11/2012 | Cerda et al. |
| 2012/0329886 | A1 | 12/2012 | Adler et al. |
| 2014/0135227 | A1 | 5/2014 | Adler et al. |

FOREIGN PATENT DOCUMENTS

WO    WO 01/57062    8/2001

OTHER PUBLICATIONS

Schilte et al., Factors contributing to peritoneal tissue remodeling in peritoneal dialysis, Peritoneal Dialysis International, vol. 29, pp. 605-617, 2009.*
Wang et al., Inhibition of the JAK/STAT signaling pathway prevents the high glucose-induced increase in TGF-beta and fibronectin synthesis in mesangial cells. Diabetes 2002;51 (12): 3505-9.*
Marrero et al., Role of the JAK/STAT signaling pathway in diabetic nephropathy. Am J Physiol Renal Physiol 2006; 290(4):F762-F768.*
U.S. Appl. No. 13/665,283, filed Oct. 31, 2012, Adler et al.
US Office Action dated Jan. 27, 2012 issued in U.S. Appl. No. 12/924,608.
US Office Action dated Feb. 13, 2013 issued in U.S. Appl. No. 13/571,211.
US Notice of Allowance dated Jul. 12, 2013 issued in U.S. Appl. No. 13/571,211.
US Office Action dated Feb. 25, 2014 issued in U.S. Appl. No. 14/058,099.
Aguilera et al. (2005) "Effects of rapamycin on the epithelial-to-mesenchymal transition of human peritoneal mesothelial cells." *Int J Artif Organs* 28: 164-9.
Amiri et al. (2002) "Angiotensin II activation of the JAK/STAT pathway in mesangial cells is altered by high glucose." *Kidney International* 61:1605-16.
Aroeira et al. (2005) "Mesenchymal Conversion of Mesothelial Cells as a Mechanism Responsible for High Solute Transport Rate in Peritoneal Dialysis: Role of Vascular Endothelial Growth Factor." *American Journal of Kidney Diseases* 46: 938-948.
Aroeira et al. (2007) "Epithelial to mesenchymal transition and peritoneal membrane failure in peritoneal dialysis patients: pathologic significance and potential therapeutic interventions." *Journal of the American Society of Nephrology: JASN* 18: 2004-13.
Beelen et al. (2005) "Omental milky spots in peritoneal pathophysiology (spots before your eyes)." *Peritoneal Dialysis International: Journal of the International Society for Peritoneal Dialysis* 25(1): 30-2.
Breborowicz et al. (2001) "Hyaluronan modifies inflammatory response and peritoneal permeability during peritonitis in rats." *American Journal of Kidney Diseases* 37: 594-600.
Breborowicz et al. (2004) "N-Acetylglucosamine—an osmotic slute for peritoneal dialysis without inducing hyperinsulinemia." *Blood Purif* 22: 183-7.

(Continued)

*Primary Examiner* — Svetlana M Ivanova
(74) *Attorney, Agent, or Firm* — Emily Haliday

(57) ABSTRACT

The invention provides, in certain embodiments, a method of preventing and/or treating peritoneal injury and/or diminished function by administering an effective amount of one or more inhibitors of JAK. The invention also provides a pharmaceutical composition including a JAK inhibitor for the treatment of peritoneal injury and/or diminished function. In another aspect, the invention provides a method of detecting an indicator of peritoneal injury. The method entails assaying a biological sample for periostin, wherein the presence of periostin at an elevated level indicates the presence and/or degree of peritoneal injury. Also provided, are methods of identifying subject for treatment of peritoneal injury and/or diminished function, methods of determining progression of these conditions, as well as methods of determining subjects' response to treatment.

23 Claims, 29 Drawing Sheets
(17 of 29 Drawing Sheet(s) Filed in Color)

(56) References Cited

OTHER PUBLICATIONS

Breborowicz et al. (2006) "N-acetylglucosamine reduces inflammatory response during acute peritonitis in uremic rats." *Blood Purif* 24: 274-81.

Brulez et al. (1995) "First-line defense mechanisms in the peritoneal cavity during peritoneal dialysis." *Peritoneal Dialysis International: Journal of the International Society for Peritoneal Dialysis* 15(7) Suppl:S24-33; discussion S33-4; 11 Pages.

Butcher et al. (2007) "Periostin promotes atrioventricular mesenchyme matrix invasion and remodeling mediated by integrin signaling through Rho/PI 3-kinase." *Dev Biol* 302(1):256-66. doi:10.1016/j.ydbio.2006.09.048, NIH Public Access Author Manuscript, 23 Pages.

Castronovo et al. (2006) "A chemical proteomics approach for the identification of accessible antigens expressed in human kidney cancer" *Molecular & Cellular Proteomics* 2083-2091.

Cavallini et al. (2010) "Catheter patency and peritoneal morphology and function in a rat model of citrate-buffered peritoneal dialysis." *Peritoneal Dialysis International: Journal of the International Society for Peritoneal Dialysis* 30:602-10.

Churchill et al. (1998) "Increased peritoneal membrane transport is associated with decreased patient and technique survival for continuous peritoneal dialysis patients." *The Canada-USA (Canusa) Peritoneal Dialysis Study Group. Journal of the American Society of Nephrology* 9: 1285-92.

Contreras-Velazquez et al. (2008) "Clinical outcomes and peritoneal histology in patients starting peritoneal dialysis are related to diabetic status and serum albumin levels." *Kidney International* 73: S34-S41. doi: 10.1038/sj.ki.5002599.

Cordeiro et al. (2009) "Systemic and local inflammation in peritoneal dialysis: mechanisms, biomarkers and effects on outcome." *Contrib Nephroi* 163: 132-9.

Coutu et al. (2008) "Periostin, a member of a novel family of vitamin K-dependent proteins, is expressed by mesenchymal stromal cells." *J Biol Chem* 283: 17991-18001.

Dai et al. (2006) "Glucose and diabetes: effects on podocyte and glomerular p38MAPK, heat shock protein 25, and actin cytoskeleton." *Kidney Int* 69: 806-814.

Dai et al. (2009) "Heat shock protein 27 overexpression mitigates cytokine-induced islet apoptosis and streptozotocin-induced diabetes." *Endocrinology* 150: 3031-3039.

Davies (2004) "Longitudinal relationship between solute transport and ultrafiltration capacity in peritoneal dialysis patients." *Kidney International* 66:2437-45.

Davies et al. (1998) "What really happens to people on long-term peritoneal dialysis?" *Kidney International* 54: 2207-17.

De Vriese et al. (2003) "Inhibition of the Interaction of AGE—RAGE Prevents Hyperglycemia-Induced Fibrosis of the Peritoneal Membrane." *Journal of the American Society of Nephrology* 14: 2109-2118.

De Vriese et al. (2006) "Myofibroblast transdifferentiation of mesothelial cells is mediated by RAGE and contributes to peritoneal fibrosis in uraemia." *Nephrology Dialysis Transplantation* 21: 2549-2555.

Devuyst et al. (2010) "The pathophysiology of the peritoneal membrane." *Journal of the American Society of Nephrology: JASN* 21: 1077-85.

Do et al. (2005) "The effect of low glucose degradation product dialysis solution on epithelial-to-mesenchymal transition in continuous ambulatory peritoneal dialysis patients." *Peritoneal Dialysis International: Journal of the International Society for Peritoneal Dialysis* 25(Suppl 3): S22-5.

Docherty et al. (2006) "Endoglin regulates renal ischaemia-reperfusion injury" *Nephrol Dial Transplant* 21: 2106-2119.

Duman et al. (2009) "Technical aspects in studying peritoneal morphology in animal models of peritoneal dialysis." *Peritoneal Dialysis International: Journal of the International Society for Peritoneal Dialysis* 29(Suppl 2): S40-4.

Fehniger et al. (2001) "Interleukin 15: biology and relevance to human disease." *Blood* 97:14-32.

Flessner (2008) "Endothelial glycocalyx and the peritoneal barrier." *Peritoneal Dialysis International: Journal of the International Society for Peritoneal Dialysis* 28: 6-12.

Flessner et al. (2003) "Is the peritoneum a significant transport barrier in peritoneal dialysis?" *Peritoneal Dialysis International: Journal of the International Society for Peritoneal Dialysis* 23:542-9.

Flessner et al. (2006) "Correlating structure with solute and water transport in a chronic model of peritoneal inflammation." *Am J Physiol Renal Physiol* 290:F232-40.

Fracasso et al. (2003) "Effect of oral treatment with the glycosaminoglycan sulodexide on peritoneal transport in CAPD patients." *Peritoneal Dialysis International* 23: 595-599.

Fridman et al. (2010) "Selective inhibition of JAK1 and JAK2 is efficacious in rodent models of arthritis: preclinical characterization of INCB028050." *J Immunol* 184: 5298-307.

Gillan et al. (2002) "Periostin secreted by epithelial ovarian carcinoma is a ligand for alpha(V)beta(3) and alpha(V)beta(5) integrins and promotes cell motility." *Cancer Res* 62: 5358-5364.

Gotloib et al. (1987) "Continuous Mesothelial Injury and Regeneration during Long Term Peritoneal Dial Ysis." *Peritoneal Dialysis International* 7:148-156.

Grzegorzewska et al. (2003) "Dialysate interleukin-15 concentration and ultrafiltration capacity in patients undergoing peritoneal dialysis." *Advances in peritoneal dialysis. Conference on Peritoneal Dialysis* 19:67-72.

Guo et al. (2001) "Hyaluronan preserves peritoneal membrane transport properties." *Peritoneal Dialysis International* 21(2):136-143.

Harrison (2012) "The Jak/STAT pathway." *Cold Spring Harb Perspect Biol* pp. 1-3.

Hendriks et al. (1997) "Peritoneal sclerosis in chronic peritoneal dialysis patients: analysis of clinical presentation, risk factors, and peritoneal transport kinetics." *Peritoneal Dialysis International: Journal of the International Society for Peritoneal Dialysis* 17:136-43; 8 Pages.

Hirahara et al. (2006) "Peritoneal Injury by Methylglyoxal in Peritoneal Dialysis." *Peritoneal Dialysis International* 26:380-392.

Honda et al. (1996) "Morphological changes in the peritoneal vasculature of patients on CAPD with ultrafiltration failure." *Nephron* 72:171-6.

Honda et al. (2008) "Impact of uremia, diabetes, and peritoneal dialysis itself on the pathogenesis of peritoneal sclerosis: a quantitative study of peritoneal membrane morphology." *Clin J Am Soc Nephrol* 3: 720-8. doi: 10.2215/CJN.03630807.

Honda et al. (1999) "Accumulation of advanced glycation end products in the peritoneal vasculature of continuous ambulatory peritoneal dialysis patients with low ultra-filtration." *Nephrology Dialysis Transplantation* 14: 1541-9.

Horiuchi et al. (1999) "Identification and characterization of a novel protein, periostin, with restricted expression to periosteum and periodontal ligament and increased expression by transforming growth factor beta." *J Bone Miner Res* 14: 1239-1249.

Huang et al. (2001) "Role of receptor for advanced glycation end-product (RAGE) and the JAK/STAT-signaling pathway in AGE-induced collagen production in NRK-49F cells." *Journal of Cellular Biochemistry* 81:102-113.

Humphreys et al. (2010) "Fate tracing reveals the pericyte and not epithelial origin of myofibroblasts in kidney fibrosis." *Am J Pathol* 176: 85-97.

Ito et al. (2002) "Tornado extraction: a method to enrich and purify RNA from the nephrogenic zone of the neonatal rat kidney." *Kidney Int* 62: 763-769.

Iwano et al. (2002) "Evidence that fibroblasts derive from epithelium during tissue fibrosis." *J Clin Invest* 110: 341-350.

Jiwakanon et al. (2010) "Peritoneal dialysis: an underutilized modality." *Current Opinion in Nephrology and Hypertension* 19: 573-7.

Johnson et al. (2012.) "The effect of low glucose degradation product, neutral pH versus standard peritoneal dialysis solutions on peritoneal membrane function: the balANZ trial." *Nephrology Dialysis Transplantation* 27(12): 4445-53.

(56) References Cited

OTHER PUBLICATIONS

Kanjanabuch et al. (2008) "Overnight mesothelial cell exfoliation: a magic tool for predicting future ultrafiltration failure in patients on continuous ambulatory peritoneal dialysis." *Peritoneal Dialysis International: Journal of the International Society for Peritoneal Dialysis* 28(Suppl 3): S107-13.

Kanwar et al. (1980) "Increased permeability of the glomerular basement membrane to ferritin after removal of glycosaminoglycans (heparan sulfate) by enzyme digestion." *The Journal of Cell Biology* 86:688-693.

Katsuragi et al. (2004) "Periostin as a novel factor responsible for ventricular dilation." *Circulation* 110: 1806-1813.

Kawashima et al. (2001) "Imaging of Renal Trauma: A Comprehensive Review" *RadioGraphics* 21: 557-574.

Kim et al. (2009) "Corneal Dystrophy-associated R124H Mutation Disrupts TGFBI Interaction with Periostin and Causes Mislocalization to the Lysosome." *Journal of Biological Chemistry* 284: 19580-19591.

Kim et al. (1999) "Effects of peritoneal rest on peritoneal transport and peritoneal membrane thickening in continuous ambulatory peritoneal dialysis rats." *Peritoneal Dialysis International: Journal of the International Society for Peritoneal Dialysis* 19(Suppl 2): S384-7.

Krediet (1999) "The peritoneal membrane in chronic peritoneal dialysis." *Kidney International* 55:341-56.

Krediet (2001) "Dialysate cancer antigen 125 concentration as marker of peritoneal membrane status in patients treated with chronic peritoneal dialysis." *Peritoneal Dialysis International: Journal of the International Society for Peritoneal Dialysis* 21:560-7.

Krediet et al. (2000) "Neoangiogenesis in the peritoneal membrane." *Peritoneal Dialysis International* 20(Supp 2): S19-S25.

Kruzynska-Frejtag et al. (2004) "Periostin is expressed within the developing teeth at the sites of epithelial-mesenchymal interaction." *Dev Dyn* 229: 857-868.

Lai et al. (2007) "Mediators of inflammation and fibrosis." *Peritoneal Dialysis International: Journal of the International Society for Peritoneal Dialysis* 27(Suppl 2): S65-71.

Lai et al. (2010) "Inflammation in peritoneal dialysis." *Nephron Clin Pract* 116: c11-C18.

Lai et al. (2000) "Changes of cytokine profiles during peritonitis in patients on continuous ambulatory peritoneal dialysis." *American Journal of Kidney Diseases* 35(4):644-52; 17 Pages.

Lai et al. (1997) "Dialysate cell population and cancer antigen 125 in stable continuous ambulatory peritoneal dialysis patients: their relationship with transport parameters." *American Journal of Kidney Diseases* 29(5):699-705.

LeBaron et al. (1995) "Beta IG-H3, a novel secretory protein inducible by transforming growth factor-beta, is present in normal skin and promotes the adhesion and spreading of dermal fibroblasts in vitro." *J Invest Dermatol.* 104(5): 844-9.

Leung et al. (2006) "Leptin induces TGF-beta synthesis through functional leptin receptor expressed by human peritoneal mesothelial cell." *Kidney International* 69: 2078-86.

Levey et al. (2007) "Chronic kidney disease as a global public health problem: approaches and initiatives—a position statement from Kidney Disease Improving Global Outcomes." *Kidney Int* 72: 247-259.

Li et al. (2006) "Phosphatidylinositol-3-kinase signaling mediates vascular smooth muscle cell expression of periostin in vivo and in vitro." *Atherosclerosis* 188: 292-300.

Lindner et al. (2005) "Vascular injury induces expression of periostin: implications for vascular cell differentiation and migration." *Arterioscler Thromb Vasc Biol* 25: 77-83.

Litvin et al. (2006) "Periostin and periostin-like factor in the human heart: possible therapeutic targets." *Cardiovasc Pathol* 15: 24-32.

Lopez-Cabrera et al. (2006) "Ex vivo analysis of dialysis effluent-derived mesothelial cells as an approach to unveiling the mechanism of peritoneal membrane failure." *Peritoneal Dialysis International: Journal of the International Society for Peritoneal Dialysis* 26: 26-34.

Lui et al. (2012) "A Combination of Biocompatible Peritoneal Dialysis Solutions and Residual Renal Function, Peritoneal Transport, and Inflammation Markers: A Randomized Clinical Trial." *American journal of kidney diseases* 60(6): 966-75.

Margetts et al. (2003) "Basic mechanisms and clinical implications of peritoneal fibrosis." *Peritoneal Dialysis International: Journal of the International Society for Peritoneal Dialysis* 23: 530-41.

Mohr et al. (2012) "Dynamics and non-canonical aspects of JAK/STAT signalling." *Eur J Cell Biol* 91: 524-32.

Moriishi et al. (2006) "Impact on peritoneal membrane of use of icodextrin-based dialysis solution in peritoneal dialysis patients." *Advances in peritoneal dialysis. Conference on Peritoneal Dialysis* 22:24-28.

Morra et al. (2011) "Periostin expression and epithelial-mesenchymal transition in cancer: a review and an update." *Virchows Archiv* 459:465-475.

Mortier et al. (2004) "Long-term exposure to new peritoneal dialysis solutions: Effects on the peritoneal membrane." *Kidney International* 66:1257-1265.

Nakayama et al. (2003) "Hyper-Vascular Change and Formation of Advanced Glycation Endproducts in the Peritoneum Caused by Methylglyoxal and the Effect of an Anti-Oxidant, Sodium Sulfite." *American Journal of Nephrology* 23: 390-94.

Ni et al. (2010) "Nitric oxide synthase isoforms play distinct roles during acute peritonitis." *Nephrology Dialysis Transplantation* 25: 86-96.

Norris et al. (2004) "Identification and detection of the periostin gene in cardiac development." *Anat Rec A Discov Mol Cell Evol Biol* 281: 1227-1233.

Oh et al. (2010) "Intra-peritoneal interleukin-6 system is a potent determinant of the baseline peritoneal solute transport in incident peritoneal dialysis patients." *Nephrology Dialysis Transplantation* 25:1639-1646.

Oka et al. (2007) "Genetic Manipulation of Periostin Expression Reveals a Role in Cardiac Hypertrophy and Ventricular Remodeling." *Circulation Research* 101: 313-321.

Okada et al. (2003) "Selective depletion of fibroblasts preserves morphology and the functional integrity of peritoneum in transgenic mice with peritoneal fibrosing syndrome." *Kidney International* 64: 1722-1732.

Oku et al. (2008) "Periostin and bone marrow fibrosis." *Int J Hematol* 88: 57-63.

Opatrna et al. (2012) "Intraperitoneal IL-6 Signaling in Incident Patients Treated with Icodextrin and Glucose Bicarbonate/Lactate—Based Peritoneal Dialysis Solutions." *Peritoneal Dialysis International* 32:37-44.

Pahl et al. (2010) "Upregulation of monocyte/macrophage HGFIN (Gpnmb/Osteoactivin) expression in end-stage renal disease." *Clin J Am Soc Nephrol* 5:56-61.

Pecoits-Filho et al. (2002) "Plasma and dialysate IL-6 and VEGF concentrations are associated with high peritoneal solute transport rate." *Nephrology Dialysis Transplantation* 17:1480-1486.

Peso et al. (2008) "Epithelial-to-mesenchymal transition of mesothelial cells is an early event during peritoneal dialysis and is associated with high peritoneal transport." *Kidney International* 73:S26-S33.

Plum et al. (2001) "Peritoneal sclerosis in peritoneal dialysis patients related to dialysis settings and peritoneal transport properties." *Kidney international.* 59(Supp78): S42-S47.

Porcheray et al. (2005) "Macrophage activation switching: an asset for the resolution of inflammation." *Clin Exp Immunol* 142:481-9.

Rani et al. (2009) "Periostin-like-factor and Periostin in an animal model of work-related musculoskeletal disorder." *Bone* 44: 502-512.

Ruan et al. (2009) "The multifaceted role of periostin in tumorigenesis." *Cell Mol Life Sci* 66: 2219-2230.

Sakamoto et al. (2005) "Influence of glucose and inflammatory cytokines on TGF-beta1 and CTGF mRNA expressions in human peritoneal mesothelial cells." *International Journal of Molecular Medicine* 15:907-911.

Sasaki et al. (2002) "Expression of the periostin mRNA level in neuroblastoma." *J Pediatr Surg* 37: 1293-1297.

(56) References Cited

OTHER PUBLICATIONS

Satirapoj (2009) "Identification of periostin as a novel tissue and urinary biomarker for progressive renal injury" *ASN Renal Week 2009* Abstract 554369 pp. 1-2.

Satirapoj (2009) "Overexpression of Oxidized Low-Density Lipoprotein (Ox-LDL) in the Remnant Kidney after 5/6 Nephrectomy (5/6Nx) and Antigen Transport to Renal Lymph Nodes (RLN)" *ASN Renal Week 2009* Abstract 551732 pp. 1-2.

Satirapoj et al. (2012) "Periostin: novel tissue and urinary biomarker of progressive renal injury induces a coordinated mesenchymal phenotype in tubular cells." *Nephrology Dialysis Transplantation* 27:2702-2711.

Sawai et al. (2011) "Peritoneal macrophage infiltration is correlated with baseline peritoneal solute transport rate in peritoneal dialysis patients." *Nephrology Dialysis Transplantation* 26:2322-2332.

Schilte et al. (2009) "Factors contributing to peritoneal tissue remodeling in peritoneal dialysis." *Peritoneal Dialysis International: Journal of the International Society for Peritoneal Dialysis* 29: 605-17.

Schilte et al. (2009) "Long-term intervention with heparins in a rat model of peritoneal dialysis." *Peritoneal Dialysis International: Journal of the International Society for Peritoneal Dialysis* 29:26-35.

Selgas et al. (2006) "Epithelial-to-mesenchymal transition of the mesothelial cell--its role in the response of the peritoneum to dialysis." *Nephrology, dialysis, transplantation* 21 Suppl 2:ii2-7.

Sen et al. (2010) "Identification of Periostin as a Novel Matricellular Protein Linked to Progression of Glomerulonephropathies" *ASN Renal Week 2010* Abstract SA-PO2880 p. 1.

Shao et al. (2004) "Acquired expression of periostin by human breast cancers promotes tumor angiogenesis through up-regulation of vascular endothelial growth factor receptor 2 expression." *Mol Cell Biol* 24(9):3992-4003.

Sturm et al. (1975) "Renal Artery and vein injury following blunt trauma" *Ann. Sur.* 186(6): 696-698.

Suassuna et al. (1994) "Immunohistochemical studies of the peritoneal membrane and infiltrating cells in normal subjects and in patients on CAPD." *Kidney International* 46:443-54.

Takayama et al. (2006) "Periostin: a novel component of subepithelial fibrosis of bronchial asthma downstream of IL-4 and IL-13 signals." *J Allergy Clin Immunol* 118: 98-104.

Takeshita et al. (1993) "Osteoblast-specific factor 2: cloning of a putative bone adhesion protein with homology with the insect protein fasciclin I." *Biochem J* 294 ( Pt 1): 271-278.

Topley (1995) "The cytokine network controlling peritoneal inflammation." *Peritoneal Dialysis International* 15(7) Suppl: S35-S39; 6 Pages.

van den Berg et al. (2006) "Glycocalyx perturbation: cause or consequence of damage to the vasculature?" *American Journal of Physiology—Heart and Circulatory Physiology* 290: H2174-H2175.

Vassalotti et al. (2007) "Testing for chronic kidney disease: a position statement from the National Kidney Foundation." *Am J Kidney Dis* 50: 169-180.

Visser et al. (1998) "Chemokines produced by mesothelial cells: huGRO-alpha, IP-10, MCP-1 and RANTES." *Clin Exp Immunol* 112: 270-5.

Wallace et al. (2008) "Periostin induces proliferation of human autosomal dominant polycystic kidney cells through alphaV-integrin receptor." *Am J Physiol Renal Physiol* 295: F1463-1471.

Wang et al. (2001) "Peritoneal dialysis solutions." *Peritoneal Dialysis International* 21(Supp 3): S89-S95.

Wang et al. (1998) "Hyaluronan prevents the decreased net ultrafiltration caused by increased peritoneal dialysate fill volume." *Kidney International* 53:496-502.

Wang et al. (1997) "Daily exposure to dialysis fluid results in changes in peritoneal transport." *Peritoneal Dialysis International: Journal of the International Society for Peritoneal Dialysis* 17:379-86.

Warnock et al. (2012) "Prospective safety study of bardoxolone methyl in patients with Type 2 diabetes mellitus, end-stage renal disease and peritoneal dialysis." *Contributions to Nephrology* 178: 157-63.

Webmaster (2008) "The Foundation for IgA Nephropathy" What IgAN is (a summary) pp. 1-3.

Welten et al. (2003) "Single exposure of mesothelial cells to glucose degradation products (GDPs) yields early advanced glycation endproducts (AGEs) and a proinflammatory response." *Peritoneal Dialysis International* 23 :213-221.

Williams et al. (2002) "Morphologic Changes in the Peritoneal Membrane of Patients with Renal Disease." *Journal of the American Society of Nephrology* 13:470-479.

Williams et al. (2003) "The natural course of peritoneal membrane biology during peritoneal dialysis." *Kidney International* 64: S43-S49.

Yan et al. (2006) "Transduction of a mesenchyme-specific gene periostin into 293T cells induces cell invasive activity through epithelial-mesenchymal transformation." *J Biol Chem* 281: 19700-19708.

Yanez-Mo et al. (2003) "Peritoneal dialysis and epithelial-to-mesenchymal transition of mesothelial cells." *The New England Journal of Medicine* 348: 403-13.

Yu et al. (2009) "HGF and BMP-7 ameliorate high glucose-induced epithelial-to-mesenchymal transition of peritoneal mesothelium." *Journal of the American Society of Nephrology : JASN* 20: 567-81.

Yung et al. (2004) "Reduction of perlecan synthesis and induction of TGF-beta1 in human peritoneal mesothelial cells due to high dialysate glucose concentration: implication in peritoneal dialysis." *Journal of the American Society of Nephrology: JASN* 15: 1178-88.

Yung et al. (2007) "Glycosaminoglycans and proteoglycans: overlooked entities?" *Peritoneal Dialysis International: Journal of the International Society for Peritoneal Dialysis* 27(Suppl 2): S104-9.

Zareie et al. (2005) "Peritoneal dialysis fluid-induced changes of the peritoneal membrane are reversible after peritoneal rest in rats." *Nephrology Dialysis Transplantation* 20: 189-93.

Zhu et al. (1997) "Macrophage differentiation and expression of macrophage colony-stimulating factor in murine milky spots and omentum after macrophage elimination." *J Leukoc Biol* 61:436-44.

Zuurbier et al. (2005) "Short-term hyperglycemia increases endothelial glycocalyx permeability and acutely decreases lineal density of capillaries with flowing red blood cells." *Journal of Applied Physiology* 99:1471-1476.

\* cited by examiner

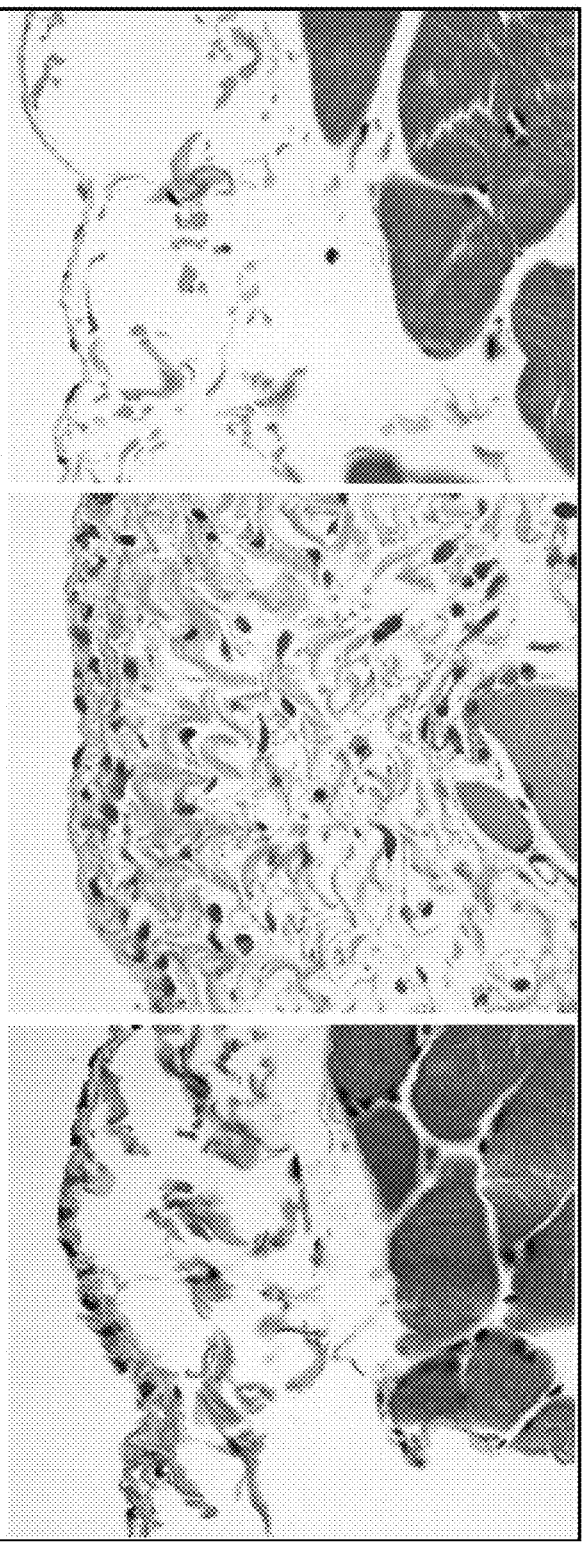
FIG. 5A-C

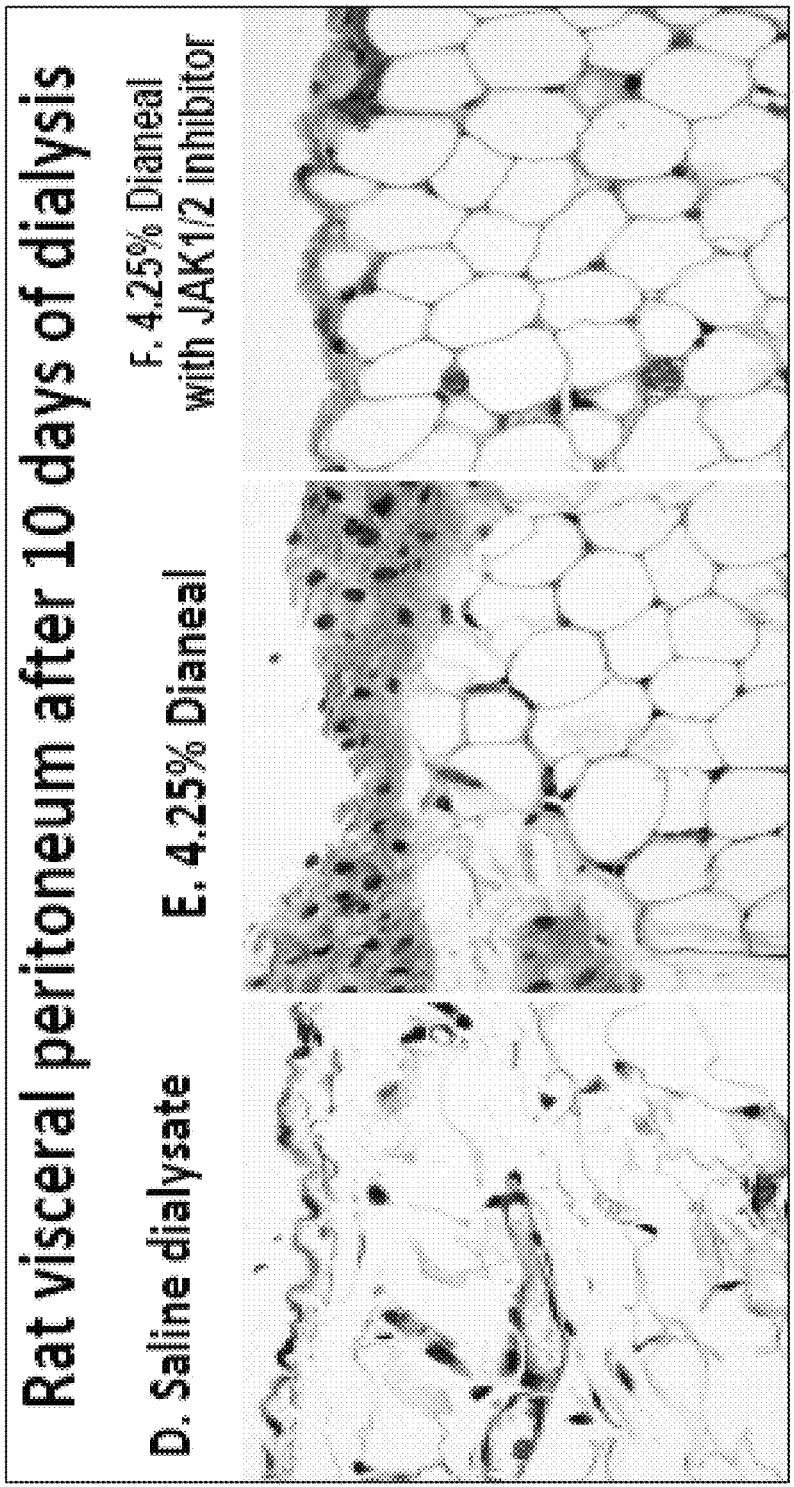
FIG. 5D-F

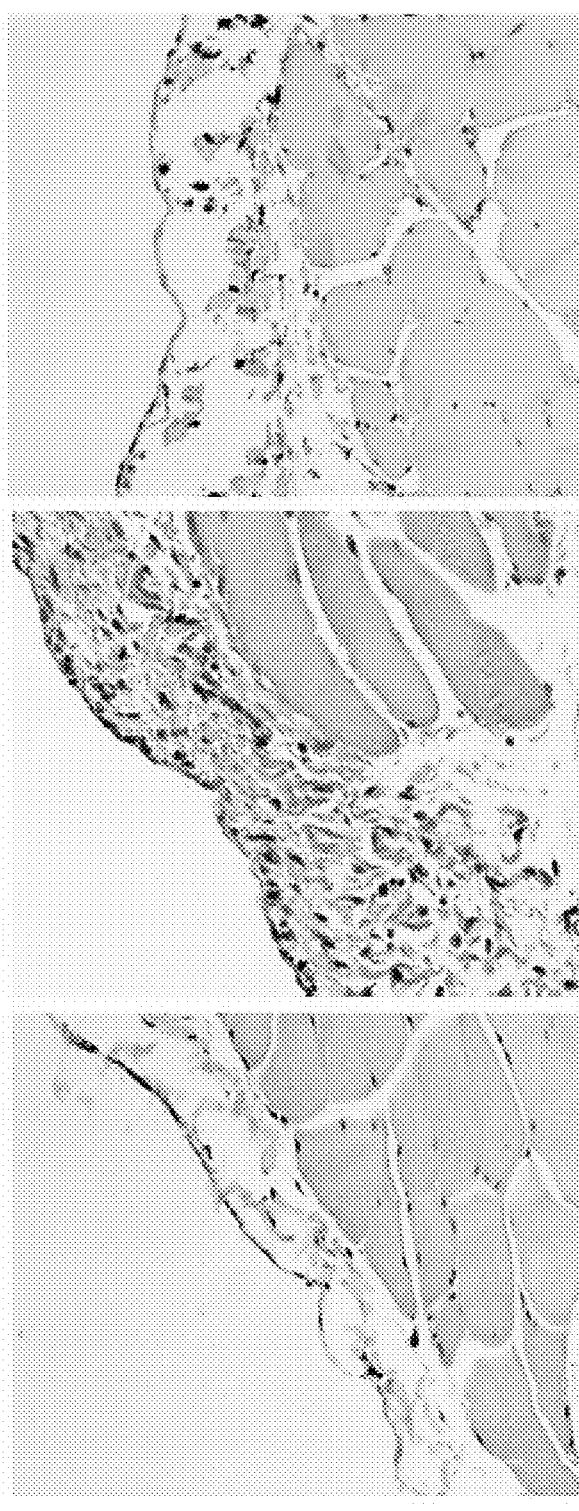
FIG. 5G-I

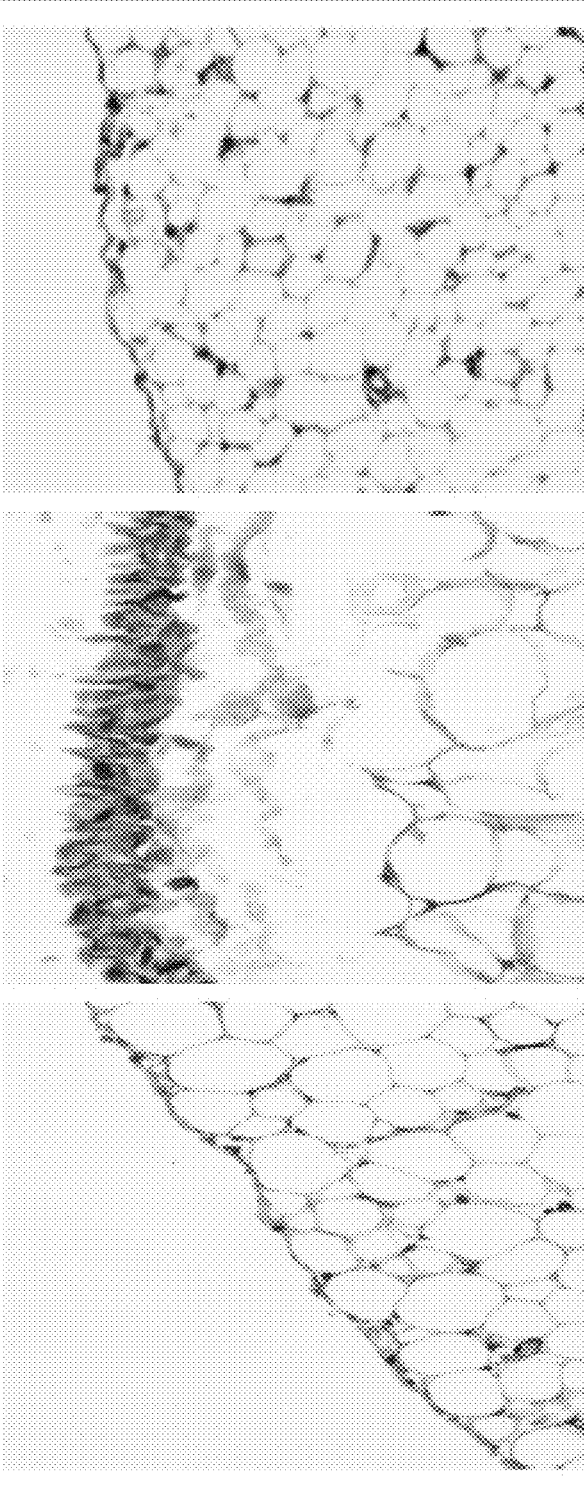
FIG. 5J-L

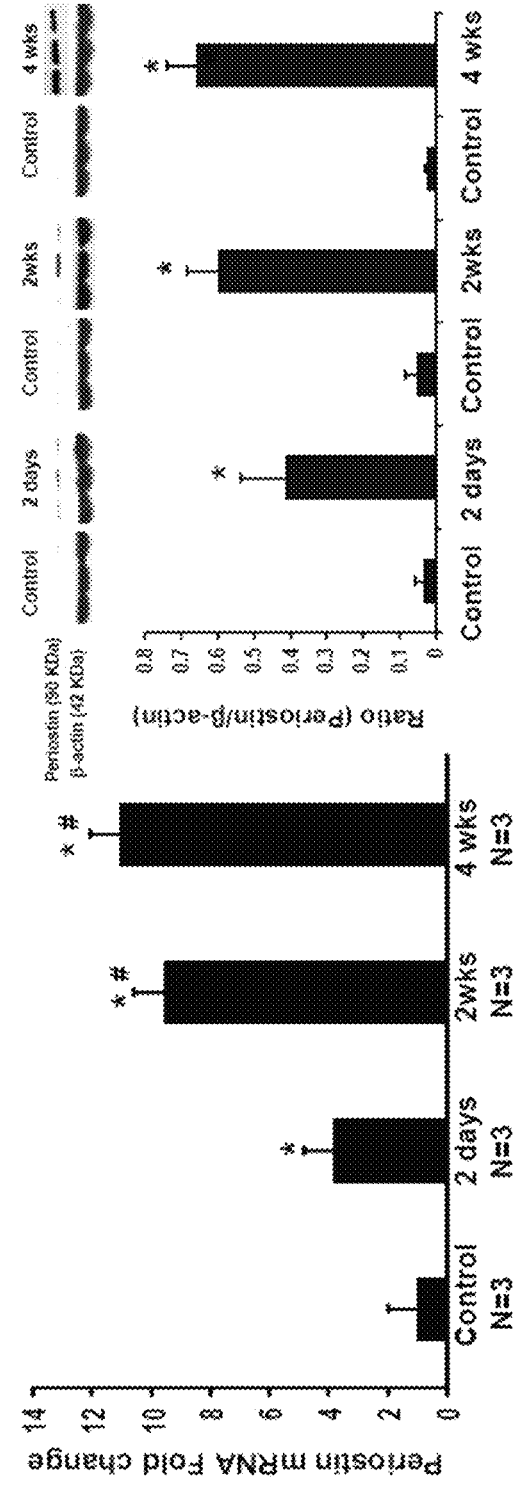
FIG. 6A-B

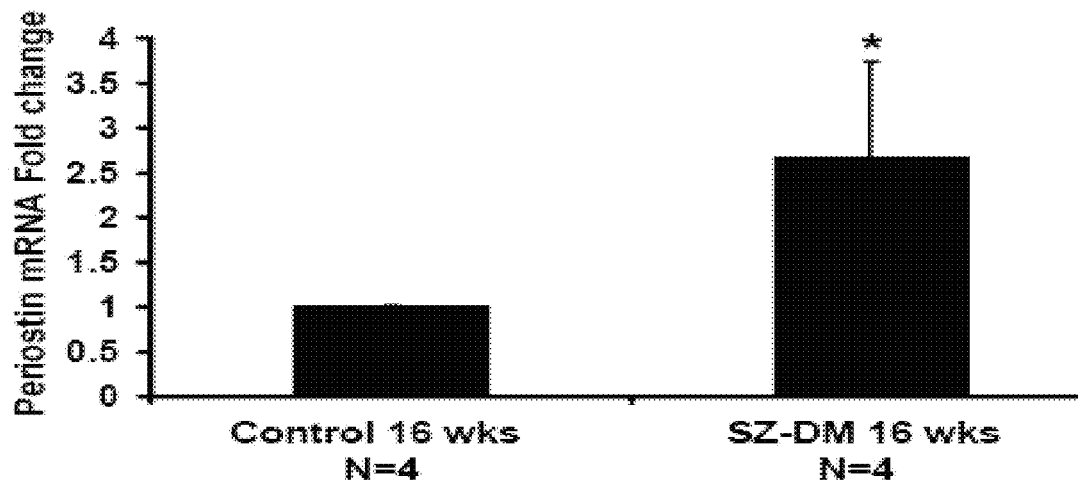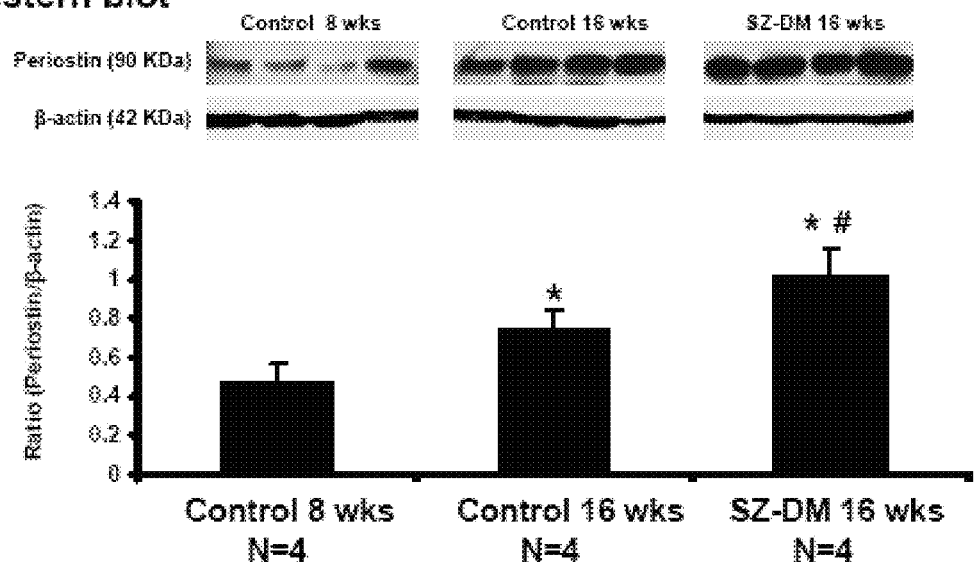
FIG. 7A-B

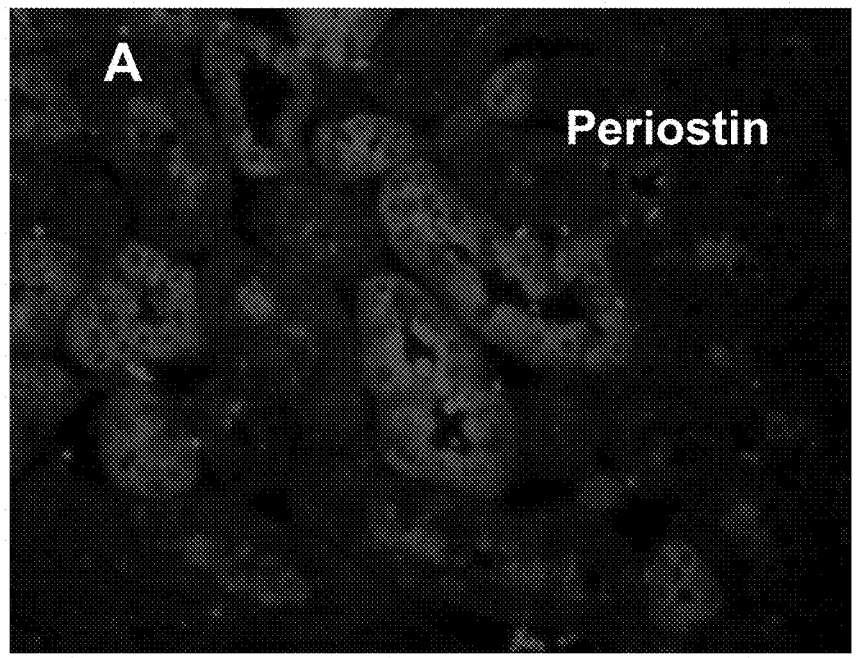
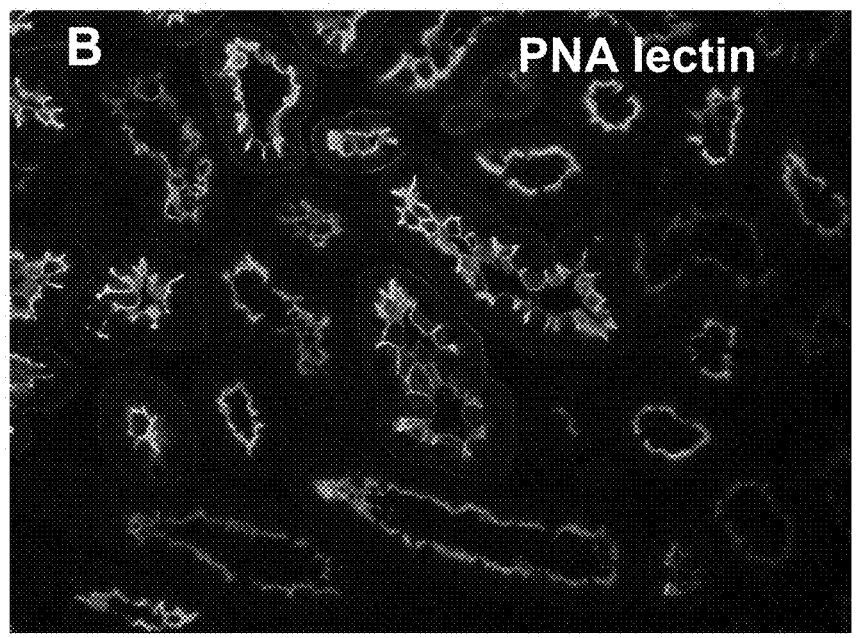
FIG. 8A-B

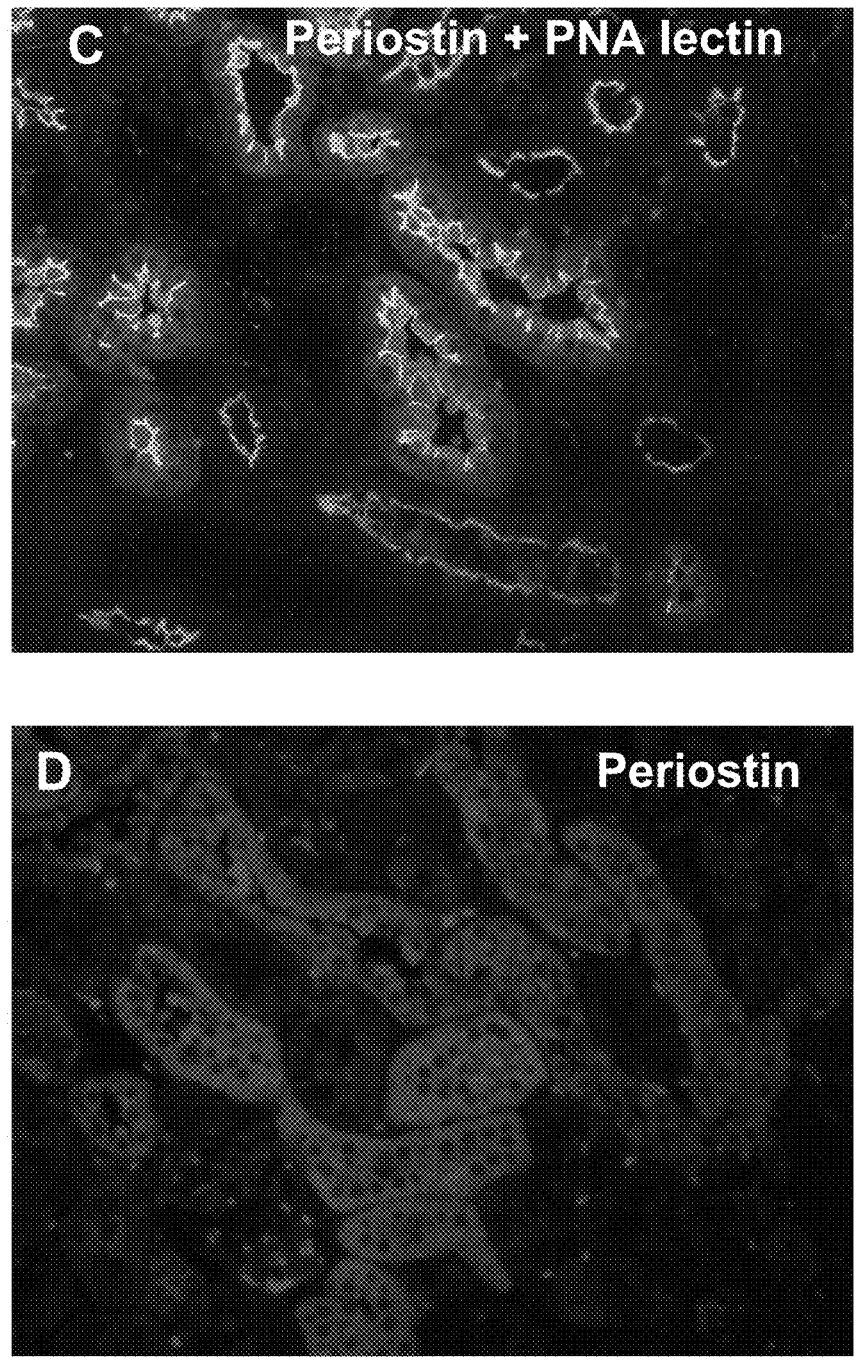
FIG. 8C-D

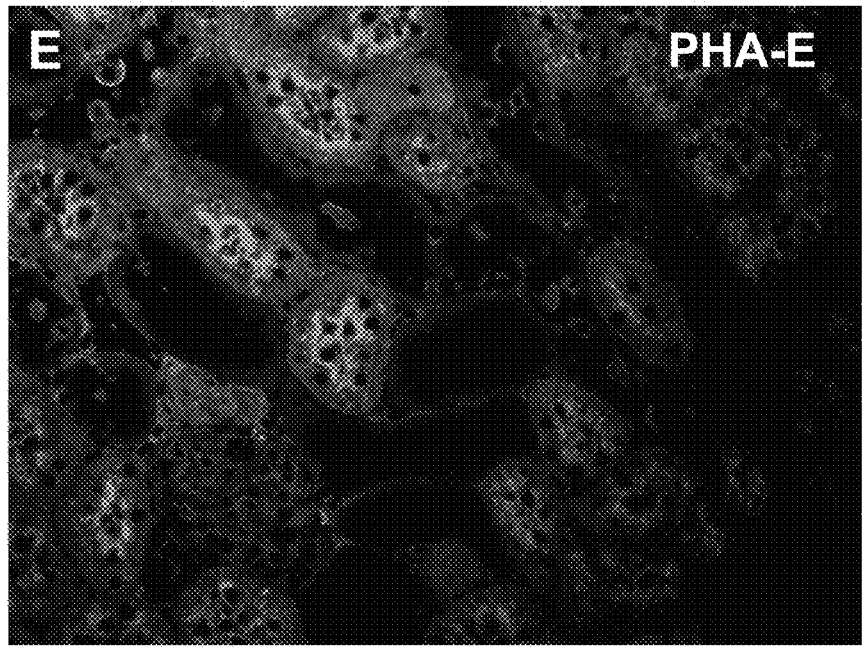
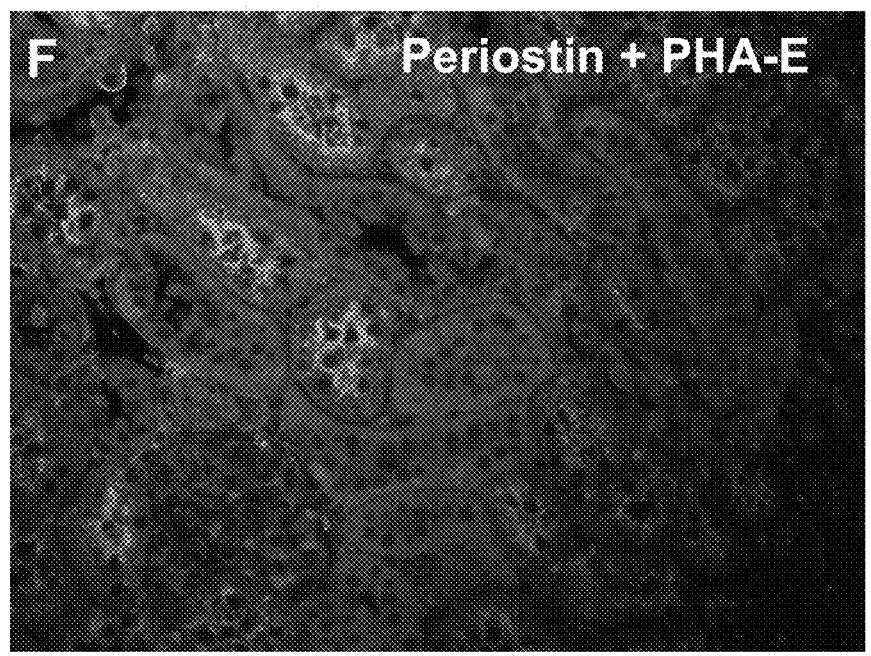
*FIG. 8E-F*

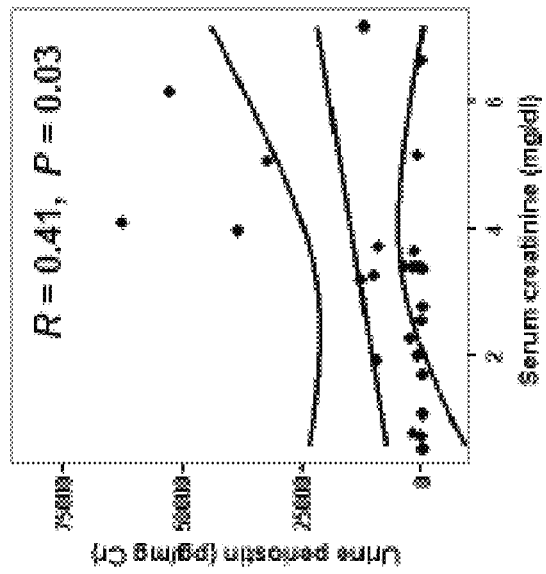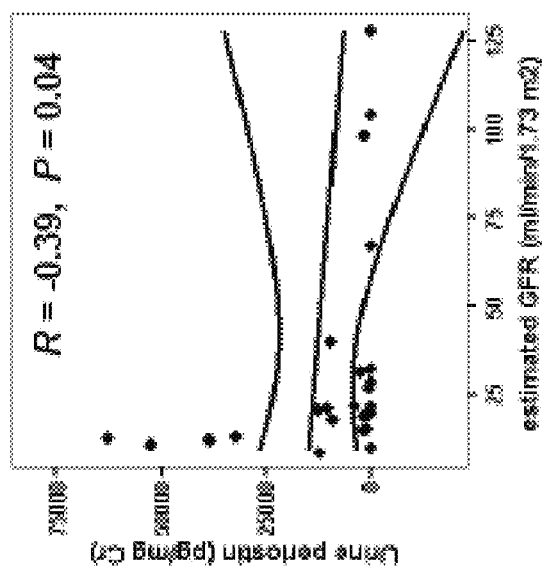
FIG. 12 B1-B2

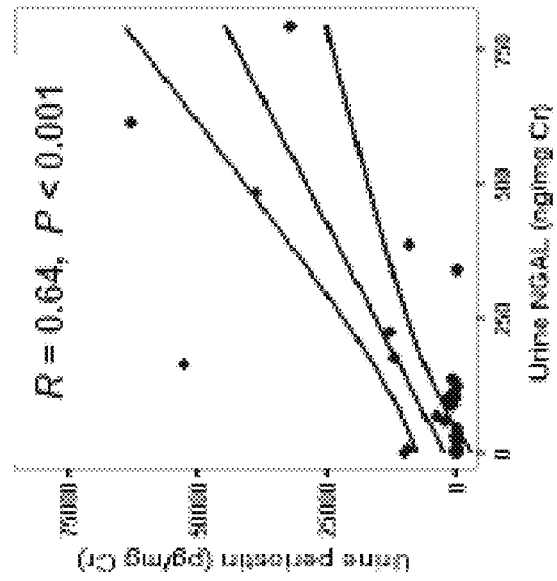
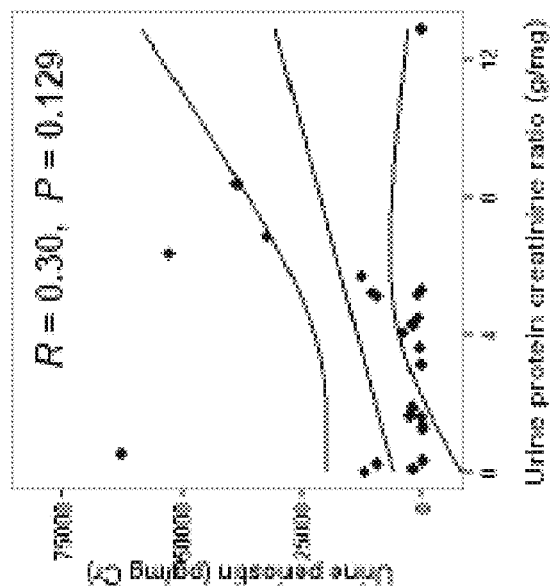
FIG. 12 B3-B4

A
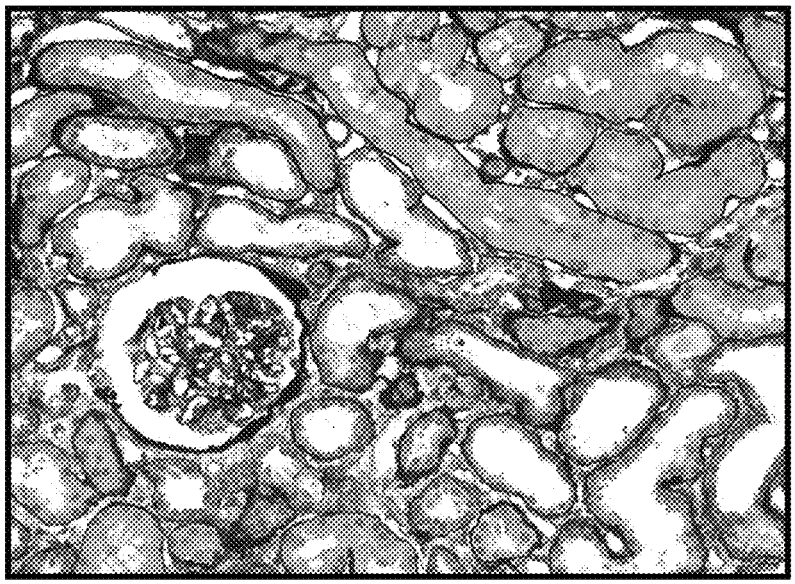
B
Urine periostin in LN patient
with serum creatinine 1.0 mg/dL
90 kDa 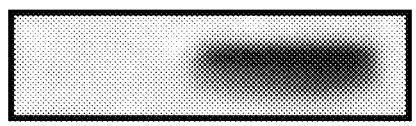
Control    LN patient
*FIG. 13A-B*

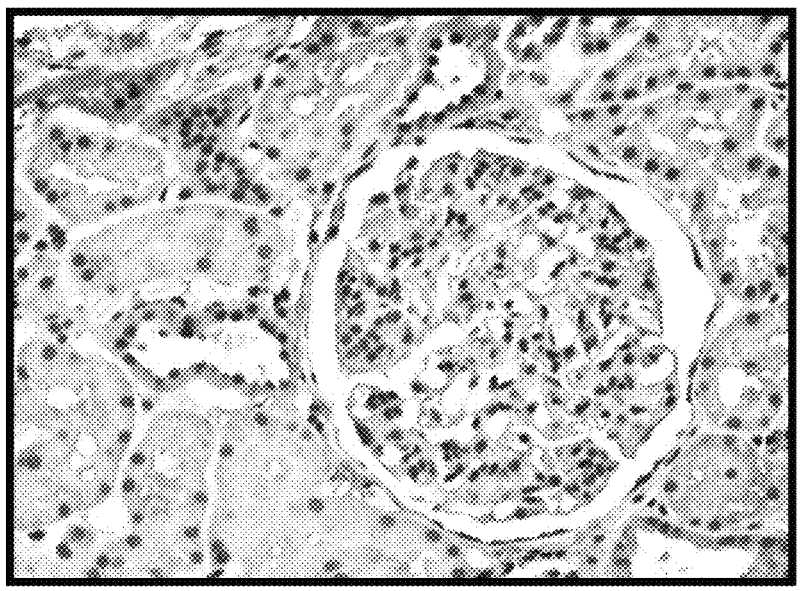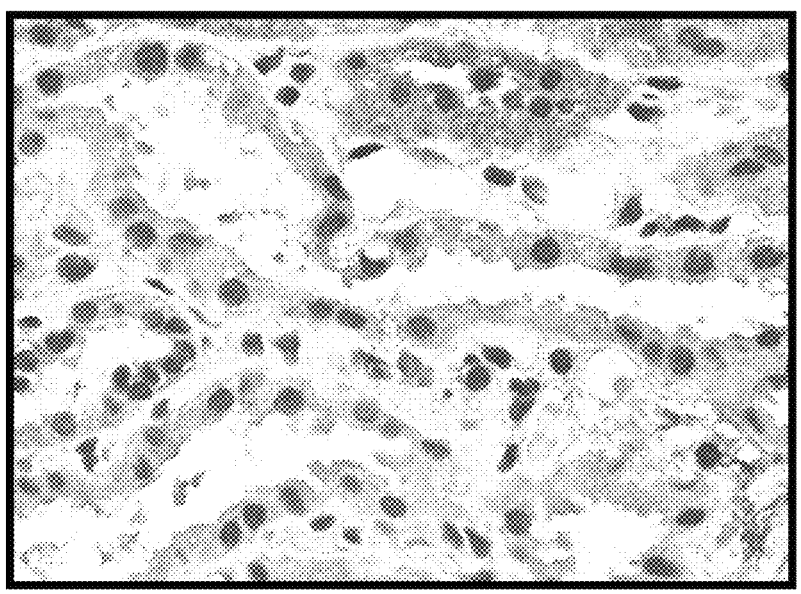
FIG. 13C-D

```
                        SEQUENCE LISTING

<160> NUMBER OF SEQ ID NOS: 2

<210> SEQ ID NO 1
<211> LENGTH: 21
<212> TYPE: DNA
<213> ORGANISM: Mus musculus

<400> SEQUENCE: 1
tggtgttgtc catgtcatcg a                                              21

<210> SEQ ID NO 2
<211> LENGTH: 22
<212> TYPE: DNA
<213> ORGANISM: Mus musculus

<400> SEQUENCE: 2
tgtgaagtga ccgtctcttc ca                                             22
```

TREATMENT OF PERITONEAL INJURY USING JAK INHIBITORS

CROSS-REFERENCE TO RELATED APPLICATIONS

This application is a continuation-in-part of U.S. patent application Ser. No. 13/665,283, filed Oct. 31, 2012, which claims the benefit of U.S. Provisional Application No. 61/558,292, filed Nov. 10, 2011, each of which is hereby incorporated by reference in its entirety.

FIELD OF THE INVENTION

The invention relates to the use of JAK inhibitors to treat or prevent peritoneal injury and/or to improve peritoneal function. The invention also relates to the use of periostin as a marker for peritoneal injury.

BACKGROUND OF THE INVENTION

The technique of peritoneal dialysis (PD) as an end stage renal disease (ESRD) replacement therapy is becoming more accepted. Currently in the United States, approximately 8% of patients requiring renal replacement therapy choose this modality of treatment. High technical failure rates diminish PD utilization globally, but especially in the US, where bicarbonate-based PD solution is unavailable. There are many causes, including peritoneal barrier (Pbarrier) exposure to lactate, low dialysate pH, high glucose, advanced glycation end products (AGE), glucose-degradation products (GDP) generated from peritoneal dialysis fluid (PDF) heat sterilization, inflammatory foreign-body response to the catheter, uremia, and peritonitis. Uremia induces considerable structural Pbarrier pathology. Prior to initiating PD, impaired peritoneal structural integrity from uremia is associated with Pbarrier pathology. However, during PD, further compromise is driven by continued oxidant injury, inflammation, and a crescendo of chemokine, cytokine, and growth factor elaboration by resident Pbarrier cells and infiltrating mononuclear cells.

PD limitations involve failure of the peritoneal membrane as a dialyzer, and particularly, failure of the peritoneal membrane to ultrafilter fluid. This is measured and defined by the peritoneal equilibration test (PET), with patients who have high normal or high values indicating pathology. However, while the measurement of a high or high normal PET indicates membrane pathology, the measure is not linked to pathological processes per se, and is not observed early enough in the process so that changes in prescription or modality can be implemented early to redress injury and optimally benefit patients. More rarely, the peritoneum fails in a process called encapsulating peritoneal sclerosis (EPS). This tends to be associated usually, but not always, with prolonged use of the modality (e.g., with the incidence increasing substantially with >10 years of PD performance) and with prior episodes of peritonitis. Although both high PET and EPS involve peritoneal membrane failure, high PET status can often be overcome by prescription changes, or, at worst, modality discontinuation with transfer to hemodialysis or transplantation, but EPS is often fatal. The pathophysiological relationship between the two processes is also poorly defined, and validated biomarkers for the early identification of the presence of these syndromes are not available.

Failure of the PD membrane as a dialyzer is not a universal phenomenon even after many years of treatment, although injury to the peritoneum imposed by using it as a dialysis membrane may be common. The only difference between failure and injury appears to be the degree to which the injury imposed by the technique varies. In some, only histologic injury is apparent; in others, injury induces functional membrane failure. When functional membrane failure occurs differs among affected individuals, and the risk factors for its occurrence are incompletely understood. Apart from biologic variation in responses of individuals, two key factors appear to convey risk. One factor is the occurrence of peritonitis, and a second is exposure over long periods of time to high concentrations of glucose in the dialysate. Both of these risk features can be addressed, but especially the latter, which can be modified by a change in dialysate prescription. Thus, the earlier one can identify peritoneal injury, the earlier one can change prescriptions to minimize injury, take measures to prevent or treat peritoneal injury, or, in extreme cases, discontinue PD and switch to another ESRD renal replacement modality. Validated biomarkers for early peritoneal injury and for peritoneal injury progression are currently not available. While the PET defines injury to the peritoneal membrane that significantly interferes with peritoneal membrane function, it does not address the pathophysiology of membrane failure.

Periostin, a member of a novel vitamin K-dependent gamma-carboxylated protein family characterized by the presence of fasciclin domains, is induced in processes and pathologies including cardiac embryogenesis, osteogenesis, adult cardiac disease, metastatic disease, tumor suppression, and acute and chronic renal injury. Periostin was initially identified in osteoblasts and acts as an adhesion molecule during bone formation, supports osteoblastic cell line attachment, and is involved in cell survival, proliferation, migration, and differentiation.

SUMMARY OF THE INVENTION

In various aspects, the invention(s) contemplated herein may include, but need not be limited to, any one or more of the following embodiments:

Embodiment 1

A method of preventing and/or treating peritoneal injury and/or improving peritoneal membrane function including administering an effective amount of an inhibitor of the JAK/STAT pathway to a subject who is at risk of peritoneal injury and/or has at least one symptom or sign of peritoneal injury and/or of diminished peritoneal membrane function, wherein the effective amount is an amount sufficient to reduce the subject's risk of peritoneal injury and/or mitigate the subject's at least one symptom or sign of peritoneal injury and/or improve peritoneal membrane function.

Embodiment 2

A pharmaceutical composition including an inhibitor of the JAK/STAT pathway for use in preventing and/or treating peritoneal injury and/or improving peritoneal membrane function in a subject.

Embodiment 3

The pharmaceutical composition of embodiment 2, further including a pharmaceutically acceptable carrier.

Embodiment 4

The method of embodiment 1 or the composition of embodiments 2-3, wherein the inhibitor of the JAK/STAT pathway is an inhibitor of JAK.

Embodiment 5

The method or composition of embodiment 4, wherein the subject is not one who is being administered an inhibitor of the JAK/STAT pathway to treat or prevent rheumatoid arthritis, cancer, psoriasis, polycythemia vera, essential thrombocytosis, diabetic kidney disease, or myelofibrosis.

Embodiment 6

The method or composition of embodiments 4-5, wherein the inhibitor of JAK inhibits kinases selected from the group consisting of JAK1, JAK2, JAK3, TYK2, and any combination thereof.

Embodiment 7

The method or composition of embodiments 4-5, wherein the inhibitor of JAK is selected from the group consisting of: Baricitinib (LY3009104, INCB28050); Lestaurinib, Pacritinib (SB1518); Ruxolitinib; Tofacitinib (tasocitinib, CP-690, 550); AC-430; AG490; AUH-6-96; AZ-01, AZ-60; AZ960; BMS-911543; CEP-701; CEP-33779; CMP6; CP-690,550; CP-352,664; CYT387; GLPG-0634; JAK2-IA; INCB20; INCB18424; INCB028050; LS104; narrow-spectrum JAK1/2 inhibitor LSN 3103801; pan-JAK inhibitor P6; PS-608504; PS-020613; Pyridone 6; R-348; R-732; SB1518; TG101209; TG101348; WHI-PI 54; WP1066; XL-019; ortho-substituted pyrimidine compounds; imidazopyridine derivatives; heterocyclyl pyrazolopyrimidine analogues; pyrrolo[2,3-d]pyrimidine urea compounds; Tricylic JAK1 inhibitors; Anilinophthalazine-based JAK1 inhibitors; Isoquinolines; Pyrrolo[2,3-d]pyrimidines; quinazolines; Thieno[2,3-d]pyrimidines and pyrrolo[1,2-f][1,2,4]triazines; Imidazo[2,3-c]pyridines; Diaminopyrimidines and pyridines; Imidazo[4,5-c]pyrrolo[2,3-b]pyridines; [1,2,4]triazolo[1,5-a]pyridine derivatives; Pyrrolo[1,2-f][1,2,4]triazines; Diphenylpyrrolo[1,2-f][1,2,4]triazin-2-amines; 7,8-Dihydropyrido[4,3-d]pyrimidin-5(6H)-ones; single amino pyrazole clinical candidate 'LY2784544'; Triazolo[1,5-a]pyridines; Pyrazolo[1,5-a]pyrimidines; Pyrrolo[2,3-d]pyrimidines; Pyrrolo[2,3-d]pyrimidines; Macrocyclic diaminopyrimidines; Pyrazoles and thiazoles; indazoles; Pyrrolo[2,3-d]pyrimidines; Diaminopyrimidines; heterocycles; Furan[2,3-d]pyrimidines; pyrrolo[1,2-b]pyridazine; Pyrazolo[3,4-d]pyrimidines; Diaminopyrimidines; Pyrrolo[2,3-b]pyridines; Diamino-pyridine-3-carboxyamides; Diamino-amido-pyrimidines; Diamino-pyridines; Diamino-pyrimidines; Pyrrolo[2,3-b]pyrazines, diaminopyridines and macrocyclic compounds; Tricyclic naphthyridinones; 3H-pyrrolo[3,2-f][1,7]naphthyridines; Various heterocycles; Purin-8-ones; Bipyridyl benzamides; Tricyclic Pyrrolopyrrolopyridines; Pyrrolo[2,3-d]pyrimidines; macrocyclic anilinopyrrolo[2,3-d]pyrimidines; Pyrrolo[2,3-d]pyrimidines and pyrrolo[2,3-b]pyridines; Pyrrolo[2,3-d]pyrimidines and pyrrolo[2,3-b]pyridines; Imidazo[4,5-d]pyridines and pyrazolo[2,3-a]pyridines; TYK2 inhibitors; TYK2 inhibitor; Triazolopyridine TYK2 inhibitors; Monocyclic TYK2 inhibitors; and any combination thereof.

Embodiment 8

The method or composition as in any of the preceding embodiments, wherein the subject is a human peritoneal dialysis patient.

Embodiment 9

A method of detecting an indicator of peritoneal injury, the method including assaying a biological sample for periostin protein or mRNA, wherein the biological sample is selected from the group consisting of a cell collected from used peritoneal dialysate, peritoneal tissue, and one or more fractions thereof, and wherein the presence of periostin protein or mRNA at an elevated level indicates the presence and/or degree of peritoneal injury.

Embodiment 10

A method of detecting an indicator of peritoneal injury, the method including assaying a biological sample for periostin protein or mRNA, wherein the biological sample is peritoneal fluid or one or more fractions thereof, and wherein the presence of periostin protein or mRNA at an elevated level indicates the presence and/or degree of peritoneal injury.

Embodiment 11

The method of embodiments 9 or 10, wherein periostin is detected as an indicator selected from the group consisting of a diagnostic indicator of peritoneal injury; an indicator of progression, remission, or relapse of peritoneal injury; and an indicator of response to treatment for peritoneal injury.

Embodiment 12

The method of any of embodiments 9-11, wherein periostin is detected as an indicator of mesothelial to mesenchymal transition (MMT).

Embodiment 13

A method for identifying a subject as a candidate for prevention and/or treatment of peritoneal injury, the method including: assaying a biological sample for periostin protein or mRNA, wherein the biological sample is selected from the group consisting of a cell collected from used peritoneal dialysate, peritoneal tissue, and one or more fractions thereof; and identifying the subject as a candidate for the prevention and/or treatment of peritoneal injury if periostin protein or mRNA is present in the biological sample at an elevated level.

Embodiment 14

A method for identifying a subject as a candidate for prevention and/or treatment of peritoneal injury, the method including: assaying a biological sample for periostin protein or mRNA, wherein the biological sample is peritoneal fluid or one or more fractions thereof; and identifying the subject as a candidate for the prevention and/or treatment of peritoneal injury if periostin protein or mRNA is present in the biological sample at an elevated level.

Embodiment 15

The method of any of embodiments 9-14, wherein the biological sample includes a human biological sample.

Embodiment 16

The method of any of embodiments 9-15, wherein the biological sample includes used peritoneal dialysate or a fraction thereof.

Embodiment 17

The method of any of embodiments 9-15, wherein the biological sample includes peritoneal fluid or a fraction thereof.

Embodiment 18

The method of any of embodiments 9-15, wherein the biological sample includes peritoneal tissue or a fraction thereof.

Embodiment 19

The method of any of embodiments 9-18, wherein the human is a human peritoneal dialysis patient.

Embodiment 20

The method of embodiment 15, wherein the human is a human patient known to have, or suspected of having, peritoneal injury.

Embodiment 21

A method for detecting an indicator of a subject's response to treatment for peritoneal injury, the method including assaying a biological sample obtained from a subject, after initiation of treatment for peritoneal injury, for periostin protein or mRNA, wherein the level of periostin protein or mRNA is positively correlated with the degree of peritoneal injury.

Embodiment 22

The method of embodiment 21, wherein a baseline level of periostin protein or mRNA is measured prior to initiation of treatment for peritoneal injury.

Embodiment 23

The method of embodiment 22, wherein the periostin protein or mRNA level of the biological sample after initiation of treatment is compared to the baseline level of periostin protein or mRNA.

Embodiment 24

The method of embodiment 23, wherein a decrease in the periostin protein or mRNA level of the biological sample after initiation of treatment, as compared to the baseline level of periostin protein or mRNA, indicates that the subject is responding to the treatment.

Embodiment 25

The method of any of embodiments 13-24, wherein the subject is a peritoneal dialysis patient, and said treatment for peritoneal injury is selected from altering composition of the dialysate, terminating peritoneal dialysis, any treatment of embodiments 1-8, or a combination thereof.

Embodiment 26

The method of embodiment 21, wherein said treatment for peritoneal injury includes the method of any of embodiments 1, and 4-8.

Embodiment 27

The method of embodiment 23, wherein one or more additional assays of periostin protein or mRNA are performed as treatment is continued.

Embodiment 28

The method of embodiments 9-27, the method additionally including detecting one or more additional indicators of peritoneal injury selected from the group consisting of PDGF, collagen IV, the peritoneal equilibration test (PET), and encapsulating peritoneal sclerosis (EPS).

Embodiment 29

The method of embodiments 9-28, wherein periostin protein or mRNA is detected by a method selected from the group consisting of an immunoassay, electrochemiluminescence, HPLC, mass spectroscopy, hybridization, and polymerase chain reaction (PCR).

Embodiment 30

The method of embodiments 9-29, wherein the assaying a biological sample for periostin mRNA includes amplifying the periostin mRNA.

Embodiment 31

The method of embodiments 9-30, wherein periostin protein or mRNA is detected in an assay wherein the periostin protein or mRNA, or DNA derived therefrom, is transformed from a free state to a bound state by forming a complex with another assay component.

Embodiment 32

The method of embodiment 31, wherein the other assay component includes a capture agent, and the complex includes an analyte/capture agent complex.

Embodiment 33

The method of embodiment 32, wherein the capture agent includes one or more monoclonal antibodies, or fragments thereof, or polyclonal antibodies.

Embodiment 34

The method of embodiment 32, wherein the capture agent includes one or more nucleic acid probes.

Embodiment 35

The method of embodiments 9-34, wherein periostin protein or mRNA, or DNA derived therefrom, is detected in an assay wherein the periostin protein or mRNA becomes labeled with a detectable label.

Embodiment 36

The method of embodiment 35, wherein the detectable label includes at least one labeled detection agent or labeled nucleic acid.

Embodiment 37

The method of embodiment 36, wherein the label is selected from the group consisting of magnetic beads, fluo-

Embodiment 38

The method of embodiments 9-37, wherein periostin protein or mRNA is detected in an assay wherein periostin protein or mRNA, or DNA derived therefrom, initially present in a soluble phase becomes immobilized on a solid phase.

Embodiment 39

The method of embodiment 38, wherein the solid phase includes one or more microporous structures or microparticles.

Embodiment 40

The method of embodiment 39, wherein the microparticles are suspended in a mixture of soluble reagents and the biological sample.

Embodiment 41

The method of embodiment 39, wherein the microparticles are retained and immobilized by a support material.

Embodiment 42

The method of embodiments 38, wherein the solid phase includes one or more electrodes.

Embodiment 43

The method of embodiments 38-42, wherein the solid phase includes a charged substance coated on the solid phase material.

Embodiment 44

The method of embodiments 38-43, wherein at least one surface of the solid phase is configured to be activated before the periostin protein or mRNA, or DNA derived therefrom, becomes immobilized on the solid phase.

Embodiment 45

The method of embodiments 38-44, wherein at least one surface of the solid phase is reacted with one or more linkers that are configured to link the solid phase to one or more analytes.

Embodiment 46

The method of embodiments 38-45, wherein at least one surface of the solid phase is laminated with one or more proteins or macromolecules.

Embodiment 47

The method of embodiments 38-46, wherein at least one surface of the solid phase is polyfunctional or capable of being polyfunctionalized.

Embodiment 48

The method of embodiments 9-45, wherein periostin protein or mRNA, or DNA derived therefrom, is detected in an assay wherein the sample is fractionated to separate periostin protein or mRNA, or DNA derived therefrom, from at least one other sample component.

Embodiment 49

The method of embodiments 9-48, wherein periostin protein or mRNA, or DNA derived therefrom, is detected in an assay wherein periostin protein or mRNA, or DNA derived therefrom, becomes embedded in a separation medium.

Embodiment 50

The method of embodiments 9-49, wherein periostin protein is detected in an assay wherein periostin protein is volatilized.

Embodiment 51

The method of embodiments 9-50, additionally including recording the periostin protein or mRNA level, and/or a diagnosis based at least in part on the periostin protein or mRNA level, in a patient medical record.

Embodiment 52

The method of embodiment 51, wherein said recording includes recording the periostin protein or mRNA level in a computer-readable medium.

Embodiment 53

The method of embodiment 51, wherein said patient medical record is maintained by a laboratory, physician's office, a hospital, a health maintenance organization, an insurance company, or a personal medical record website.

Embodiment 54

The method of The method of embodiments 9-53, wherein a diagnosis, based at least in part on the periostin protein or mRNA level, is recorded on or in a medic alert article selected from a card, worn article, or radiofrequency identification (RFID) tag.

Embodiment 55

The method of embodiments 9-54, additionally including informing the subject of a result of the periostin protein or mRNA assay and/or of a diagnosis based at least in part on the periostin protein or mRNA level.

Embodiment 56

The method of embodiments 9-55, additionally including ordering and/or performing one or more additional assays.

Embodiment 57

The method of embodiment 56, wherein the periostin protein or mRNA level determined in said assay is not elevated, and the additional assay includes an additional periostin protein or mRNA assay.

Embodiment 58

The method of embodiment 56, wherein the periostin protein or mRNA level determined in said assay is elevated.

Embodiment 59

The method of embodiment 58, wherein the additional assay includes an additional periostin protein or mRNA assay.

Embodiment 60

The method of embodiment 58, wherein the additional assay includes a different assay.

Embodiment 61

The method of embodiments 9-60, wherein periostin protein or mRNA is detected as part of a differential diagnosis.

Embodiment 62

The method of embodiments 9-61, further including detecting one or more additional indicators of peritoneal injury selected from the group consisting of HSPG degradation, PDGF, leptin, CD68+ macrophage density, and any combination thereof 63. A method of detecting an indicator of peritoneal injury, the method including assaying a biological sample for an indicator of peritoneal injury selected from the group consisting of HSPG degradation, PDGF, leptin, CD68+ macrophage density, and any combination thereof, wherein the biological sample is selected from the group consisting of used peritoneal dialysate, peritoneal fluid, peritoneal tissue, and one or more fractions thereof, and the presence of an indicator at an elevated level indicates the presence and/or degree of peritoneal injury.

Embodiment 64

A method including: assaying a biological sample from a subject for periostin protein or mRNA, wherein the biological sample is selected from the group consisting of a cell collected from used peritoneal dialysate, peritoneal tissue, and one or more fractions thereof, wherein the presence of periostin protein or mRNA at an elevated level indicates the presence and/or degree of peritoneal injury; and prescribing, initiating, and/or altering prophylaxis and/or therapy if the periostin protein or mRNA is elevated.

Embodiment 65

A method including: assaying a biological sample from a subject for periostin protein or mRNA, wherein the biological sample is peritoneal fluid or one or more fractions thereof, wherein the presence of periostin protein or mRNA at an elevated level indicates the presence and/or degree of peritoneal injury; and prescribing, initiating, and/or altering prophylaxis and/or therapy if the periostin protein or mRNA is elevated.

Embodiment 66

The method of embodiments 64 or 65, wherein, when the periostin protein or mRNA level is elevated, a prescription for peritoneal dialysis is changed or peritoneal dialysis is terminated.

Embodiment 67

The method of any of embodiments 64-66, wherein the prophylaxis and/or therapy includes the method of any of embodiments 1, and 4-8.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A-C. Renal periostin increases after 5/6Nx in rats. (A) Periostin mRNA expression increased over time after 5/6Nx in RK compared to control kidney tissue in samples in which the infarct tissue was excised. The expression of 18 S was used as an internal control. (B) Immunoblotting analysis for periostin was also increased in RK compared to control kidneys. (C) Periostin immunostaining was not detected in cortical control rat kidney (C1). In contrast, representative sections of kidney tissues at 2 days, 2 weeks, and 4 weeks displayed cytoplasmic staining for periostin, most prominently in the apical portion of tubular cells, with stronger and more diffuse tubular cell staining at 2 and 4 weeks. There also was periostin staining in casts and/or in sloughed cells in the tubular lumina (C3, C4, arrows). There was no glomerular staining for periostin (C3) (C1-4 Original magnification: 400×). (C5) Renal tubules demonstrated apical periostin in the 2 week RK. Tubules contained luminal sloughed cells and cellular debris which stained strongly for periostin (arrows) (Original magnification: 600×). (C6) 4 week RK had periostin positive interstitial cells (arrows) which frequently were in the periadventitial area around arteries and arterioles. (Original magnification: 400×). * P<0.05 vs. control group, # P<0.05 vs. 2 days after 5/6Nx group.

FIG. 7A-C. Renal periostin expression increased after diabetes induction and UUO in mice. (A) Renal periostin mRNA expression increased after 2 months of SZ injection in DBA2J mice compared to control kidneys. The expression of 18 S was used as an internal control.* P<0.05 vs. control. (B) Renal periostin protein was increased in SZ-DM DBA2J mice compared to control DBA2J mice at 8 week and 16 weeks. * P<0.05 vs. DBA2J mice control kidneys 8 weeks, #P<0.05 vs. DBA2J mice control kidneys 16 weeks. (C) Representative micrographs showed positive periostin immunostaining in renal tubules of SZ-DM at 2 months and UUO at 5 days and 14 days. (Original magnification: 200×).

FIG. 8A-F. Periostin localizes exclusively to tubular cells of the distal nephron after 5/6Nx. Paraffin-embedded sections were double labeled with antibodies against periostin (red, A, D) and either distal nephron marker PNA lectin (green, B) or proximal nephron marker PHA-E lectin (green, E). Periostin co-localized with PNA staining exclusively in the distal nephron (C), but never with PHA-E staining in the proximal nephron (F). Merged images show periostin in red and PNA or PHA-E in green (Original magnification: 200×). Cell nuclei were stained with DAPI (C and F).

FIG. 12A-C. Urine periostin ELISA has high performance in diagnosing CKD and it correlates with decline of GFR and increment of urine NGAL. (A) Urine periostin/creatinine measured by ELISA is higher in patients with progressive proteinuric renal disease (n=21) and in PKD (n=5) than in healthy controls (n=20). Individual values for each patient and control represents the average of at least triplicate testing. The median values for patients with progressive proteinuric disease (2473.58 pg/mg), and PKD (9504.94 pg/mg) were not significantly different from each other, but were significantly higher than for healthy controls (0 pg/mg). (B) Univariate baseline statistical correlations (Sperman coefficient) of urinary periostin. Significant correlations were evidenced with estimated GFR (B1), serum creatinine (B2), and urinary NGAL (B4). (C) Receiver operating characteristics curves of urinary periostin and NGAL considering CKD as status variable. The area under the curve for urinary periostin and NGAL was 0.96 (95% CI, 0.91 to 1.02) and 0.86 (95% CI, 0.75 to 0.97), respectively. Both urinary periostin and NGAL areas were statistically different with respect to that of diagnostic reference line (P<0.001). On the contrary, the difference between the two biomarker areas was non-significant (P=0.09).

FIG. 13A-D. Urine periostin is measurable before a rise in serum creatinine is discernible in renal tissue from a patient with LN in which tubular atrophy is present. (A) Renal biopsy showing proliferative lupus glomerulonephritis with an area of established tubular atrophy (arrow) (Jones stain, Original magnification: ×200). (B) Immunoblotting demonstrating 90 kDa urine periostin in lightly centrifuged urine, but none in control. (C) Periostin immunostaining (brown; H&E counterstain, Original magnification: ×200) shows cytoplasmic tubular cell expression including expression in sloughed luminal cell fragment (arrow). (D) Tubular cells with heavy diffuse cytoplasmic periostin immunostaining (arrow) (Original magnification: ×400).

DETAILED DESCRIPTION

I. Definitions

Figure 1A:
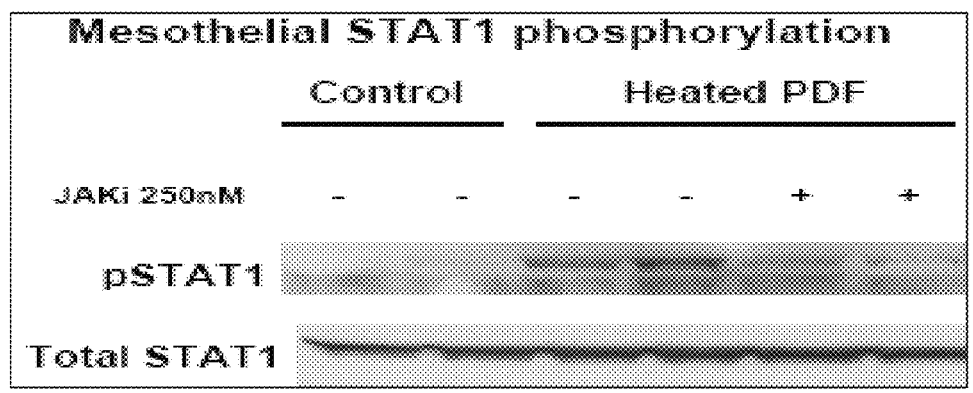
FIG. 1A-B. Mesothelial cell exposure to heated PDF in vitro activates JAK/STAT signaling and induces the STAT-associated protein periostin. (A) STAT 1 and phosphorylated STAT1 (pSTAT); (B) Periostin and GAPDH. The pan-JAKi P6 attenuates activation and the injury signal.

Terms used in the claims and specification are defined as set forth below unless otherwise specified.

As used herein, the term "symptom" refers to any subjective indicator or evidence of an individual's condition.

As used herein, the term "sign" refers to any objective indicator or evidence of an individual's condition.

"Janus Kinase", or "JAK", refers to the members of a family of intracellular, non-receptor tyrosine kinases that transduce cytokine-mediated signals via the JAK-STAT pathway. The terms cover polypeptides that are identified in Genbank by the following designations, as well as polypeptides that are at least about 70% identical to polypeptides identified in Genbank by these designations: JAK1, JAK2, JAK3, TYK2. In alternative embodiments, these terms encompass polypeptides identified in Genbank by these designations and sharing at least about 80, 90, 95, 96, 97, 98, or 99% identity.

"STAT," "Signal Transducer and Activator of Transcription," or "Signal Transduction And Transcription" protein encompass polypeptides that are identified in Genbank by the following designations, as well as polypeptides that are at least about 70% identical to polypeptides identified in Genbank by these designations: STAT1, STAT2, STAT3, STAT4, STAT5 (STAT5A and STAT5B), and sSTAT6. In alternative embodiments, these terms encompass polypeptides identified in Genbank by these designations and sharing at least about 80, 90, 95, 96, 97, 98, or 99% identity.

The "JAK-STAT pathway" refers to a signal transduction pathway that typically includes three main components: (1) a receptor, (2) Janus kinase (JAK), and (3) Signal Transducer and Activator of Transcription (STAT). The receptor is activated by a signal from interferon, interleukin, growth factors, or other chemical messengers. This signal activates the kinase function of JAK, which autophosphorylates itself (phosphate groups act as "on" and "off" switches on proteins). The STAT protein then binds to the phosphorylated receptor, whereupon STAT is phosphorylated by JAK. The phosphorylated STAT protein binds to another phosphorylated STAT protein (dimerizes) and translocates into the cell nucleus. In the nucleus, the STAT protein dimer binds to DNA and promotes transcription of genes responsive to STAT.

An "inhibitor" or "antagonist" of a polypeptide is an agent that reduces, by any mechanism, any polypeptide action, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal functions of the polypeptide. An inhibitor of a polypeptide can be non-selective or selective. Preferred inhibitors (antagonists) are generally small molecules that act directly on, and are selective for, the target polypeptide.

The terms "polypeptide" and "protein" are used interchangeably herein to refer a polymer of amino acids, and unless otherwise limited, include atypical amino acids that can function in a similar manner to naturally occurring amino acids.

The terms "amino acid" or "amino acid residue," include naturally occurring L-amino acids or residues, unless otherwise specifically indicated. The commonly used one- and three-letter abbreviations for amino acids are used herein (Lehninger, A. L. (1975) Biochemistry, 2d ed., pp. 71-92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Exemplary atypical amino acids, include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and His; N-ethylglycine (EtGly) for Gly, Pro, and Ala; N-ethylasparagine (EtAsn), for Asn and Gln; hydroxyllysine (Hyl), for Lys; allohydroxyllysine (Rhyl), for Lys; 3- (and 4-) hydroxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Orn), for Lys, Arg, and His; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

As used herein, the term "complementary" refers to the capacity for precise pairing between two nucleotides. I.e., if a nucleotide at a given position of a nucleic acid molecule is capable of hydrogen bonding with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions.

The phrase "stringent hybridization conditions" generally refers to a temperature about 5° C. lower than the melting temperature ($T_m$) for a specific sequence at a defined ionic strength and pH. Exemplary stringent conditions suitable for achieving specific hybridization of most sequences are a temperature of at least about 60° C. and a salt concentration of about 0.2 molar at pH7.

"Specific hybridization" refers to the binding of a nucleic acid molecule to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The phrases "an effective amount" and "an amount sufficient to" refer to amounts of a biologically active agent that produce an intended biological activity.

As used herein, "an amount sufficient to reduce the subject's risk of peritoneal injury" refers to an amount that has been determined to be likely to reduce risk of peritoneal injury in such subjects. The use of this term does not require that a particular subject's risk of peritoneal injury will be reduced, although this is the expected outcome, and in some embodiments, this outcome is achieved.

As used herein, "an amount sufficient to mitigate the subject's at least one symptom or sign of peritoneal injury" refers to an amount that has been determined to be likely to mitigate (i.e., reduce or eliminate) at least one symptom or sign of peritoneal injury in such subjects. The use of this term does not require that a particular subject's symptom or sign is mitigated, although this is the expected outcome, and in some embodiments, this outcome is achieved.

"Biological samples" that can be assayed using the methods of the present invention include used peritoneal dialysate, peritoneal fluid, peritoneal tissue, or a fraction of any of these (e.g., a liquid or tissue fraction, cell, or protein).

As used herein with reference to periostin, the term "elevated level" refers to a level in a biological sample that is higher than a normal level or range. The normal level or range for periostin is defined in accordance with standard practice. Thus, the level measured in a particular biological sample will be compared with the level or range of levels determined in similar normal samples. In this context, a "normal sample" is a sample from an individual with no detectable peritoneal injury (e.g., a subject not undergoing peritoneal dialysis, with no other indications of, or risk factors for, peritoneal injury). The level of periostin is said to be "elevated" where the periostin is normally undetectable (i.e, the normal level in the tissue is zero), but is detected in a test sample, as well as where the periostin is present in the test sample at a higher than normal level or range. For example, in patients with renal failure, the peritoneum is already injured, even before peritoneal dialysis starts, and there is often some baseline periostin detectable that reflects baseline peritoneal injury from end stage renal disease and possibly from the placement of the peritoneal dialysis catheter. Increments in periostin above the patient's initial baseline reflects that increased risk for peritoneal membrane failure. Accordingly, the term "elevated" also refers to an increase in periostin level in an individual, as compared to an earlier level, for example, a baseline level (e.g., obtained from a sample after placement of a peritoneal dialysis catheter), in that same individual.

As used herein, references to assaying or detecting periostin level are understood as referring to the assay or detection of periostin protein level or periostin mRNA level, unless the context makes it clear that one of these two levels is being discussed.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein, the phrase "periostin protein or mRNA becomes labeled with a detectable label" refers to the binding of a label or labeled moiety to periostin protein or mRNA, directly or indirectly, via one or more additional moieties.

As used with reference to periostin protein or mRNA, a "free state" refers to the state of periostin protein or mRNA before contact with any assay component. This term encompasses periostin bound to one or more sample components. The term "bound state" is used to describe periostin protein or mRNA bound to one or more assay component(s) to form a complex.

The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

As used herein, the term "worn article" refers to any article that can be worn on a subject's body, including, but not limited to, a tag, bracelet, necklace, arm band, or head band.

As used herein, the term "differential diagnosis" refers to the determination of which of two or more diseases with similar symptoms or signs is likely responsible for a subject's symptom(s) or sign(s), based on an analysis of the clinical data.

II. Method of Preventing or Treating Peritoneal Injury or Improving Peritoneal Membrane Function

A. In General

One aspect of the invention provides a method of preventing and/or treating peritoneal injury and/or of diminished peritoneal membrane function by administering an effective amount of an inhibitor of the JAK/STAT pathway to a subject who is at risk of peritoneal injury and/or has at least one symptom or sign of peritoneal injury and/or of diminished peritoneal membrane function. The effective amount is an amount sufficient to reduce the subject's risk of peritoneal injury and/or mitigate the subject's at least one symptom or sign of peritoneal injury and/or to improve peritoneal membrane function. In some embodiments, the inhibitor of the JAK/STAT pathway is an inhibitor of JAK.

The JAK family includes four members of kinases: JAK1, JAK2, JAK3 and TYK2 (Tyrosine Kinase 2). These phosphotyrosine kinases (PTKs) are ubiquitously expressed, except JAK3, which is mainly restricted to hematopoietic cells. JAKs bind to the intracellular side of cytokine and growth hormone-like receptors and transmit signals from the extracellular milieu to the nucleus through a tyrosine phosphorylation signaling mechanism. In particular, activated JAK phosphorylates specific tyrosine residues on the cytoplasmic tails of the receptors. The phosphorylated receptor provides binding sites for the signal transducer and activator of transcription (STAT) proteins that can be phosphorylated by JAK. Phosphorylated STATs form dimers and translocate into the nucleus, where they induce gene transcription.

The PTK domain (JH1) of JAKs contains the functional kinase site, while the adjacent pseudokinase domain (JH2) acts as an auto-inhibitor of the kinase domain. JAKs play a crucial role in the pathogenesis of numerous cellular malignancies and immunological disorders. JAK-STAT signals are negatively regulated by the suppressors of cytokine signaling (SOCS).

Constitutive or enhanced JAK kinase activity was described in abnormal cell proliferation in a series of hematologic neoplasias, such as lymphoid and myeloid leukemias, Hodgkin's lymphoma and B-cell non-Hodgkin's lymphomas. JAK family kinases play essential and specific roles in immune cell development and function. For instance, JAK2 gain-of-function mutations (V617F) underlie a subset of disorders collectively referred to as myeloproliferative diseases. Mutations of JAK3 underlie severe combined immunodeficiency, indicative of its critical role in the development and function of lymphocytes. Mutations of TYK2 cause autosomal recessive hyperIgE syndrome.

Definitive evidence of JAK's relation to peritoneal injury is, for the first time, described herein. Accordingly, methods of preventing and/or treating peritoneal injury by administering modulators of JAK/STAT pathway are described herein. Some embodiments of the invention relate to the use of JAK inhibitors for this purpose.

In some embodiments, the method entails inhibiting one or more JAKs including JAK1, JAK2, JAK3, or TYK2 in a subject, whereby a symptom or sign of peritoneal injury is reduced or prevented. Generally, the method is carried out by administering an effective amount of a JAK inhibitor to a subject at risk of, or having one or more symptom(s) or sign(s) of, peritoneal injury(ies). Subjects who are at risk of peritoneal injury include those with chronic kidney disease and those undergoing peritoneal dialysis, e.g., those exposed to peritoneal dialysate, those who have or had peritonitis, and/or those who are identified as being at risk using any of the methods described herein. Exemplary risk factors for peritoneal injury include peritoneal barrier (Pbarrier) exposure to lactate, low dialysate pH (e.g., ≤5.5, as in most peritoneal dialysis solutions currently available in the United States), high glucose content (e.g., 1.5%, 2.5%, or 4.25%), advanced glycation endproducts (AGE), glucose-degradation products (GDP) generated from peritoneal dialysis fluid (PDF) heat sterilization, inflammatory foreign-body response to the catheter, uremia, and peritonitis. Any subject with one or more of these risk factors is a candidate for the treatment methods described herein.

In some embodiments, symptoms and signs of peritoneal injury reflect the inability of the membrane to continue to serve as an adequate dialyzer for the patient. Symptoms are those of uremia, including, but not limited to, poor appetite, weight loss, fatigue, lethargy, sleep disturbances, nausea, vomiting, shortness of breath, body swelling, and hypertension. This may be reflected, in peritoneal fluid and tissue, by elevated soluble and cellular inflammatory factors, increased chemokine, cytokine, and growth factors in abdominal tissue and fluid, milky spots of the Pbarrier, elevated level of mononuclear leukocytes in the Pbarrier and PDF, reduced Pbarrier glycocalyx, impaired UF capacity and solute transport in PD, worsened PET measurements, elevated mesothelial to mesenchymal transition, submesothelial expansion, proliferation of fibroblasts, lymphangiogenesis, neovascularization, hyalinized and narrowed vessels, and functional Pbarrier failure. As described below, elevated periostin is an indicator of peritoneal injury, as are other markers of JAK/STAT pathway activation, and any of these can be employed to identify suitable candidates for the treatment methods described herein. For detecting diminished peritoneal membrane function, PET measurements are most typically employed, with high normal and high measurements indicating that treatment with an inhibitor of the JAK/STAT pathway may improve peritoneal membrane function.

The subject of the method can be any individual that expresses JAK. Examples of suitable subjects include mammals, such as research animals, e.g., mice, rats, guinea pigs, rabbits, cats, dogs, as well as monkeys and other primates, and humans. The subject can be an individual who is regularly, or intermittently, having one or more symptoms or signs of peritoneal injury or diminished peritoneal function or an individual who is at risk for such injury or diminished function.

The method of the invention entails inhibiting JAK to a degree sufficient to reduce or prevent one or more symptom(s) or sign(s) of peritoneal injury and/or to improve peritoneal membrane function. Improvements in peritoneal membrane function are conveniently determined using PET measurements. In various embodiments, JAK is inhibited by at least about 10, 20, 30, 40, 50, 60, 70, 80, 90, and 95 percent, as determined by any suitable measure of JAK inhibition (such as, for example, any conventional essays or the assays described herein). In certain embodiments, JAK inhibition results permits the peritoneum to function in its capacity to clear solutes from plasma and to ultrafilter fluid.

One aspect of the invention relates to a method for identifying a subject as a candidate for prevention and/or treatment of peritoneal injury and/or treatment of peritoneal injury uses one or more JAK inhibitors. The subject can be identified by any of the parameters discussed above, but in certain embodiments, the method entails assaying a biological sample for a marker of JAK/STAT pathway activation, such as periostin protein or mRNA. Markers of JAK/STAT pathway activation, including periostin, provide early indications of peritoneal injury, e.g., prior to detectable loss of peritoneal membrane function, whereas PET measurements, for example, provide an indication of diminished or altered peritoneal membrane function. Suitable biological samples include, e.g., used peritoneal dialysate, peritoneal fluid, peritoneal tissue, or a fraction of any of these (e.g., a liquid or tissue fraction, cell, or protein). In particular embodiments, the subject is identified as a candidate for the prevention and/or treatment of peritoneal injury if periostin protein or mRNA is present in the biological sample at an elevated level. The presence of periostin protein or mRNA at an elevated level, as compared to a normal level and/or as compared to the level in an earlier-obtained sample from the same subject (e.g., a baseline level), indicates the presence and/or degree of peritoneal injury.

Another aspect of the invention relates to a method of treating peritoneal injury and/or diminished peritoneal membrane function in a particular subject, namely one who is identified as a candidate for such treatment. The subject can be identified by any of the parameters discussed above, but in certain embodiments, the method includes the step of assaying a biological sample from a subject for periostin protein or mRNA, wherein the biological sample is any of those described above. The presence of periostin protein or mRNA at an elevated level, as compared to a normal level and/or as compared to the level in an earlier-obtained sample from the same subject (e.g., a baseline level), indicates the presence and/or degree of peritoneal injury. The method also includes the step of prescribing, initiating, and/or altering prophylaxis and/or therapy if the periostin protein or mRNA is elevated. In some embodiments of the invention, the prophylaxis and/or therapy includes any of the methods described herein. In other embodiments, the method includes changing the peritoneal dialysis prescription or terminating peritoneal dialysis.

B. JAK Inhibitors

Any kind of JAK inhibitor that is tolerated by the subject can be employed in the methods described herein. Thus, the inhibitor can be a polypeptide (such as, e.g., an anti-JAK antibody), a polynucleotide (e.g., one that encodes an inhibitory polypeptide), or a small molecule. In particular embodiments, when the inhibitor is a polynucleotide-encoded inhibitory polypeptide, the polynucleotide is introduced into the subject's cells, where the encoded polypeptide is expressed in an amount sufficient to inhibit JAK.

Inhibition of JAK can be achieved by any available means, e.g., by modulating: (1) the expression, mRNA stability, protein trafficking, modification (e.g., phosphorylation), or degradation of JAK, or (2) one or more of the normal functions of JAK.

In certain embodiments, the JAK inhibitor can be, e.g., a peptide or a small molecule. In other embodiments, JAK inhibition is achieved by reducing the level of JAK polypeptides in the cells or inhibiting JAK function by various means that entail introducing polynucleotide inhibitors into cells. JAK levels can be reduced using, e.g., antisense, catalytic RNA/DNA, RNA interference ($RNA_i$), or "knock-out" techniques. JAK expression/function can also be inhibited using intrabodies.

In some embodiments, the JAK inhibitors are non-selective for JAKs. In other embodiments, the JAK inhibitors are selective for JAKs. Some embodiments of the invention use antagonists that are selective for all JAKs, namely pan-JAK inhibitors. An exemplary pan-JAK inhibitor is P6. Other embodiments of the invention use antagonists that are selective for one or some of JAK1, JAK2, JAK3 and TYK2, namely narrow spectrum JAK inhibitors. An exemplary narrow spectrum JAK inhibitor is JAK 1/2 inhibitor LSN 3103801 (Lilly Pharmaceuticals).

In some embodiments of the invention, the inhibitors of JAK include Baricitinib (LY3009104, INCB28050), Lestaurinib, Pacritinib (SB1518), Ruxolitinib, and Tofacitinib (tasocitinib; CP-690,550).

In some embodiments of the invention, the inhibitors of JAK include AC-430, AG490, AUH-6-96, AZ-01, AZ-60, AZ960, BMS-911543, CEP-701, CEP-33779, CMP6, CP-690,550, CP-352,664, CYT387, GLPG-0634, JAK2-IA, INCB20, INCB18424, INCB028050, LS104, narrow-spectrum JAK1/2 inhibitor LSN 3103801, pan-JAK inhibitor P6, PS-608504, PS-020613, Pyridone 6, R-348, R-732, SB1518, TG101209, TG101348, WHI-PI 54, WP1066, and XL-019.

In some embodiments of the invention, the inhibitors of JAK include ortho-substituted pyrimidine compounds, imidazopyridine derivatives, heterocyclyl pyrazolopyrimidine analogues, and pyrrolo[2,3-d]pyrimidine urea compounds.

More specifically, in some embodiments, the JAK inhibitors for the invention are selective JAK1 inhibitors. Examples of selective JAK1 inhibitors are described in Norman (2012), Selective JAK1 inhibitor and selective TYK2 inhibitor patents, Expert Opinion on Therapeutic Patents, 22(10): 1233-49, (incorporated by reference herein for its description of JAK inhibitors). Examples of JAK1 inhibitors include but are not limited to: Tricylic JAK1 inhibitors by Roche in WO-2011086053; tricyclic JAK1 inhibitors by Abbott in WO-2009152133 and WO-2011068881; JAK1 inhibitors by Incyte in WO-2010135650; JAK1 inhibitors claimed by Incyte in WO-2011112662; and Anilinophthalazine-based JAK1 inhibitors by Exelixis in WO-2012037132.

In other embodiments, the JAK inhibitors suitable for the current invention are selective JAK2 inhibitors. Examples of selective JAK2 inhibitors are described in Kiss, Sayeski and Keseru (2010) Recent developments on JAK2 inhibitors: a patent review, Expert Opinion on Therapeutic Patents, 20(4): 471-495 (incorporated by reference herein for its description of JAK inhibitors), and Dymock and See (2013), Inhibitors of JAK2 and JAK3: an update on the patent literature 2010-2012, Expert Opinion on Therapeutic Patents, early online publication (doi:10.1517/13543776.2013.765862) (incorporated by reference herein for its description of JAK inhibitors).

Examples of selective JAK2 inhibitors include but are not limited to: Isoquinolines by Ambit in WO2012030944 (incorporated by reference herein for its description of JAK inhibitors); Pyrrolo[2,3-d]pyrimidines and quinazolines by Ambit in WO2012030924, WO2012030914, WO2012030912, WO2012030910, and WO2010099379 (each of which is incorporated by reference herein for its description of JAK inhibitors); Thieno[2,3-d]pyrimidines and pyrrolo[1,2-f][1,2,4]triazines by Ambit in WO2012030894 and WO2010002472 (each of which is incorporated by reference herein for its description of JAK inhibitors); Imidazo[2,3-c]pyridines by Array BioPharma in WO2011130146 (incorporated by reference herein for its description of JAK inhibitors); Diaminopyrimidines and pyridines by AstraZeneca in WO2010038060 and WO2010020810 (each of which is incorporated by reference herein for its description of JAK inhibitors); Imidazo[4,5-c]pyrrolo[2,3-b]pyridines by Bristol Meyers Squibb in WO2011028864 (incorporated by reference herein for its description of JAK inhibitors); [1,2,4]triazolo[1,5-a]pyridine derivatives by Cephalon in WO2010141796 (incorporated by reference herein for its description of JAK inhibitors); Pyrrolo[1,2-f][1,2,4]triazines by Cephalon in WO2010071885 (incorporated by reference herein for its description of JAK inhibitors); Diphenylpyrrolo[1,2-f][1,2,4]triazin-2-amines by Cephalon in WO2010071885 (incorporated by reference herein for its description of JAK inhibitors); 7,8-Dihydropyrido[4,3-d]pyrimidin-5(6H)-ones by Debiopharm-Aurigene in WO2011101806 (incorporated by reference herein for its description of JAK inhibitors);

single amino pyrazole clinical candidate 'LY2784544' by Eli Lilly in US20100152181; Triazolo[1,5-a]pyridines by Galapagos in WO2010010190 and WO2010010189 (each of which is incorporated by reference herein for its description of JAK inhibitors); Triazolo[1,5-a]pyridines by Galapagos in WO2010010188, WO2010010187, WO2010010186 and WO2010010184 (each of which is incorporated by reference herein for its description of JAK inhibitors); Pyrazolo[1,5-a]pyrimidines by Genentech in WO2010051549 (incorporated by reference herein for its description of JAK inhibitors); Pyrazolo[1,5-a]pyrimidines by Genentech in WO2011003065 (incorporated by reference herein for its description of JAK inhibitors); Pyrrolo[2,3-d]pyrimidines by Hutchison MediPharma in WO2012022045 and WO2012022265 (each of which is incorporated by reference herein for its description of JAK inhibitors); Pyrrolo[2,3-d]

pyrimidines by Incyte in WO2012068440 and WO2011028685 (each of which is incorporated by reference herein for its description of JAK inhibitors); Pyrrolo[2,3-d]pyrimidines and other series by Incyte WO2010135621 and WO2010039939; Ruxolitinib analogues, formulations and metabolites by Incyte in WO2012068450, WO2011103423 and WO2011044481 (each of which is incorporated by reference herein for its description of JAK inhibitors); Macrocyclic diaminopyrimidines by Incyte in WO2010085597 (incorporated by reference herein for its description of JAK inhibitors); Pyrazoles and thiazoles by Merck in WO2010014453 and WO2010011375 and indazoles by Nerviano Medical Sciences in WO2010069966 (incorporated by reference herein for its description of JAK inhibitors); Pyrrolo[2,3-d]pyrimidines by Pfizer in WO2011097087 WO2011075334, WO2011045702 and WO2010020905 (each of which is incorporated by reference herein for its description of JAK inhibitors); Diaminopyrimidines by Rigel in WO2010039518, WO2010085684 and WO2010075558 (each of which is incorporated by reference herein for its description of JAK inhibitors); compounds by TargeGen and University of Florida Research Foundation in WO2010068710 (incorporated by reference herein for its description of JAK inhibitors).

In some embodiments, the JAK inhibitors suitable for the current invention are selective JAK3 inhibitors. Examples of selective JAK3 inhibitors are described in Wilson (2010) Recent patents in the discovery of small molecule inhibitors of JAK3, Expert Opinion on Therapeutic Patents, 20(5):609-23, (incorporated by reference herein for its description of JAK inhibitors) and Dymock and See (2013).

Examples of selective JAK3 inhibitors include but are not limited to: heterocycles by Biocryst in WO2011031554, WO2011014817 and WO2011150356 (each of which is incorporated by reference herein for its description of JAK inhibitors); Furan[2,3-d]pyrimidines by Biocryst in WO2011079230 (incorporated by reference herein for its description of JAK inhibitors); pyrrolo[1,2-b]pyridazine by Bristol Meyers Squibb in WO2012125887 (incorporated by reference herein for its description of JAK inhibitors); Pyrazolo[3,4-d]pyrimidines by Cellzome in WO2012022681, WO2011134831, WO2011048082, and WO2011048082 (each of which is incorporated by reference herein for its description of JAK inhibitors); Diaminopyrimidines by Cellzome in WO2011029807 (incorporated by reference herein for its description of JAK inhibitors); Pyrrolo[2,3-b]pyridines by Dainippon Sumitomo Pharma in JP2012012332; Diamino-pyridine-3-carboxyamides by Kowa Co. in WO2010061971 (incorporated by reference herein for its description of JAK inhibitors); Diamino-amido-pyrimidines by Portola in WO2010129802 (incorporated by reference herein for its description of JAK inhibitors); Diamino-pyridines by Portola in US20120108566; Diamino-pyrimidines by Rigel in WO2012015972 (incorporated by reference herein for its description of JAK inhibitors); Pyrrolo[2,3-b]pyrazines by Roche in WO2011144584 and WO2011144585 (each of which is incorporated by reference herein for its description of JAK inhibitors); Pyrrolo[2,3-b]pyrazines, diaminopyridines and macrocyclic compounds by Roche in WO2010063634, WO2010142752 and WO2011033053 (each of which is incorporated by reference herein for its description of JAK inhibitors); Tricyclic naphthyridinones by Takeda in WO2010144486 (incorporated by reference herein for its description of JAK inhibitors).

In some embodiments, the JAK inhibitors are JAK2/3 inhibitors, examples of which include but are not limited to: 3H-pyrrolo[3,2-f][1,7]naphthyridines by Advinus in WO2012127506 (incorporated by reference herein for its description of JAK inhibitors); Various heterocycles by Almirall in WO2012069202, WO2011101161 and WO2011076419 (each of which is incorporated by reference herein for its description of JAK inhibitors); Purin-8-ones and derivatives by Almirall in WO2011157397 (incorporated by reference herein for its description of JAK inhibitors); Bipyridyl benzamides by Almirall in WO2012041476 (incorporated by reference herein for its description of JAK inhibitors); Tricyclic Pyrrolopyrrolopyridines by Astellas in WO2010119875 (incorporated by reference herein for its description of JAK inhibitors); Pyrrolo[2,3-d]pyrimidines by Japan Tobacco in WO2011013785 and macrocyclic anilinopyrrolo[2,3-d]pyrimidines by Jiangsu Simcere in CN102617599 (incorporated by reference herein for its description of JAK inhibitors); Pyrrolo[2,3-d]pyrimidines and pyrrolo[2,3-b]pyridines by Leo Pharma in WO2012003829 and WO2011003418 (each of which is incorporated by reference herein for its description of JAK inhibitors); Pyrrolo[2,3-d]pyrimidines and pyrrolo[2,3-b]pyridines by Merck in WO2012054364 and WO2011137022 (each of which is incorporated by reference herein for its description of JAK inhibitors); and Imidazo[4,5-d]pyridines and pyrazolo[2,3-a]pyridines by Palau Pharma in WO2011051452 and WO2010072823 (each of which is incorporated by reference herein for its description of JAK inhibitors).

In other embodiments, the JAK inhibitors are selective TYK2 inhibitors. Examples of selective TYK2 inhibitors are described in Norman (2012). Examples of selective TYK2 inhibitors include but are not limited to: TYK2 inhibitors by Bayer in DE-102009015070A1; TYK2 inhibitor by Roche in WO-2011113802, WO-2012035039 WO-2012066061, WO-2011113802, WO-2012035039 and WO-2012066061 (each of which is incorporated by reference herein for its description of JAK inhibitors); Triazolopyridine TYK2 inhibitors by Cellzome in WO-2012000970 (incorporated by reference herein for its description of JAK inhibitors); and Monocyclic TYK2 inhibitors by Cellzome in WO-2012062704 (incorporated by reference herein for its description of JAK inhibitors).

In various embodiments, one or more JAK inhibitors, including any of those described above can be combined, i.e., administered simultaneously or sequentially, in the same or different compositions.

C. Compositions

For research and therapeutic applications, a JAK/STAT pathway inhibitor, such as a JAK inhibitor, is generally formulated to deliver inhibitor to a target site in an amount sufficient to inhibit the targeted JAK/STAT pathway protein at that site.

In some embodiments, a JAK inhibitor is present in a pharmaceutical formulation in an amount sufficient to inhibit a Janus kinase activity at the intended site of action of one or more of JAK1, JAK2, JAK3 and TYK2, and a pharmaceutically acceptable carrier.

Inhibitor compositions of the invention optionally contain other components, including, for example, a storage solution, such as a suitable buffer, e.g., a physiological buffer. In a preferred embodiment, the composition is a pharmaceutical composition and the other component is a pharmaceutically acceptable carrier, such as are described in Remington's Pharmaceutical Sciences (1980) 16th editions, Osol, ed., 1980.

A pharmaceutically acceptable carrier suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

In some embodiments of the invention, formulations of a JAK inhibitor suitable for oral administration are prepared as discrete units such as pills, capsules, cachets or tablets each containing a predetermined amount of the a JAK inhibitor. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a JAK inhibitor intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments of the invention, aqueous suspensions of a JAK inhibitor contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

In some embodiments of the invention, the pharmaceutical composition of a JAK inhibitor is in the form of a sterile injectable preparation, such as a sterile injectable aqueous or oleaginous suspension. This suspension may be formulated according to the known art using suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments of the invention, formulations for rectal administration may be presented as a suppository with a suitable base comprising for example cocoa butter or a salicylate.

In some embodiments of the invention, formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods.

Some embodiments include sustained-release pharmaceutical compositions. An exemplary sustained-release composition has a semipermeable matrix of a solid hydrophobic polymer to which the inhibitor is attached or in which the inhibitor is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(+3-hydroxybutyric acid. Such matrices are typically in the form of shaped articles, such as films, or microcapsules.

In another embodiment, a sustained-release composition includes a liposomally entrapped inhibitor. Liposomes are small vesicles composed of various types of lipids, phospholipids, and/or surfactants. These components are typically arranged in a bilayer formation, similar to the lipid arrangement of biological membranes. Liposomes containing inhibitors are prepared by known methods, such as, for example, those described in Epstein, et al. (1985) PNAS USA 82:3688-92, and Hwang, et al., (1980) PNAS USA, 77:4030-34. Ordinarily the liposomes in such preparations are of the small (about 200-800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid composition including, for example, phosphatidylcholine, cholesterol, and PEG-derivatized phosphatidylethanolamine (PEG-PE). If desired, liposomes are extruded through filters of defined pore size to yield liposomes of a particular diameter.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Pharmaceutical compositions of the invention can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient.

D. Administration

Pharmaceutical compositions according to the invention are generally administered systemically. Methods for systemic administration do not differ from known methods for administering small-molecule drugs or therapeutic polypeptides, peptides, or polynucleotides them. Suitable routes of administration include, for example, oral, intraperitoneal, intravenous, intraarterial, intraventricular, intramuscular, intrarectal, nasal, intrapulmonary, topical, or intralesional routes. Pharmaceutical compositions of the invention can be administered continuously by infusion, by bolus injection, or, where the compositions are sustained-release preparations, by methods appropriate for the particular preparation. For patients undergoing peritoneal dialysis, a JAK/STAT pathway inhibitor or a formulation containing the inhibitor is conveniently added to the peritoneal dialysis solution.

E. Dose

The dose of inhibitor is sufficient to inhibit the JAK, preferably without significant toxicity. In particular in vivo embodiments, the amount of JAK inhibitor is sufficient to mitigate a symptom or sign of peritoneal injury and/or improve peritoneal membrane function in a subject. For in vivo applications, the dose of inhibitor depends, for example, upon the therapeutic objectives, the route of administration, the specific JAK inhibitor(s), and the condition of the subject, among other factors. Accordingly, it is necessary for the clinician to titer the dosage and modify the route of administration as required to obtain the optimal therapeutic effect. Generally, the clinician begins with a low dose and increases the dosage until the desired therapeutic effect is achieved. Starting doses for a given inhibitor can be extrapolated from in vitro and/or animal data.

In some embodiments, an orally administered dose of JAK inhibitor(s) to treat human patients for peritoneal injury and/or to improve peritoneal membrane function may range from about 10 mg to about 1000 mg of the inhibitor(s). A typical dose may be about 100 mg to about 300 mg. Thus, in various embodiments, an oral dose may contain 10, 50, 100, 125, 150, 175, 200, 225, 250, 275, 300, 350, 400, 450, 500, 550, 600, 650, 700, 750, 800, 850, 900, 950, or 1000 mg of JAK inhibitor(s) or any amount that falls within any ranged bounded by any of these values. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

In other embodiments, the initial pharmaceutically effective amount of the JAK inhibitor administered per dose will be in the range of about 0.01-100 mg/kg, e.g., about 0.1 to 20 mg/kg of patient body weight per day, with an illustrative initial range of compound used being 0.3 to 15 mg/kg/day. In various embodiments, the intraperitoneal dose can be 0.01, 0.05, 0.1, 0.2, 0.3, 0.4, 0.5, 0.6, 0.7, 0.8, 1.0, 2.0, 3.0, 4.0, 5.0, 6.0, 7.0, 8.0, 9.0, 10, 11, 12, 13, 14, 15, 16, 17, 18, 19, 20, 25, 50, 75, or 100 mg/kg or any amount that falls within any ranged bounded by any of these values.

III. Method of Detecting an Indicator of Peritoneal Injury

A. In General

The work described herein shows that periostin mRNA is found in cells pelleted from the peritoneal dialysate of patients on peritoneal dialysis. Higher levels are found in long-term peritoneal dialysis patients compared to new patients, suggesting incremental injury with time from dialysate exposure. These data are consistent with data derived from work with the periostin molecule in kidney, in which periostin was a marker of kidney injury. [Satirapoj B, Wang Y, Chamberlin M P, Dai T, LaPage J, Phillips L, Nast C C, and Adler S G: Periostin: Novel tissue and urinary biomarker of progressive renal injury indicative of distal nephron tubular epithelial mesenchymal transition. Nephrol. Dial. Transplant. (2012) 27 (7): 2702-2711] In kidney, urine measurements of periostin are useful in diagnosing acute kidney injury as well as ongoing chronic kidney injury, potentially obviating the need for a kidney biopsy in some clinical situations. Furthermore, this biomarker is unique in that it has the capability of noninvasively assessing, in a quantitative manner, a particular pathophysiologic process (e.g., epithelial mesenchymal transformation (EMT)) that is a major driver of progressive renal injury. Measurement of periostin in urine provides a surrogate measure of EMT, and therefore a valuable tool for assessing the success of treatments for kidney diseases. See Examples below and co-pending U.S. Ser. No. 12/924,608, filed Sep. 29, 2010 (U.S. Patent Publication No. 20110177613, published on Jul. 21, 2011), which is incorporated herein by reference for its description of periostin as a biomarker.

Based on these observations in kidney, and unpublished data that in peritoneal dialysate from patients, periostin is a biomarker for peritoneal membrane ultrafiltration injury and/or failure, which may result in either high transporter PET status and/or EPS. Infection and/or components of the prescribed peritoneal dialysate injure the peritoneum. This injury is first manifested by the induction of periostin in the peritoneal mesothelial cell layer, in a manner analagous to the induction of periostin in renal epithelial cells during injury. Similar to the observed process of EMT in renal epithelial cells, the de novo expression of periostin in mesothelial cells induces mesothelial to mesenchymal transition (MMT). This expression induces alters the function of mesothelial cells and induces them to secrete inflammatory proteins and extracellular matrix. In addition, some of these cells may translocate into the peritoneal dialysate itself, where cells are available for collection and assay. Others may interact with submesothelial fibroblasts, inducing them to increase ECM, thereby contributing to the induction of peritoneal fibrosis. Interactions of periostin with TGFbeta and integrins occur. In this location, periostin is also posited to support the vascularization of the peritoneal membrane, through a VEGF2R-supported process. Thus, periostin plays a role in all of the features that lead to a failed peritoneal membrane in high transporter PET conditions and in EPS, including loss of the mesothelial layer, transformation of mesothelial cells to mesenchymal cells, increased mesenchymal secretion of periostin leading to a thickened and scarred peritoneal membrane, and hypervascularization of the peritoneal membrane.

In abstract FR-P01730, presented at the meeting of the American Society of Nephrology on Friday, Nov. 11, 2011 as a poster, Braun et al. report:

Periostin was found in the walls of large arteries and focally in the submesothelial zone in control biopsies. In encapsulating peritoneal sclerosis (EPS), there was a very prominent expression of the sclerosis layer. Commonly, the superficial layer was periostin negative. A semiquantitative score was most prominently associated with the diagnosis of EPS, as well as with the thickness of the submesothelial sclerosis zone.

A major area of research in patients with chronic kidney disease is the elucidation of epithelial to mesenchymal transition EMT during renal fibrosis and tissue scarring. During this process, various proteins involved in cell structure and ECM synthesis are differentially regulated, transforming the tubule phenotype. Overexpression of periostin in a tumorigenic but non-metastatic epithelial cell line (293T) induced fibroblast-like transformation with increased expression of vimentin, epidermal growth factor receptor (EGFR), MMP9, and evidence for increased cell migration, invasion, and adhesion, all consistent with EMT. The data demonstrating periostin expression in injured tubule cells, and in tubules being shed into the lumen are consistent with the likelihood that in damaged kidneys and in urine, renal tubule periostin expression is a marker of EMT. When inventors overexpressed periostin in vitro in cultured renal tubule cells, the cells lost the tubule differentiation marker E-cadherin, and expressed mesenchymal (eg fibroblast) markers FSP1 and MMP9, indicating the loss of tubule differentiation and the adoption of the mesenchymal state. The data in peritoneal dialysate indicate that a similar phenomenon, mesothelial to mesenchymal transition (MMT) occurs in injured peritoneal membranes and that it is stimulated in part or in whole by the de novo expression of periostin in mesothelial cells induced by aspects of PD therapy. Therefore, periostin mRNA and/or protein measurement in cells collected from PD solutions, from used dialysate, and/or from peritoneal tissue serves as a useful biomarker of early peritoneal membrane injury, the progression of that injury, and the regression of that injury with changes in prescription (e.g., in dialysate composition).

Currently, peritoneal injury in PD patients is diagnosed by demonstrating membrane failure by the PET test. This is a marker that measures peritoneal membrane functional loss, but not peritoneal cellular and membrane injury with consequent restructuring of the entire membrane. A periostin protein or mRNA assay, e.g, using spent dialysate, can measure peritoneal injury per se in a non-invasive manner. Further, such an assay can detect a very specific form of peritoneal injury, e.g., MMT.

In certain embodiments, the invention provides methods of detecting periostin as a novel biomarker of peritoneal injury. These methods entail assaying a biological sample for periostin, wherein the level of periostin is positively correlated with peritoneal injury. In various embodiments, these methods are useful in diagnosing acute peritoneal injury as well as ongoing peritoneal injury. In other embodiments, these methods can be employed to assess response to therapy and/or identify relapse of peritoneal injury. Furthermore, these methods are unique in that they have the capability of non-invasively assessing, in a quantitative manner, a particular pathophysiologic process (e.g., mesothelial to mesnchymal transformation (MMT)), which may be a major driver of progressive peritoneal injury. Measurement of periostin in a biological sample described herein provides a surrogate measure of MMT and therefore a valuable tool for assessing the status of peritoneal injury.

One aspect of the invention relates to a method of detecting an indicator of peritoneal injury. The method entails assaying a biological sample for periostin protein or mRNA. Suitable biological samples include used peritoneal dialysate, peritoneal fluid, peritoneal tissue, or a fraction of any of these (e.g., a liquid or tissue fraction, cell, or protein). The presence of periostin protein or mRNA at an elevated level indicates the presence and/or degree of peritoneal injury.

Another aspect of the invention relates to using periostin as an indicator of progression, remission, or relapse of peritoneal injury.

In some embodiments, the invention relates to a method for identifying a subject as a candidate for prevention and/or treatment of peritoneal injury. The method includes assaying a biological sample for periostin protein or mRNA. Any of the biological samples discussed above can be employed in the method. The method also includes identifying the subject as a candidate for the prevention and/or treatment of peritoneal injury if periostin protein or mRNA is present in the biological sample at an elevated level.

In other embodiments, the invention provides a method for detecting an indicator of a subject's response to treatment for peritoneal injury. After initiation of treatment for peritoneal injury, the method includes assaying a biological sample obtained from a subject for periostin protein or mRNA. According to the method, the level of periostin protein or mRNA is positively correlated with the degree of peritoneal injury.

In some embodiments of the invention, in addition to, or instead of, detecting periostin, the method of detecting an indicator of peritoneal injury includes detecting one or more indicators selected from the group consisting of HSPG degradation, PDGF, leptin, CD68+ macrophage density, and any combination thereof. In some embodiments, the indicators are assayed from a biological sample selected from used peritoneal dialysate, peritoneal fluid, peritoneal tissue, or a fraction of any of these (e.g., a liquid or tissue fraction, cell, or protein). The presence of an indicator at an elevated level indicates the presence and/or degree of peritoneal injury.

B. Sample Collection and Processing

The assay methods of the invention are generally carried out on biological samples derived from an animal, preferably a mammal, and more preferably a human.

The methods of the invention can be carried out using any sample that may contain periostin mRNA, soluble periostin, periostin in exosomes, or periostin moieties, including its intracellular, transmembrane, or extracellular moieties or any peptide fraction thereof. Convenient samples include, for example, used peritoneal dialysate, peritoneal fluid, peritoneal tissue, or a fraction of any of these (e.g., a liquid or tissue fraction, cell, or protein).

The sample may be pretreated as necessary by dilution in an appropriate buffer solution or concentrated, if desired. Any of a number of standard aqueous buffer solutions and/or protease inhibitors, employing any of a variety of buffers, such as phosphate, Tris, or the like, at physiological pH, can be used.

C. Assaying Periostin Protein

Periostin protein can be detected and quantified by any of a number of methods well known to those of skill in the art for polypeptide detection. These may include analytic biochemical methods such as electrophoresis, capillary electrophoresis, electrochemiluminescence, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In one embodiment, periostin protein is detected/quantified in an electrophoretic polypeptide separation (e.g. a 1- or 2-dimensional electrophoresis). Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.).

A variation of this embodiment utilizes a Western blot (immunoblot) analysis to detect and quantify the presence of periostin protein in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with antibodies that specifically bind the analyte. Antibodies that specifically bind to the analyte may be directly labeled or alternatively may be detected subsequently using labeled antibodies (e.g., labeled sheep anti-mouse antibodies) that specifically bind to a domain of the primary antibody.

In certain of the above-described embodiments, the sample and/or periostin protein is transformed in some manner in the course of the assay. For example, the sample may be fractionated such that periostin protein is separated from at least one other sample component. The periostin protein can be recovered in a liquid fraction or can be detected while embedded in a separation medium, such as a gel. For mass spectroscopy, periostin protein is volatilized for detection.

In a preferred embodiment, periostin protein is detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. In preferred embodiments, the capture agent is an antibody.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542).

Preferred immunoassays for detecting the target polypeptide(s) are either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled periostin protein is added to the sample, and the sample is then contacted with a capture agent. The amount of labeled periostin protein bound to the antibody is inversely proportional to the concentration of periostin protein present in the sample.

In illustrative embodiments, periostin protein is measured in urine using a "dipstick" assay.

The assays of this invention are scored (as positive or negative or quantity of analyte) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration.

a. Antibodies

Antibodies useful in the immunoassay methods of the invention include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley antibody laboratories, Bethyl Laboratories, Anawa, Eurogenetec, etc.).

b. Solid Phase

For embodiments of the invention that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto, bonded, or laminated to appropriate inert carriers, such as paper, glass, plastic films, fabrics, or the like.

The porous structure of nitrocellulose has excellent absorption and adsorption qualities for a wide variety of reagents including monoclonal antibodies. Nylon also possesses similar characteristics and also is suitable.

Porous solid phases useful in the invention can be in the form of sheets of thickness from about 0.01 to 0.5 mm, e.g., about 0.1 mm. The pore size may vary within wide limits, and is preferably from about 0.025 to about 15 microns, especially from about 0.15 to about 15 microns.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods of the present invention can be adapted for use in systems that utilize microparticle technology including automated and semi-automated systems wherein the solid phase comprises a microparticle. Such systems include those described in pending U.S. App. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption on the porous material, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase material or onto microparticles which then are retained by a solid phase material. Ion capture procedures for immobilizing an immobilizable reaction complex with a negatively charged polymer, described in U.S. App. No. 150,278, corresponding to EP Publication No. 0326100, and U.S. App. No. 375,029 (EP Publication No. 0406473), can be employed according to the present invention to affect a fast solution-phase immunochemical reaction. In these procedures, an immobilizable immune complex is separated from the rest of the reaction mixture by ionic interactions between the negatively charged polyanion/immune complex and the previously treated, positively charged porous matrix and detected by using any of a number of signal-generating systems, including, e.g., chemiluminescent systems, as described in U.S. App. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis(succinimidyl)suberate, SPPD 9 succinimidyl 3-[2-pyridyldithio]propionate), SMCC (succinimidyl-4-[Nmaleimidomethyl]cyclohexane-1-carboxylate), SIAB (succinimidyl[4iodoacetyl]aminobenzoate), and SMPB (succinimidyl 4-[1maleimidophenyl]butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. App. No. 150,278, filed Jan. 29, 1988, and U.S. App. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

c. Labeling Systems

As discussed above, many immunoassays according to the invention employ a labeled detection agent.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, texas red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^{3}H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

D. Assaying Periostin mRNA

Changes in periostin expression level can be detected by measuring changes in levels of mRNA and/or a polynucleotide derived from the mRNA (e.g., reverse-transcribed cDNA, etc.).

Polynucleotides can be prepared from a sample according to any of a number of methods well known to those of skill in the art. General methods for isolation and purification of polynucleotides are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

a. Amplification-Based Assays

In one embodiment, amplification-based assays can be used to detect, and optionally quantify, a polynucleotide encoding periostin. In exemplary amplification-based assays, periostin mRNA in the sample acts as a template in an amplification reaction carried out with a nucleic acid primer that contains a detectable label or component of a labeling system. Suitable amplification methods include, but are not limited to, polymerase chain reaction (PCR); reverse-transcription PCR (RT-PCR); ligase chain reaction (LCR) (see Wu and Wallace (1989) *Genomics* 4: 560, Landegren et al. (1988) *Science* 241: 1077, and Barringer et al. (1990) *Gene* 89: 117; transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874); dot PCR, and linker adapter PCR, etc.

To determine the level of periostin mRNA, any of a number of well known "quantitative" amplification methods can be employed. Quantitative PCR generally involves simultaneously co-amplifying a known quantity of a control sequence using the same primers. This provides an internal standard that may be used to calibrate the PCR reaction. Detailed protocols for quantitative PCR are provided in PCR Protocols, A Guide to Methods and Applications, Innis et al., Academic Press, Inc. N.Y., (1990).

b. Hybridization-Based Assays

Nucleic acid hybridization simply involves contacting a nucleic acid probe with sample polynucleotides under conditions where the probe and its complementary target nucleotide sequence can form stable hybrid duplexes through complementary base pairing. The nucleic acids that do not form hybrid duplexes are then washed away leaving the hybridized nucleic acids to be detected, typically through detection of an attached detectable label or component of a labeling system. Methods of detecting and/or quantifying polynucleotides using nucleic acid hybridization techniques are known to those of skill in the art. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587. Methods of optimizing hybridization conditions are described, e.g., in Tijssen (1993) *Laboratory Techniques in Biochemistry and Molecular Biology*, Vol. 24: *Hybridization With Nucleic Acid Probes*, Elsevier, N.Y.).

The nucleic acid probes used herein for detection of periostin mRNA can be full-length or less than the full-length of these polynucleotides. Shorter probes are generally empirically tested for specificity. Preferably, nucleic acid probes are at least about 15, and more preferably about 20 bases or longer, in length. Visualization of the hybridized probes allows the qualitative determination of the presence or absence of periostin mRNA, and standard methods (such as, e.g., densitometry where the nucleic acid probe is radioactively labeled) can be used to quantify the level of periostin mRNA).

A variety of additional nucleic acid hybridization formats are known to those skilled in the art. Standard formats include sandwich assays and competition or displacement assays. Sandwich assays are commercially useful hybridization assays for detecting or isolating polynucleotides. Such assays utilize a "capture" nucleic acid covalently immobilized to a solid support and a labeled "signal" nucleic acid in solution. The sample provides the target polynucleotide. The capture nucleic acid and signal nucleic acid each hybridize with the target polynucleotide to form a "sandwich" hybridization complex.

In one embodiment, the methods of the invention can be utilized in array-based hybridization formats. In an array format, a large number of different hybridization reactions can be run essentially "in parallel." This provides rapid, essentially simultaneous, evaluation of a number of hybridizations in a single experiment. Methods of performing hybridization reactions in array-based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays, can be produced according to a wide variety of methods well known to those of skill in the art. For example, in a simple embodiment, "low-density" arrays can simply be produced by spotting (e.g., by hand using a pipette) different nucleic acids at different locations on a solid support (e.g., a glass surface, a membrane, etc.). This simple spotting approach has been automated to produce high-density spotted microarrays. For example, U.S. Pat. No. 5,807,522 describes the use of an automated system that taps a microcapillary against a surface to deposit a small volume of a biological sample. The process is repeated to generate high-density arrays. Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high-density oligonucleotide microarrays. Synthesis of high-density arrays is also described in U.S. Pat. Nos. 5,744,305; 5,800,992; and 5,445,934.

In a particular embodiment, the arrays used in this invention contain "probe" nucleic acids. These probes are then hybridized respectively with their "target" nucleotide sequence(s) present in polynucleotides derived from a biological sample. Alternatively, the format can be reversed, such that polynucleotides from different samples are arrayed and this array is then probed with one or more probes, which can be differentially labeled.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials that can be employed include paper, ceramics, metals, metalloids, semiconductive materials, and the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, and/or enhance signal detection. If covalent bonding between a compound and the surface is desired, the surface will usually be polyfunctional or be capable of being polyfunctionalized. Functional groups that may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Arrays can be made up of target elements of various sizes, ranging from about 1 mm diameter down to about 1 µm. Relatively simple approaches capable of quantitative fluorescent imaging of 1 $cm^2$ areas have been described that permit acquisition of data from a large number of target elements in a single image (see, e.g., Wittrup (1994) *Cytometry* 16:206-213, Pinkel et al. (1998) *Nature Genetics* 20: 207-211).

Hybridization assays according to the invention can also be carried out using a MicroElectroMechanical System (MEMS), such as the Protiveris' multicantilever array.

c. Polynucleotide Detection

Periostin polynucleotides can be detected in the above-described polynucleotide-based assays by means of a detectable label. Any of the labels discussed above can be used in the polynucleotide-based assays of the invention. The label may be added to a probe or primer or sample polynucleotides prior to, or after, the hybridization or amplification. So called "direct labels" are detectable labels that are directly attached to or incorporated into the labeled polynucleotide prior to conducting the assay. In contrast, so called "indirect labels" are joined to the hybrid duplex after hybridization. In indirect labeling, one of the polynucleotides in the hybrid duplex carries a component to which the detectable label binds. Thus, for example, a probe or primer can be biotinylated before hybridization. After hybridization, an avidin-conjugated fluorophore can bind the biotin-bearing hybrid duplexes, providing a label that is easily detected. For a detailed review of methods of the labeling and detection of polynucleotides, see *Laboratory Techniques in Biochemistry and Molecular Biology*, Vol. 24: *Hybridization With Nucleic Acid Probes*, P. Tijssen, ed. Elsevier, N.Y., (1993)).

The sensitivity of the hybridization assays can be enhanced through use of a polynucleotide amplification system that multiplies the target polynucleotide being detected. Examples of such systems include the polymerase chain reaction (PCR) system and the ligase chain reaction (LCR) system. Other methods described in the art are the nucleic acid sequence based amplification (NASBAO, Cangene, Mississauga, Ontario) and Q Beta Replicase systems.

In an illustrative embodiment, suitable for use in amplification-based assays of the invention, a primer contains two fluorescent dyes, a "reporter dye" and a "quencher dye." When intact, the primer produces very low levels of fluorescence because of the quencher dye effect. When the primer is cleaved or degraded (e.g., by exonuclease activity of a polymerase, see below), the reporter dye fluoresces and is detected by a suitable fluorescent detection system. Amplification by a number of techniques (PCR, RT-PCR, RCA, or other amplification method) is performed using a suitable DNA polymerase with both polymerase and exonuclease activity (e.g., Taq DNA polymerase). This polymerase synthesizes new DNA strands and, in the process, degrades the labeled primer, resulting in an increase in fluorescence. Commercially available fluorescent detection systems of this type include the ABI Prism® Systems 7000, 7700, or 7900 (TaqMan®) from Applied Biosystems or the LightCycler® System from Roche.

E. Periostin Levels

Once determined, a periostin protein and/or mRNA level can be recorded in a patient medical record. In certain embodiments, the methods of the invention include making a diagnosis, often a differential diagnosis, based at least in part on the periostin level. This diagnosis can also be recorded in a patient medical record. For example, in various embodiments, the diagnosis of peritoneal injury is recorded in a medical record. The medical record can be in paper form and/or can be maintained in a computer-readable medium. The medical record can be maintained by a laboratory, physician's office, a hospital, a health maintenance organization, an insurance company, and/or a personal medical record website. In certain embodiments, a diagnosis, based at least in part on the periostin level, is recorded on or in a medic alert article such as a card, a worn article, and/or a radiofrequency identification (RFID) tag.

In particular embodiments, the methods of the invention include informing the subject of a result of the periostin assay and/or of a diagnosis based at least in part on the periostin level. The patient can be informed verbally, in writing, and/or electronically.

The methods of the invention can include prescribing, initiating, and/or altering prophylaxis and/or therapy for peritoneal injury. In certain embodiments, the methods can entail ordering and/or performing one or more additional assays. For example, if the periostin level is determined to be within a normal range (i.e., not elevated), the periostin assay may be repeated to rule out a false negative result, and/or one or more additional periostin assays may be performed to monitor the subject's status. If the periostin level is determined to be elevated, it may be desirable repeat the periostin assay to rule out a false positive result. In certain embodiments, it will be desirable to assay another indicator of, e.g., peritoneal injury, to confirm a diagnosis. Exemplary indicators of peritoneal injury include PDGF, collagen IV, the peritoneal equilibration test (PET), and encapsulating peritoneal sclerosis (EPS). Periostin may be sequentially measured in patients in whom the assay shows peritoneal injury in order to demonstrate remission, and in those with remission, in order to demonstrate relapse of peritoneal injury.

IV. Test Kits

The invention also provides a test kit for assaying for periostin. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s) that may be desirable from a user standpoint, such as a buffer(s), a diluent(s), a standard(s), and/or any other material useful in sample processing, washing, or conducting any other step of the assay.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are offered to illustrate, but not to limit, the claimed invention.

Example 1

Pan-JAK Inhibitor (JAKi) P6 and a Narrow Spectrum JAK Inhibitor (JAK1/2i) LSN3103801 Affect Peritoneal Small Solute Clearance and UF Capacity Background This example shows that in rats undergoing PD with bioincompatible peritoneal dialysis fluid (biPDF), Pan-JAK inhibitor (JAKi) P6 and a narrow spectrum JAK inhibitor (JAK1/2i) LSN3103801 (properties similar to INCB02805027) preserved the structural integrity of the peritoneal membrane compared to placebo.

High technical failure rates diminish PD utilization globally, but especially in the US, where bicarbonate-based PD solution is unavailable. There are many causes[17, 18, 25, 26, 28, 29], including peritoneal barrier (Pbarrier) exposure to lactate[30-32], low dialysate pH[31-34], high glucose content[32, 35, 36], advanced glycation endproducts (AGE), glucose-degradation products (GDP) generated from peritoneal dialysis fluid (PDF) heat sterilization[35, 37-39], inflammatory foreign-body response to the catheter[14, 15], uremia[7, 40], and peritonitis[4, 28, 41, 42]. Uremia induces considerable structural Pbarrier pathology.

Prior to initiating PD, impaired peritoneal structural integrity from uremia is associated with Pbarrier pathology[5, 7, 43]. However, during PD, further compromise is driven by continued oxidant injury, inflammation, and a crescendo of chemokine, cytokine, and growth factor elaboration by resident Pbarrier cells and infiltrating mononuclear cells[5-7, 11, 25, 29, 36, 44].

During PD, the mesothelium undergoes recurrent denudation and regeneration[45]. In some reported studies, mesothelium might have been artifactually lost during tissue harvesting. In one study, mesothelium was absent in 49% of PD patients vs. only 17% in individuals not on PD[6], suggesting denudation in ~30% of PD patients. Some mesothelial cells dedifferentiated, adopting mesenchymal characteristics[46-50]. Injured mesothelial cells secreted chemokines, cytokines, and growth factors[18, 44, 51-53]. Mononuclear leukocytes invaded the Pbarrier[18, 19] in "milky spots"[18, 54] and in the parietal peritoneum, and they entered PDF, contributing soluble and cellular inflammatory factors[29, 55, 56]. The Pbarrier glycocalyx was reduced; some posited that this impaired UF and solute transport[12, 13, 57]. Fibroblasts proliferated, inducing submesothelial expansion, the pathologic expression of fibrosis. Lymphangiogenesis and neovascularization occurred[21]. Vessels hyalinized and narrowed[5, 6].

These structural changes accompanied functional Pbarrier failure[6, 41]. Several treatment strategies were tested. In most countries, bicarbonate-based "biocompatible" PDF has replaced biPDF, but this is unavailable in the US. In secondary analyses of recently published RCTs, the use of biocompatible PDF preserved small solute clearance and UF for at least 1-2 years[56, 58], while the performance of biPDF varied. However, even the exclusive use of so-called biocompatible solutions would not eliminate Pbarrier failure[14, 15, 17, 26].

Other strategies were tested. Endothelial nitric oxide synthase (eNOS) knockout mice had less Pbarrier failure than wildtype (WT) in peritonitis[59]. Fibroblast depletion attenuated fibrosis and angiogenesis[60]. Mesothelial dedifferentiation implicated in Pbarrier fibrosis and neovascularization was attenuated in vitro by mammalian target of rapamycin (mTOR) antagonists and by the agonist actions of bone morphogenetic protein 7 (BMP7)[61, 62]. Injections of neutralizing antibodies of receptor for advanced glycosylation end products (anti-RAGE antibodies) in diabetic rats and non-diabetic subtotally nephrectomized rats attenuated increments in Pbarrier transforming growth factor beta (TGF-β) and submesothelial fibrosis[35, 63], but did not improve UF or small solute transport[35].

The roles of cytokines, chemokines, and growth factors in mediating oxidant and inflammatory injury to the Pbarrier have been the subject of intense study to identify potential therapeutic targets[17, 18, 28, 29, 64]. Glycosaminoglycan supplementation had varying outcomes[13, 57, 65-69]. Due to the complexity of the interactions of the many pro-oxidant pro-inflammatory signals, coupled to contributions from both leukocytic invasion and Pbarrier native cells, the likelihood of significantly attenuating injury in humans by targeting individual oxidant or inflammatory molecules or individual cell types is low.

By contrast, this example tested the relative value of broad vs. narrow JAK inhibition (JAKi) compared to controls in the preservation of Pbarrier structure and function.

The most innovative solutions would address the totality of the injuries in PD, both dialysate-dependent and dialysate-independent. Testing the effect of JAK/STAT signaling inhibition meets this standard for innovation. Its strength is in targeting an integrated pathway of oxidant and inflammatory injury to simultaneously address injury in constituent Pbarrier cells and influxed mononuclear cells. While the contribution of biPDF to Pbarrier failure is a uniquely American problem, the totality of Pbarrier membrane failure remains one whose solution has global consequences[26].

The mechanisms causing Pbarrier structural and functional decline during PD are partially understood. Oxidant injury and inflammation play key roles; AGEs and GDPs are implicated. JAK/STAT signaling mediates the cellular response of dozens of cytokines, chemokines and growth factors. The four JAKs and six STATs combine in several combinations to induce varied responses[22, 23]. JAK/STAT signaling is implicated in mediating peritoneal injury in PD[17, 18], but direct evidence is scant[24, 25]. Leptin activated JAK 2 and STAT 3 in cultured human peritoneal mesothelial cells, and the JAK2 inhibitor AG-490 abolished leptin-induced TGFβ synthesis by these cells[24]. Additional evidence can be inferred from other conditions and tissues[22, 71, 72].

Results

The following findings support a key role for JAK/STAT signaling in peritoneal inflammation and fibrosis from biPDF.

Figure 1B:
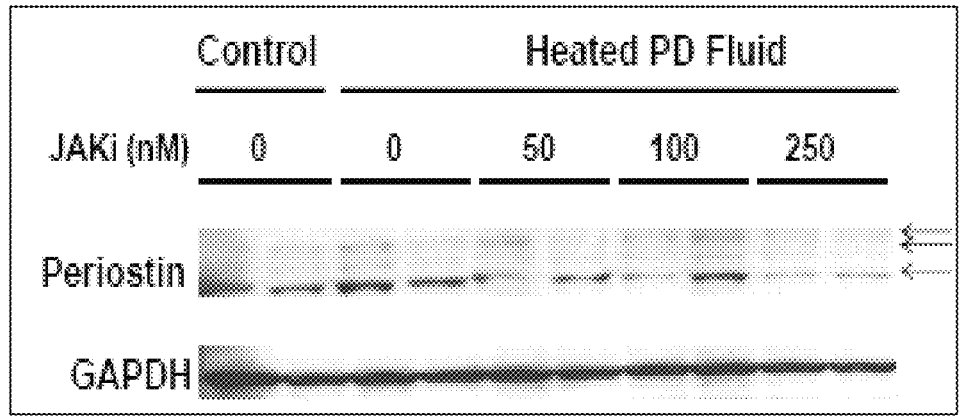

Mesothelial cell exposure to heated PDF in vitro activated JAK/STAT signaling and induced the STAT-associated protein periostin. Heat-sterilization of PDF generates GDPs. A commercially available immortalized human mesothelial cell line was cultured in standard medium, then switched to control medium or heat-sterilized PDF (30:70, medium:PDF)×4 hrs. Heated PDF induced STAT1 phosphorylation, and the pan-JAKi P6 attenuated this (immunoblot doublet, FIG. 1A). After 24 hrs, P6 also attenuated the secretion of the injurious STAT-associated protein periostin into the medium (immunoblot triplet, FIG. 1B). Five characteristics of periostin make it an attractive marker of Pbarrier injury. 1) Periostin is a marker and mediator for the adoption of a mesenchymal phenotype by injured or transformed epithelial cells[73-75]. 2) It participates in fibrous healing[76]. Others show periostin in the Pbarrier of patients with fibrosis and encapsulating peritoneal sclerosis (Braun et al, ASN poster, 2011). 3) Periostin supports neovascularization[77]. 4) It has a bidirectional regulatory relationship with TGF-β[78]. 5) It's promoter region has STAT1 and 5 binding sites (www1.lsabiosciencesl.lcom/chipqpersearch.php?species_id=0&nfactor=n&ninfo=n&ngene=n&B2=Search&src=genecard&factor=Over+200+TF&gene=POSTN). Thus, we can use periostin to affirm JAK/STAT signaling and mesothelial dedifferentiation. These data showed that in cultured mesothelial cells exposed to heat-sterilized PDF, JAK/STAT activation was associated with the secretion of an injurious STAT-associated protein, periostin, and the pan-JAKi P6 attenuated activation and the injury signal.

Figure 2A:
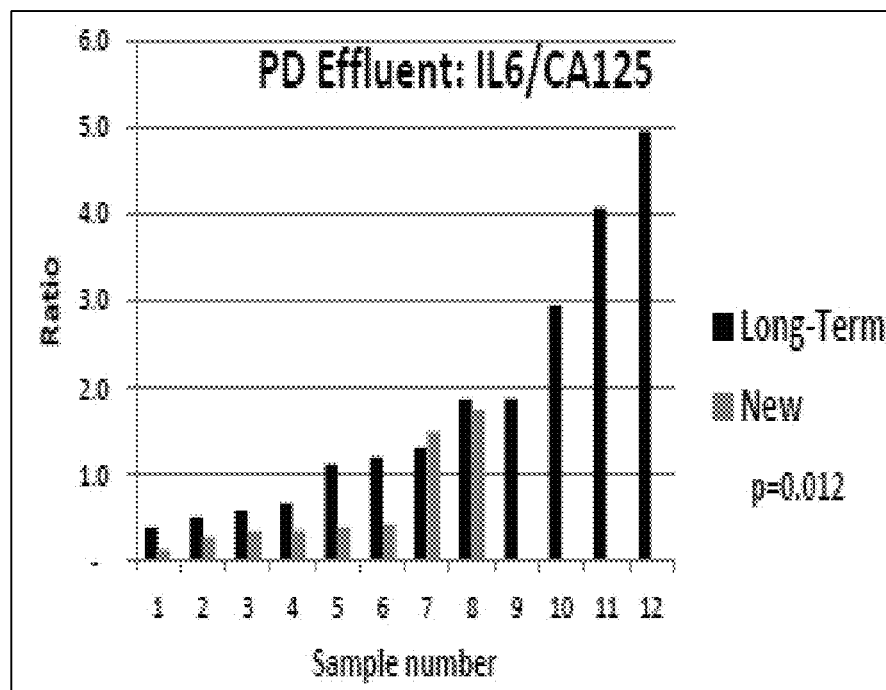
FIG. 2A-B. The JAK/STAT activators IL6 (A) and IL15 (B) are increased in PDeff samples (n=20) from Long-Term (LT, >6 mos) vs. New (N, ≤2 weeks) patients on PD.
Figure 2B:
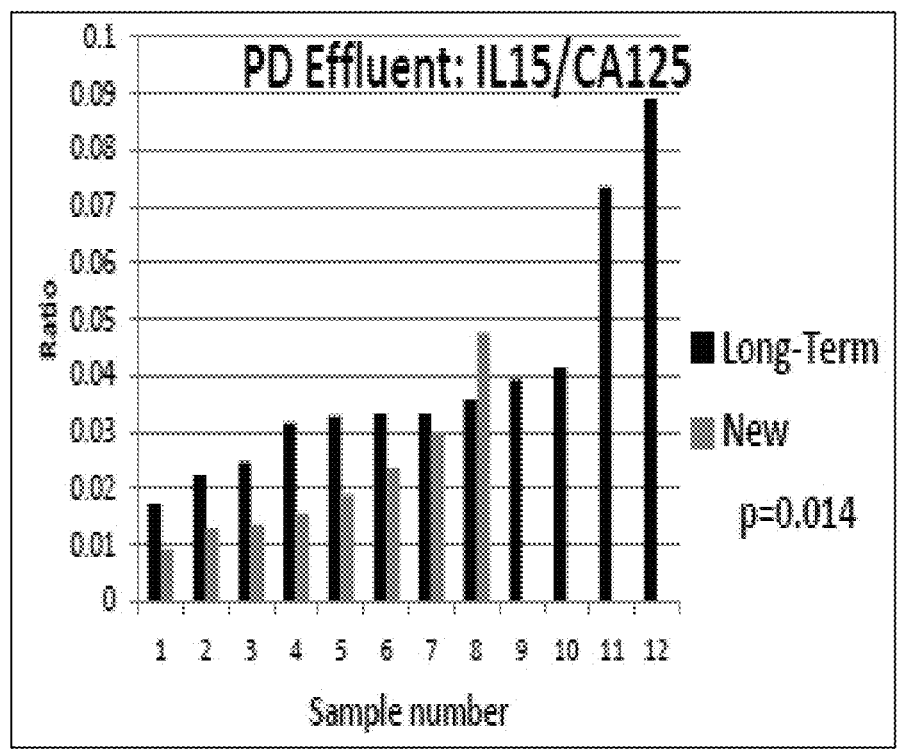

The JAK/STAT activators IL6 and IL15 were increased in PDeff samples (n=20) from Long-Term (LT, >6 mos) vs. New (N, ≤2 weeks) patients on PD (electrochemiluminescence, Meso Scale Discovery, San Diego, Calif.). Factored for CA125, a measure of mesothelial cell mass[79], values for the JAK-activators IL6 (FIG. 2A) and IL15 (FIG. 2B) were higher in LT than N samples (Mann-Whitney U test). IL6 has been implicated in Pbarrier failure[56, 64, 80, 81]. IL6 receptor-binding signals via JAK 1/2 activation of STATs 1 and 3. IL15 is expressed ubiquitously, but largely in monocytes, and supports proliferation of B and T lymphocytes and natural killer cells[82]. IL-15 was also increased in PD effluent (PDeff), with values that inversely correlated with UF capacity[83]. IL15 receptor binding activated JAKs 1 and 3, and STATs 3, 5, and 6. Thus, higher levels of JAK/STAT-activating cytokines are present in Long-Term vs. New PD patients, supporting the premise that JAK inhibitors can attenuate inflammation in PD.

Figure 3:
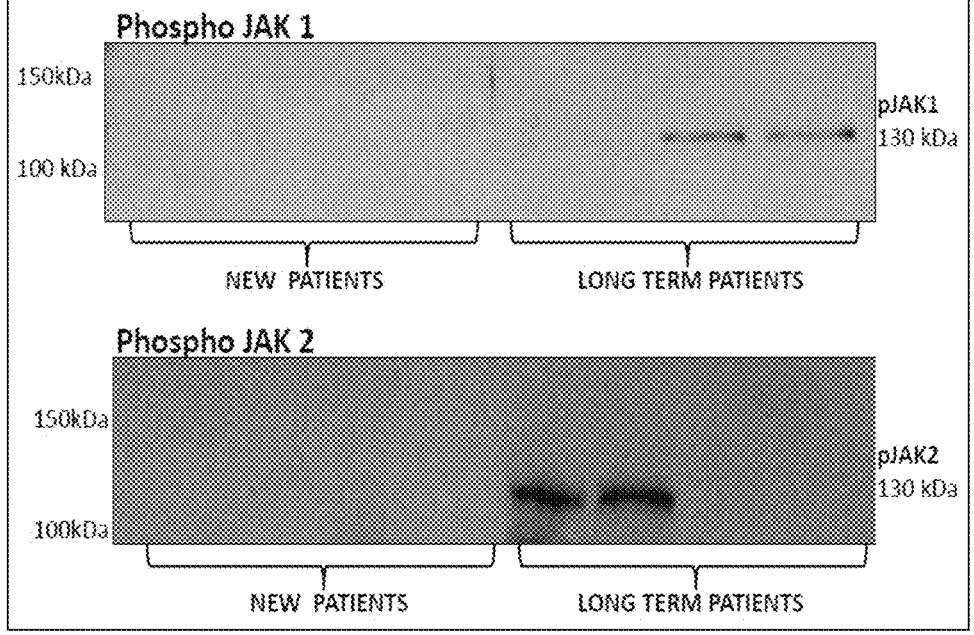
FIG. 3. JAK1 and JAK2 phosphorylation is found in PDeff cell lysate from Long-Term (n=4) but not in New (n=4) patients.

JAK1 and JAK2 phosphorylation was found in PDeff cell lysate from Long-Term (n=4) but not New (n=4) patients. PDeff cells were collected from overnight automated PDeff, centrifuged, and lysates immunoblotted with anti-human pJAK1 and pJAK2. All of the Long-Term PD patients, but none of four New PD patients expressed either pJAK1 or pJAK2 (immunoblot, FIG. 3). These data demonstrate the activation of inflammatory JAK/STAT signaling in PDeff cells with time on PD.

Figure 4A:
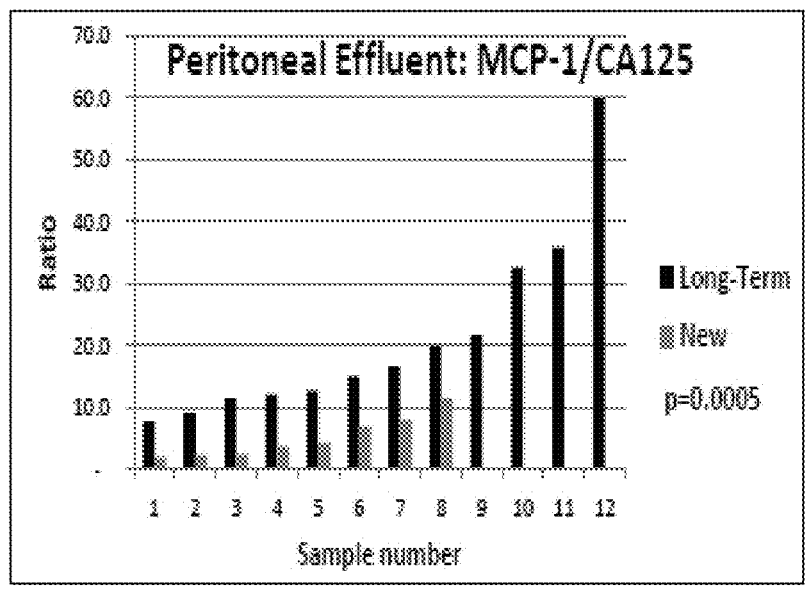
FIG. 4A-D. PD effluent shows more of the STAT-associated proteins MCP-1 (A) and periostin in Long-Term vs. New patients. (B) Periostin detected (by immunoblotting; triplet at 97, 90, and 75 kD) in the PDeff of Long-Term (n=4) vs. New patients (n=4). (C) The identification of the 3 bands was confirmed by immunoprecipitation with anti-gamma-carboxyglutamic acid (Gla) antibody followed by immunoblotting with anti-periostin antibody. 90 kD recombinant protein is also shown as control. (D) Periostin was also detected by ELISA.
Figure 4B:
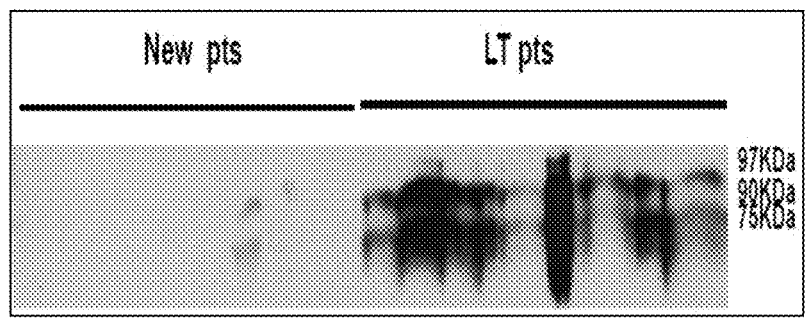
Figure 4C:
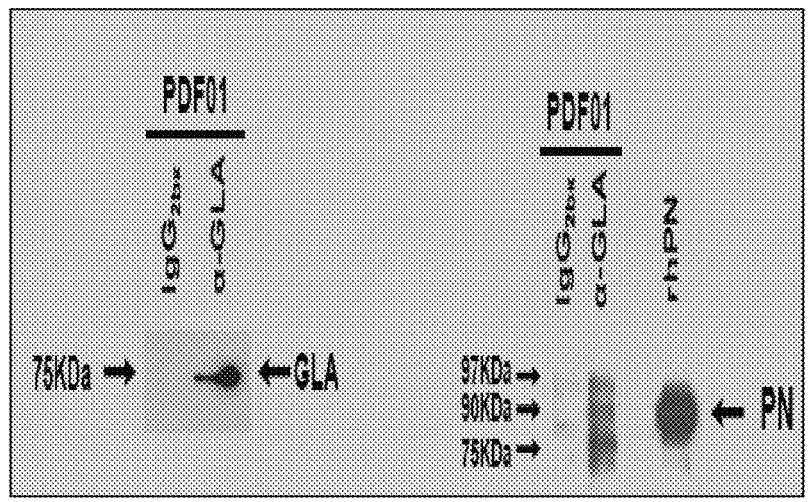
Figure 4D:
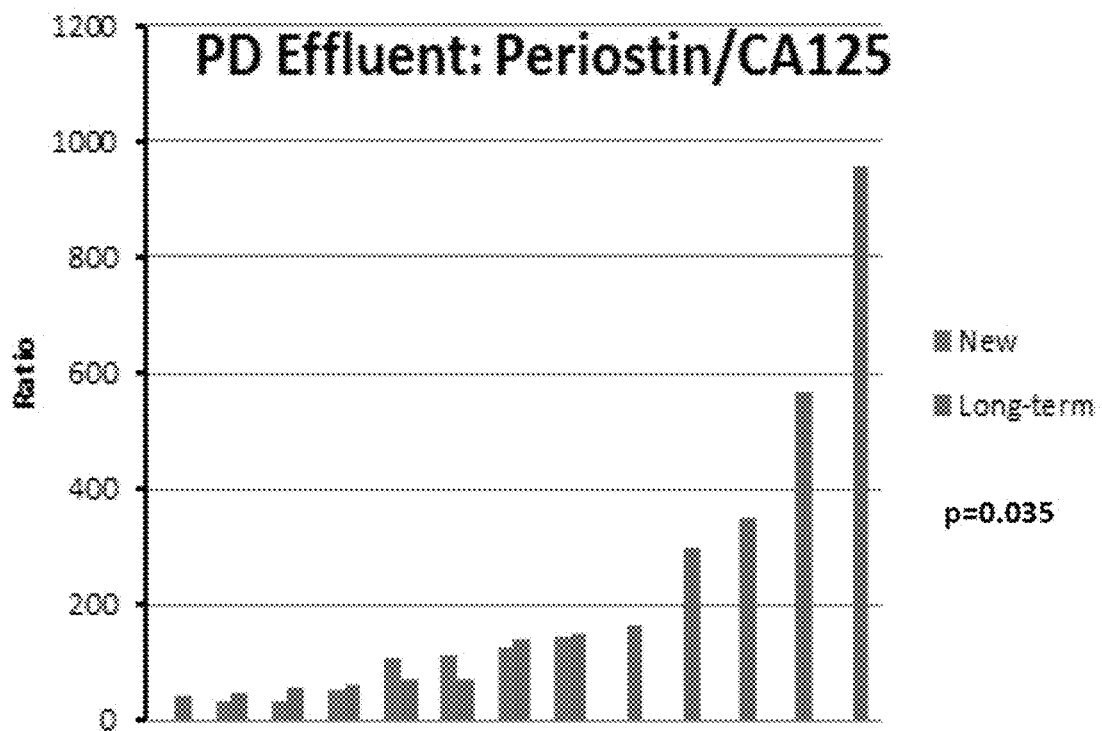

PDeff showed more of the STAT-associated proteins MCP-1 and periostin in Long-Term vs. New patients. Data showed significantly more MCP-1 in samples from PDeff from Long-Term vs. New patients (electrochemiluminescence, Meso Scale Discovery FIG. 4A). MCP-1 has long been implicated in the inflammatory injury of the Pbarrier in PD patients [52, 64, 69], signals via JAK2, and has STAT1, 1A, and 1B binding sites in its promoter region. Periostin was also higher (by immunoblotting; triplet at 97, 90, and 75 kD) in the PDeff of Long-Term (n=4) vs. New patients (n=4) (FIG. 4B); see also ELISA results (FIG. 4D). The identification of the 3 bands was confirmed by immunoprecipitation with anti-gamma-carboxyglutamic acid (Gla) antibody followed by immunoblotting with anti-periostin antibody[74] (FIG. 4C). 90 kD recombinant protein is also shown as control.

Four periostin isoforms exist (GeneCards). The 75 kD isoform is the most stable with the longest half-life[84]. Three bands like the ones we observed were also seen in developing teeth and heart[85], with interesting implications for pathogenesis. Periostin has STAT 1A and 5 binding sites in its promoter region. It is increased in patients with Pbarrier fibrosis and in encapsulating peritoneal sclerosis (Braun et al, ASN poster session, 2011). We reported periostin as a mediator of epithelial dedifferentiation[73], as have others[75, 77]. We also identified other STAT-associated proteins present in higher amounts in Long-term vs. New PDeff samples, including trefoil factor-3, NGAL, β2-microglobulin, aldose reductase, and the phosphate exchanger nucleotide diphosphate kinase B. Many chemokines, cytokines, and growth factors that activate JAK/STAT signaling are increased in the PDeff of patients, including but not limited to members of the interleukin family, TGF-β, PDGF, and leptin[24, 28, 44, 52, 86, 87].

The above data showed the presence of STAT-associated injury proteins in the PDeff of patients on long-term PD, indicating that injury from PD exposure can be attenuated by JAKi.

In rats, 10 days of PD with 4.25% Dianeal induced mesothelial cell reactive hyperplasia, fibrosis, inflammation, and JAK1 phosphorylation, all of which are attenuated by a JAK1/2 inhibitor. Visceral and parietal peritoneum respond to biPDF differently[33, 88], so only like tissues were compared across treatments. The parietal peritoneum exposed to normal saline showed normal mesothelium and submesothelial compact zone (n=3, FIG. 5A), but there was inflammation and early fibrosis after exposure to 4.25% Dianeal (n=4, FIG. 5B). This was attenuated by i.p. treatment with a JAK1/2 inhibitor, which displayed a thin mesothelial cell layer and minimally expanded submesothelial compact zone (n=2, FIG. 5C). Representative visceral peritoneum shows that the mesothelial cell layer was delicate and normal with saline dialysate exposure (FIG. 5D), but showed reactive hyperplasia after exposure to 4.25% Dianeal (FIG. 5E). This was markedly attenuated by i.p. treatment with the JAK1/2 inhibitor (FIG. 5F).

Figure 5M:
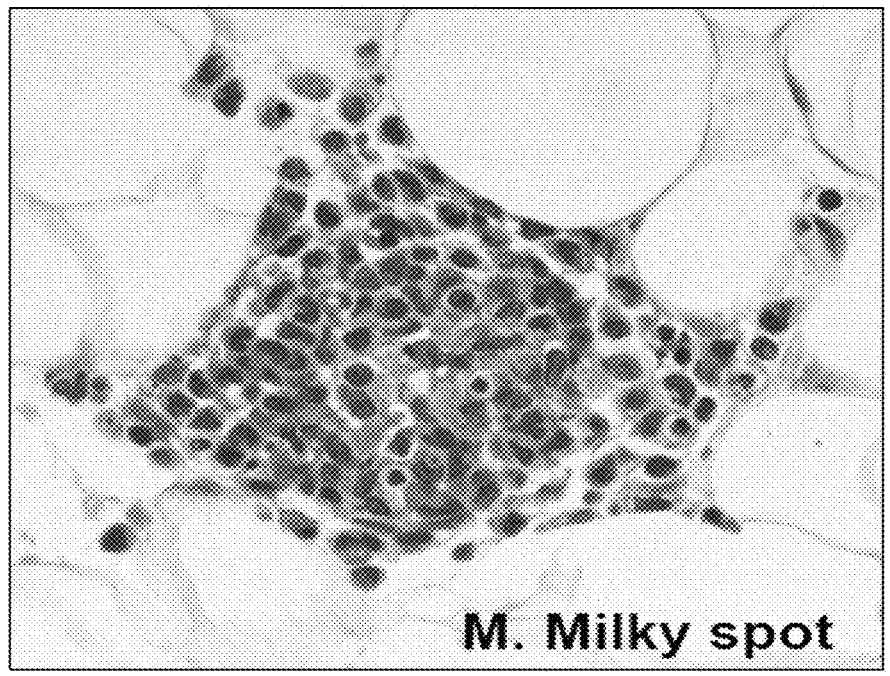
FIG. 5A-N. (A-M) In rats, 10 days of PD with 4.25% Dianeal induces mesothelial cell reactive hyperplasia, fibrosis, inflammation, and JAK1 phosphorylation, all of which are attenuated by a JAK1/2 inhibitor. Parietal peritoneum exposed to: (A) Saline dialysate; (B) 4.25% Dianeal; (C) 4.25% Dianeal with JAK1/2 inhibitor. Visceral peritoneum exposed to: (D) Saline dialysate; (E) 4.25% Dianeal; (F) 4.25% Dianeal with JAK1/2 inhibitor. Phosphorylated JAK1 in parietal peritoneum exposed to: (G) Saline dialysate; (H) 4.25% Dianeal; (I) 4.25% Dianeal with JAK1/2 inhibitor. Phosphorylated JAK1 in visceral peritoneum exposed to: (J) Saline dialysate; (K) 4.25% Dianeal; (L) 4.25% Dianeal with JAK1/2 inhibitor. (M) Omental macrophage accumulation in so-called "milky spots." (All original magnification×160). (N) Exposure to peritoneal dialysis fluid induces caspase-3 cleavage, indicating cell death, which is reduced in the presence of JAKi P6. See Example 2.

In parietal peritoneum, no or minimal phospho-JAK1 staining was observed in rats dialyzed against saline (FIG. 5G), or in rats dialyzed with 4.25% Dianeal+JAK1/2 inhibitor (FIG. 5I). There was abundant phospho-JAK1 staining (brown) in the mesothelium and cells in the submesothelial compact zone that were exposed to 4.25% Dianeal (FIG. 5H). Visceral peritoneum from saline-dialyzed rats also stained minimally or not at all for phospho-JAK1 (FIG. 5J). In contrast, substantial staining for phospho-JAK1 was present in the hyperplastic mesothelial cells induced by exposure to 4.25% Dianeal (FIG. 5K). As anticipated, minimal or no phospho-JAK1 staining was observed in the tissue from rats receiving 4.5% Dianeal+JAK1/2 inhibitor, and the mesothelial cell reactive hyperplasia was markedly attenuated (FIG. 5L). Finally, we were able to identify omental macrophage accumulation in so-called "milky spots" (FIG. 5M). (All original magnification×160). Prophylactic ceftazidime (500 mg/L) was given i.p. with PDF; no infections occurred. All PDF WBCs counts were <637 cells/μl (normal is up to 1,700 cells/μl[89]). These data clearly show that the JAK1/2 inhibitor prevented the JAK1 phosphorylation induced by exposure to 4.25% Dianeal and prevented mesothelial cell reactive hyperplasia, fibrosis, and inflammation. The data strongly support the rationale that JAK/STAT inhibitors preserve the Pbarrier.

REFERENCES

1. Jiwakanon S, Chiu Y W, Kalantar-Zadeh K, Mehrotra R. Peritoneal dialysis: an underutilized modality. Current opinion in nephrology and hypertension 2010; 19:573-7.
2. Churchill D N, Thorpe K E, Nolph K D, Keshaviah P R, Oreopoulos D G, Pagé D. Increased peritoneal membrane transport is associated with decreased patient and technique survival for continuous peritoneal dialysis patients. The Canada-USA (CANUSA) Peritoneal Dialysis Study Group. Journal of the American Society of Nephrology 1998; 9:1285-92.
3. Davies S J. Longitudinal relationship between solute transport and ultrafiltration capacity in peritoneal dialysis patients. Kidney international 2004; 66:2437-45.
4. Davies S J, Bryan J, Phillips L, Russell G I. Longitudinal changes in peritoneal kinetics: the effects of peritoneal dialysis and peritonitis. Nephrology, dialysis, transplantation: official publication of the European Dialysis and Transplant Association—European Renal Association 1996; 11:498-506.
5. Williams J D, Craig K J, Ruhland Cv, Topley N, Williams G T. The natural course of peritoneal membrane biology during peritoneal dialysis. Kidney international 2003; 64:S43-S49.
6. Williams J D, Craig K J, Topley N, et al. Morphologic Changes in the Peritoneal Membrane of Patients with Renal Disease. Journal of the American Society of Nephrology 2002; 13:470-479.
7. Honda K, Hamada C, Nakayama M, et al. Impact of uremia, diabetes, and peritoneal dialysis itself on the pathogenesis of peritoneal sclerosis: a quantitative study of peritoneal membrane morphology. Clin J Am Soc Nephrol 2008; 3:720-8.
8. Honda K, Nitta K, Horita S, Yumura W, Nihei H. Morphological changes in the peritoneal vasculature of patients on CAPD with ultrafiltration failure. Nephron 1996; 72:171-6.
9. Honda K, Nitta K, Horita S, et al. Accumulation of advanced glycation end products in the peritoneal vasculature of continuous ambulatory peritoneal dialysis patients with low ultra-filtration. Nephrology, dialysis, transplantation: official publication of the European Dialysis and Transplant Association—European Renal Association 1999; 14:1541-9.
10. Wang T, Lindholm B. Peritoneal dialysis solutions. Peritoneal Dialysis International 2001; 21:S89-S95.
11. Krediet R T. The peritoneal membrane in chronic peritoneal dialysis. Kidney international 1999; 55:341-56.
12. Yung S, Chan T M. Glycosaminoglycans and proteoglycans: overlooked entities? Peritoneal dialysis international: journal of the International Society for Peritoneal Dialysis 2007; 27 Suppl 2:S104-9.
13. Flessner M F. Endothelial glycocalyx and the peritoneal barrier. Peritoneal dialysis international: journal of the International Society for Peritoneal Dialysis 2008; 28:6-12.
14. Flessner M F, Credit K, Henderson K, et al. Peritoneal changes after exposure to sterile solutions by catheter. Journal of the American Society of Nephrology: JASN 2007; 18:2294-302.
15. Flessner M F, Credit K, Richardson K, et al. Peritoneal inflammation after twenty-week exposure to dialysis solution: effect of solution versus catheter-foreign body reaction. Peritoneal dialysis international: journal of the International Society for Peritoneal Dialysis 2010; 30:284-93.
16. Lai K N, Leung J C. Inflammation in peritoneal dialysis. Nephron Clin Pract 2010; 116:c1'-8.
17. Lai K N, Tang S C, Leung J C. Mediators of inflammation and fibrosis. Peritoneal dialysis international: journal of the International Society for Peritoneal Dialysis 2007; 27 Suppl 2:S65-71.
18. Schilte M N, Celie J W, Wee P M, Beelen R H, van den Born J. Factors contributing to peritoneal tissue remodeling in peritoneal dialysis. Peritoneal dialysis international: journal of the International Society for Peritoneal Dialysis 2009; 29:605-17.
19. Contreras-Velazquez J C S, V. Jaramillo-Rodriguez, Y. Samaniego-Rios, L. I. Quinones-Perez, V. avila, M. Amato, D. Paniagua, R. Clinical outcomes and peritoneal histology in patients starting peritoneal dialysis are related to diabetic status and serum albumin levels. Kidney International Supplement 2008; 73 Supp 108:S34-41.
20. Nakayamaa M S, A; Numataa, M; Hosoyaa, T: Hyper-Vascular Change and Formation of Advanced Glycation Endproducts in the Peritoneum Caused by Methylglyoxal and the Effect of an Anti-Oxidant, Sodium Sulfite. American Journal of Nephrology 2003; 23:390-94.
21. Krediet R, Zweers M, van der Wal A, Struijk D. Neoangiogenesis in the peritoneal membrane. Peritoneal Dialysis International 2000; 20:S19-S25.
22. Harrison D A. The Jak/STAT pathway. Cold Spring Harb Perspect Biol 2012; 4.
23. Mohr A, Chatain N, Domoszlai T, et al. Dynamics and non-canonical aspects of JAK/STAT signalling. Eur J Cell Biol 2012; 91:524-32.
24. Leung J C, Chan L Y, Tang S C, Chu K M, Lai K N. Leptin induces TGF-beta synthesis through functional leptin receptor expressed by human peritoneal mesothelial cell. Kidney international 2006; 69:2078-86.
25. Devuyst O, Margetts P J, Topley N. The pathophysiology of the peritoneal membrane. Journal of the American Society of Nephrology: JASN 2010; 21:1077-85.
26. Pletinck A, Vanholder R, Veys N, Van Biesen W. Protecting the peritoneal membrane: factors beyond peritoneal dialysis solutions. Nat Rev Nephrol 2012; 8:542-550.
27. Fridman J S, Scherle P A, Collins R, et al. Selective inhibition of JAK1 and JAK2 is efficacious in rodent models of arthritis: preclinical characterization of INCB028050. J Immunol 2010; 184:5298-307.
28. Margetts P J, Bonniaud P. Basic mechanisms and clinical implications of peritoneal fibrosis. Peritoneal dialysis international: journal of the International Society for Peritoneal Dialysis 2003; 23:530-41.
29. Cordeiro A C, Carrero J J, Abensur H, Lindholm B, Stenvinkel P. Systemic and local inflammation in peritoneal dialysis: mechanisms, biomarkers and effects on outcome. Contrib Nephrol 2009; 163:132-9.
30. Zareie M, De Vriese A S, Hekking L H P, et al. Immunopathological changes in a uraemic rat model for peritoneal dialysis. Nephrology Dialysis Transplantation 2005; 20:1350-1361.
31. Albrektsson A, Bazargani F, Wieslander A, Braide M. Peritoneal dialysis fluid-induced angiogenesis in rat mesentery is increased by lactate in the presence or absence of glucose. ASAIO J 2006; 52:276-81.
32. Zareie M, Hekking L H, Welten A G, et al. Contribution of lactate buffer, glucose and glucose degradation products to peritoneal injury in vivo. Nephrology, dialysis, transplantation: official publication of the European Dialysis and Transplant Association—European Renal Association 2003; 18:2629-37.
33. Hekking L H P, Zareie M, Driesprong B A J, et al. Better Preservation of Peritoneal Morphologic Features and Defense in Rats after Long-Term Exposure to a Bicarbonate/Lactate-Buffered Solution. Journal of the American Society of Nephrology 2001; 12:2775-2786.
34. WITOWSKI J, KORYBALSKA K, WISNIEWSKA J, et al. Effect of Glucose Degradation Products on Human Peritoneal Mesothelial Cell Function. Journal of the American Society of Nephrology 2000; 11:729-739.
35. De Vriese A S, Flyvbjerg A, Mortier S, Tilton R G, Lameire N H. Inhibition of the Interaction of AGE-RAGE Prevents Hyperglycemia-Induced Fibrosis of the Peritoneal Membrane. Journal of the American Society of Nephrology 2003; 14:2109-2118.
36. Hendriks P M, Ho-dac-Pannekeet M M, van Gulik T M, et al. Peritoneal sclerosis in chronic peritoneal dialysis patients: analysis of clinical presentation, risk factors, and peritoneal transport kinetics. Peritoneal dialysis international: journal of the International Society for Peritoneal Dialysis 1997; 17:136-43.
37. Schwenger V, Morath C, Salava A, et al. Damage to the Peritoneal Membrane by Glucose Degradation Products Is Mediated by the Receptor for Advanced Glycation End-Products. Journal of the American Society of Nephrology 2006; 17:199-207.
38. Boulanger E, Grossin N, Wautier M P, Taamma R, Wautier J L. Mesothelial RAGE activation by AGEs enhances VEGF release and potentiates capillary tube formation. Kidney international 2006; 71:126-133.
39. Boulanger E, Wautier M-P, Wautier J-L, et al. AGEs bind to mesothelial cells via RAGE and stimulate VCAM-1 expression. Kidney international 2002; 61:148-156.
40. Combet S, Ferrier M L, Van Landschoot M, et al. Chronic uremia induces permeability changes, increased nitric oxide synthase expression, and structural modifications in the peritoneum. Journal of the American Society of Nephrology: JASN 2001; 12:2146-57.
41. Plum J, Hermann S, Fussholler A, et al. Peritoneal sclerosis in peritoneal dialysis patients related to dialysis settings and peritoneal transport properties. Kidney international. Supplement 2001; 78:S42-7.
42. Verger C, Luger A, Moore H L, Nolph K D. Acute changes in peritoneal morphology and transport properties with infectious peritonitis and mechanical injury. Kidney international 1983; 23:823-31.
43. Davies S J, Phillips L, Griffiths A M, Russell L H, Naish P F, Russell G I. What really happens to people on long-term peritoneal dialysis? Kidney international 1998; 54:2207-17.
44. Topley N. The cytokine network controlling peritoneal inflammation. Peritoneal Dialysis International 1995; 15:S35-S39.
45. Gotloib L, Shostack A, Bar-Sella P, Cohen R. CONTINUOUS MESOTHELIAL INJURY AND REGENERATION DURING LONG TERM PERITONEAL DIALYSIS. Peritoneal Dialysis International 1987; 7:148-156.
46. Selgas R, Bajo A, Jimenez-Heffernan J A, et al. Epithelial-to-mesenchymal transition of the mesothelial cell—its role in the response of the peritoneum to dialysis. Nephrology, dialysis, transplantation: official publication of the European Dialysis and Transplant Association—European Renal Association 2006; 21 Suppl 2:ii2-7.
47. Yanez-Mo M, Lara-Pezzi E, Selgas R, et al. Peritoneal dialysis and epithelial-to-mesenchymal transition of mesothelial cells. The New England journal of medicine 2003; 348:403-13.
48. Aroeira L S, Aguilera A, Sanchez-Tomero J A, et al. Epithelial to mesenchymal transition and peritoneal membrane failure in peritoneal dialysis patients: pathologic significance and potential therapeutic interventions. Journal of the American Society of Nephrology: JASN 2007; 18:2004-13.
49. Aroeira L S, Aguilera A, Selgas R, et al. Mesenchymal Conversion of Mesothelial Cells as a Mechanism Responsible for High Solute Transport Rate in Peritoneal Dialysis: Role of Vascular Endothelial Growth Factor. American Journal of Kidney Diseases 2005; 46:938-948.
50. Lopez-Cabrera M, Aguilera A, Aroeira L S, et al. Ex vivo analysis of dialysis effluent-derived mesothelial cells as an approach to unveiling the mechanism of peritoneal membrane failure. Peritoneal dialysis international: journal of the International Society for Peritoneal Dialysis 2006; 26:26-34.
51. Yung S, Chen X R, Tsang R C, Zhang Q, Chan T M. Reduction of perlecan synthesis and induction of TGF-beta1 in human peritoneal mesothelial cells due to high dialysate glucose concentration: implication in peritoneal dialysis. Journal of the American Society of Nephrology: JASN 2004; 15:1178-88.
52. Visser C E, Tekstra J, Brouwer-Steenbergen J J, et al. Chemokines produced by mesothelial cells: huGRO-alpha, IP-10, MCP-1 and RANTES. Clin Exp Immunol 1998; 112:270-5.
53. Welten A, Schalkwijk C, ter Wee P, Meijer S, van den Born J, Beelen R. Single exposure of mesothelial cells to glucose degradation products (GDPs) yields early advanced glycation end-products (AGEs) and a proinflammatory response. Peritoneal Dialysis International 2003; 23:213-221.
54. Zhu H, Naito M, Umezu H, et al. Macrophage differentiation and expression of macrophage colony-stimulating factor in murine milky spots and omentum after macrophage elimination. J Leukoc Biol 1997; 61:436-44.
55. Beelen R H, Oosterling S J, van Egmond M, van den Born J, Zareie M. Omental milky spots in peritoneal pathophysiology (spots before your eyes). Peritoneal dialysis international: journal of the International Society for Peritoneal Dialysis 2005; 25:30-2.
56. Lui S L, Yung S, Yim A, et al. A Combination of Biocompatible Peritoneal Dialysis Solutions and Residual Renal Function, Peritoneal Transport, and Inflammation Markers: A Randomized Clinical Trial. American journal of kidney diseases: the official journal of the National Kidney Foundation 2012.
57. Flessner M, Henegar J, Bigler S, Genous L. Is the peritoneum a significant transport barrier in peritoneal dialysis? Peritoneal dialysis international: journal of the International Society for Peritoneal Dialysis 2003; 23:542-9.
58. Johnson D W, Brown F G, Clarke M, et al. The effect of low glucose degradation product, neutral pH versus standard peritoneal dialysis solutions on peritoneal membrane function: the balANZ trial. Nephrology, dialysis, transplantation: official publication of the European Dialysis and Transplant Association—European Renal Association 2012.
59. Ni J, McLoughlin R M, Brodovitch A, et al. Nitric oxide synthase isoforms play distinct roles during acute peritonitis. Nephrology, dialysis, transplantation: official publication of the European Dialysis and Transplant Association—European Renal Association 2010; 25:86-96.
60. Okada H, Inoue T, Kanno Y, et al. Selective depletion of fibroblasts preserves morphology and the functional integrity of peritoneum in transgenic mice with peritoneal fibrosing syndromel. Kidney international 2003; 64:1722-1732.
61. Yu M A, Shin K S, Kim J H, et al. HGF and BMP-7 ameliorate high glucose-induced epithelial-to-mesenchymal transition of peritoneal mesothelium. Journal of the American Society of Nephrology: JASN 2009; 20:567-81.
62. Aguilera A, Aroeira L S, Ramirez-Huesca M, et al. Effects of rapamycin on the epithelial-to-mesenchymal transition of human peritoneal mesothelial cells. Int J Artif Organs 2005; 28:164-9.
63. De Vriese A S, Tilton R G, Mortier S, Lameire N H. Myofibroblast transdifferentiation of mesothelial cells is mediated by RAGE and contributes to peritoneal fibrosis in uraemia. Nephrology Dialysis Transplantation 2006; 21:2549-2555.
64. Oh K-H, Jung J Y, Yoon M O, et al. Intra-peritoneal interleukin-6 system is a potent determinant of the baseline peritoneal solute transport in incident peritoneal dialysis patients. Nephrology Dialysis Transplantation 2010; 25:1639-1646.
65. Schilte M N, Loureiro J, Keuning E D, et al. Long-term intervention with heparins in a rat model of peritoneal dialysis. Peritoneal dialysis international: journal of the International Society for Peritoneal Dialysis 2009; 29:26-35.
66. Fracasso A, Baggio B, Masiero M, et al. Effect of oral treatment with the glycosaminoglycan sulodexide on peritoneal transport in CAPD patients. Peritoneal Dialysis International 2003; 23:595-599.
67. Breborowicz A, Polubinska A, Moberly J, Ogle K, Martis L, Oreopoulos D. Hyaluronan modifies inflammatory response and peritoneal permeability during peritonitis in rats. American journal of kidney diseases: the official journal of the National Kidney Foundation 2001; 37:594-600.
68. Breborowicz A, Polubinska A, Simon M, Tam P, Wu G. N-Acetylglucosamine—an osmotic slute for peritoneal dialysis without inducing hyperinsulinemia. Blood Purif 2004; 22:183-7.
69. Breborowicz A, Polubinska A, Wu G, Tam P, Oreopoulos D G. N-acetylglucosamine reduces inflammatory response during acute peritonitis in uremic rats. Blood Purif 2006; 24:274-81.
70. Warnock D G H, S.; Bargman, J.; et al: Prospective safety study of bardoxolone methyl in patients with Type 2 diabetes mellitus, end-stage renal disease and peritoneal dialysis. Contributions to Nephrology 2012; 178:157-63.
71. Amiri F, Shaw S, Wang X, et al. Angiotensin II activation of the JAK/STAT pathway in mesangial cells is altered by high glucose. Kidney international 2002; 61:1605-16.
72. Huang J-S, Guh J-Y, Chen H-C, Hung W-C, Lai Y-H, Chuang L-Y. Role of receptor for advanced glycation endproduct (RAGE) and the JAK/STAT-signaling pathway in AGE-induced collagen production in NRK-49F cells. Journal of Cellular Biochemistry 2001; 81:102-113.
73. Satirapoj B, Wang Y, Chamberlin M P, et al. Periostin: novel tissue and urinary biomarker of progressive renal injury induces a coordinated mesenchymal phenotype in tubular cells. Nephrology Dialysis Transplantation 2012; 27:2702-2711.
74. Coutu D L, Wu J H, Monette A, Rivard G E, Blostein M D, Galipeau J. Periostin, a member of a novel family of vitamin K-dependent proteins, is expressed by mesenchymal stromal cells. J Biol Chem 2008; 283:17991-8001.
75. Mona L, Moch H. Periostin expression and epithelial-mesenchymal transition in cancer: a review and an update. Virchows Archiv 2011; 459:465-475.
76. Oka T, Xu J, Kaiser R A, et al. Genetic Manipulation of Periostin Expression Reveals a Role in Cardiac Hypertrophy and Ventricular Remodeling. Circulation Research 2007; 101:313-321.
77. Shao R, Bao S, Bai X, et al. Acquired expression of periostin by human breast cancers promotes tumor angiogenesis through up-regulation of vascular endothelial growth factor receptor 2 expression. Mol Cell Biol 2004; 24:3992-4003.
78. Kim B-Y, Olzmann J A, Choi S-i, et al. Corneal Dystrophy-associated R124H Mutation Disrupts TGFBI Interaction with Periostin and Causes Mislocalization to the Lysosome. Journal of Biological Chemistry 2009; 284:19580-19591.
79. Krediet R T. Dialysate cancer antigen 125 concentration as marker of peritoneal membrane status in patients treated with chronic peritoneal dialysis. Peritoneal dialysis international: journal of the International Society for Peritoneal Dialysis 2001; 21:560-7.
80. Pecoits-Filho R, Araújo M R T, Lindholm B, et al. Plasma and dialysate IL-6 and VEGF concentrations are associated with high peritoneal solute transport rate. Nephrology Dialysis Transplantation 2002; 17:1480-1486.
81. Opatrna S, Lysak D, Trefil L, Parker C, Topley N. Intraperitoneal IL-6 Signaling in Incident Patients Treated with Icodextrin and Glucose Bicarbonate/Lactate-Based Peritoneal Dialysis Solutions. Peritoneal Dialysis International 2012; 32:37-44.
82. Fehniger T A, Caligiuri M A. Interleukin 15: biology and relevance to human disease. Blood 2001; 97:14-32.
83. Grzegorzewska A E, Mlot M. Dialysate interleukin-15 concentration and ultrafiltration capacity in patients undergoing peritoneal dialysis. Advances in peritoneal dialysis. Conference on Peritoneal Dialysis 2003; 19:67-72.
84. Butcher J T, Norris R A, Hoffman S, Mjaatvedt C H, Markwald R R. Periostin promotes atrioventricular mesenchyme matrix invasion and remodeling mediated by integrin signaling through Rho/PI 3-kinase. Dev Biol 2007; 302:256-66.
85. Kruzynska-Frejtag A, Wang J, Maeda M, et al. Periostin is expressed within the developing teeth at the sites of epithelial-mesenchymal interaction. Dev Dyn 2004; 229:857-68.
86. Lai K N, Lai K B, Lam C W, Chan T M, Li F K, Leung J C. Changes of cytokine profiles during peritonitis in patients on continuous ambulatory peritoneal dialysis. American journal of kidney diseases: the official journal of the National Kidney Foundation 2000; 35:644-52.
87. Do J Y, Kim Y L, Park J W, et al. The effect of low glucose degradation product dialysis solution on epithelial-to-mesenchymal transition in continuous ambulatory peritoneal dialysis patients. Peritoneal dialysis international: journal of the International Society for Peritoneal Dialysis 2005; 25 Suppl 3:S22-5.
88. Mortier S, Lameire N, De Vriese A. Animal models in peritoneal dialysis research: a need for consensus. Peritoneal Dialysis International 2005; 25:16-24.
89. Suzuki K, Khanna R, Nolph K, Twardowski Z, Moore H. Expected white blood cell counts and differentials in a rat model of peritoneal dialysis. Peritoneal Dialysis International 1995; 15:142-146.

90. Peng Y M, Shu Z J, Xiao L, et al. A new non-uremic rat model of long-term peritoneal dialysis. Physiol Res 2011; 60:157-64.
91. Hirahara I, Kusano E, Yanagiba S, et al. PERITONEAL INJURY BY METHYLGLYOXAL IN PERITONEAL DIALYSIS. Peritoneal Dialysis International 2006; 26:380-392.
92. Wang T, Qureshi A R, Heimburger O, Waniewski J, Bergstrom J, Lindholm B. Daily exposure to dialysis fluid results in changes in peritoneal transport. Peritoneal dialysis international: journal of the International Society for Peritoneal Dialysis 1997; 17:379-86.
93. Mortier S, Faict D, Schalkwijk C G, Lameire N H, De Vriese A S. Long-term exposure to new peritoneal dialysis solutions: Effects on the peritoneal membrane. Kidney international 2004; 66:1257-1265.
94. Cavallini N, Braide M. Catheter patency and peritoneal morphology and function in a rat model of citrate-buffered peritoneal dialysis. Peritoneal dialysis international: journal of the International Society for Peritoneal Dialysis 2010; 30:602-10.
95. Kanjanabuch T, Siribamrungwong M, Khunprakant R, et al. Overnight mesothelial cell exfoliation: a magic tool for predicting future ultrafiltration failure in patients on continuous ambulatory peritoneal dialysis. Peritoneal dialysis international: journal of the International Society for Peritoneal Dialysis 2008; 28 Suppl 3:S107-13.
96. Lai K N, Lai K B, Szeto C C, et al. Dialysate cell population and cancer antigen 125 in stable continuous ambulatory peritoneal dialysis patients: their relationship with transport parameters. American journal of kidney diseases: the official journal of the National Kidney Foundation 1997; 29:699-705.
97. Brulez H F, Verbrugh H A. First-line defense mechanisms in the peritoneal cavity during peritoneal dialysis. Peritoneal dialysis international: journal of the International Society for Peritoneal Dialysis 1995; 15:S24-33; discussion S33-4.
98. Sakamoto N, Sugimura K, Kawashima H, et al. Influence of glucose and inflammatory cytokines on TGF-beta1 and CTGF mRNA expressions in human peritoneal mesothelial cells. International journal of molecular medicine 2005; 15:907-911.
99. Humphreys B D, Lin S-L, Kobayashi A, et al. Fate Tracing Reveals the Pericyte and Not Epithelial Origin of Myofibroblasts in Kidney Fibrosis. The American Journal of Pathology 2010; 176:85-97.
100. van den Berg B, Vink H. Glycocalyx perturbation: cause or consequence of damage to the vasculature? American Journal of Physiology—Heart and Circulatory Physiology 2006; 290:H2174-H2175.
101. Kanwar Y S, Linker A, Farquhar M G. Increased permeability of the glomerular basement membrane to ferritin after removal of glycosaminoglycans (heparan sulfate) by enzyme digestion. The Journal of Cell Biology 1980; 86:688-693.
102. Gotloib L, Shostack A, Jaichenko J. Ruthenium-red-stained anionic charges of rat and mice mesothelial cells and basal lamina: the peritoneum is a negatively charged dialyzing membrane. Nephron 1988; 48:65-70.
103. Yung S, Thomas G J, Stylianou E, Williams J D, Coles G A, Davies M. Source of peritoneal proteoglycans. Human peritoneal mesothelial cells synthesize and secrete mainly small dermatan sulfate proteoglycans. Am J Pathol 1995; 146:520-9.
104. Yung S, Coles G A, Williams J D, Davies M. The source and possible significance of hyaluronan in the peritoneal cavity. Kidney international 1994; 46:527-33.
105. Yung S, Hausser H, Thomas G, Schaefer L, Kresse H, Davies M. Catabolism of newly synthesized decorin in vitro by human peritoneal mesothelial cells. Peritoneal dialysis international: journal of the International Society for Peritoneal Dialysis 2004; 24:147-55.
106. Zuurbier C J, Demirci C, Koeman A, Vink H, Ince C. Short-term hyperglycemia increases endothelial glycocalyx permeability and acutely decreases lineal density of capillaries with flowing red blood cells. Journal of Applied Physiology 2005; 99:1471-1476.
107. Gronski T J, Martin R L, Kobayashi D K, et al. Hydrolysis of a Broad Spectrum of Extracellular Matrix Proteins by Human Macrophage Elastase. Journal of Biological Chemistry 1997; 272:12189-12194.
108. Guo Q, Peng W, Cheng H, Ye R, Lindholm B, Wang T. Hyaluronan preserves peritoneal membrane transport properties. Peritoneal Dialysis International 2001; 21:136-142.
109. Wang T, Cheng H H, Heimburger O, Waniewski J, Bergstrom J, Lindholm B. Hyaluronan prevents the decreased net ultrafiltration caused by increased peritoneal dialysate fill volume. Kidney international 1998; 53:496-502.
110. Flessner M F, Choi J, Vanpelt H, et al. Correlating structure with solute and water transport in a chronic model of peritoneal inflammation. Am J Physiol Renal Physiol 2006; 290:F232-40.
111. Sasaki N, Higashi N, Taka T, Nakajima M, Irimura T. Cell Surface Localization of Heparanase on Macrophages Regulates Degradation of Extracellular Matrix Heparan Sulfate. The Journal of Immunology 2004; 172:3830-3835.
112. Suassuna J H, Das Neves F C, Hartley R B, Ogg C S, Cameron J S. Immunohistochemical studies of the peritoneal membrane and infiltrating cells in normal subjects and in patients on CAPD. Kidney international 1994; 46:443-54.
113. Sawai A, Ito Y, Mizuno M, et al. Peritoneal macrophage infiltration is correlated with baseline peritoneal solute transport rate in peritoneal dialysis patients. Nephrology Dialysis Transplantation 2011; 26:2322-2332.
114. Duman S, Sen S. Technical aspects in studying peritoneal morphology in animal models of peritoneal dialysis. Peritoneal dialysis international: journal of the International Society for Peritoneal Dialysis 2009; 29 Suppl 2:S40-4.
115. Zareie M, Keuning E D, ter Wee P M, Beelen R H, van den Born J. Peritoneal dialysis fluid-induced changes of the peritoneal membrane are reversible after peritoneal rest in rats. Nephrology, dialysis, transplantation: official publication of the European Dialysis and Transplant Association—European Renal Association 2005; 20:189-93.
116. Moriishi M, Kawanishi H, Tsuchiya S. Impact on peritoneal membrane of use of icodextrin-based dialysis solution in peritoneal dialysis patients. Advances in peritoneal dialysis. Conference on Peritoneal Dialysis 2006; 22:24-28.
117. Jones P A, Werb Z. Degradation of connective tissue matrices by macrophages. II. Influence of matrix composition on proteolysis of glycoproteins, elastin, and collagen by macrophages in culture. J Exp Med 1980; 152:1527-36.
118. Pahl M V, Vaziri N D, Yuan J, Adler S G. Upregulation of monocyte/macrophage HGFIN (Gpnmb/Osteoactivin) expression in end-stage renal disease. Clin J Am Soc Nephrol 2010; 5:56-61.

119. Kramer R H, Vogel K G, Nicolson G L. Solubilization and degradation of subendothelial matrix glycoproteins and proteoglycans by metastatic tumor cells. J Biol Chem 1982; 257:2678-86.

120. Kim Y L, Kim S H, Kim J H, et al. Effects of peritoneal rest on peritoneal transport and peritoneal membrane thickening in continuous ambulatory peritoneal dialysis rats. Peritoneal dialysis international: journal of the International Society for Peritoneal Dialysis 1999; 19 Suppl 2:S384-7.

121. Strauss R, Li Z Y, Liu Y, et al. Analysis of epithelial and mesenchymal markers in ovarian cancer reveals phenotypic heterogeneity and plasticity. PLoS One 2011; 6:e16186.

122. Heusinkveld M, de Vos van Steenwijk P J, Goedemans R, et al. M2 macrophages induced by prostaglandin E2 and IL-6 from cervical carcinoma are switched to activated M1 macrophages by CD4+ Th1 cells. J Immunol 2011; 187: 1157-65.

123. Porcheray F, Viaud S, Rimaniol A C, et al. Macrophage activation switching: an asset for the resolution of inflammation. Clin Exp Immunol 2005; 142:481-9.

124. Fujisaka S, Usui I, Bukhari A, et al. Regulatory mechanisms for adipose tissue M1 and M2 macrophages in diet-induced obese mice. Diabetes 2009; 58:2574-82.

Example 2

JAK Inhibition Reduces Mesothelial Cell Death In Vitro that is Induced by Toxicity from Exposure to Peritoneal Dialysis Fluid Methods: Met-5A cells were incubated with heated peritoneal dialysis fluid (PDF), filtered (F-PDF) and Low GDP-FPDF with or without 250 nM JAK inhibitor (Jaki) P6, and cells were harvested at 24 h for measuring cleaved caspase-3 by Western blot as an indication of cell death. 100 μg of cell lysate was separated on a 8-16% SDS polyacrylamide gel. Proteins were transferred onto a nitrocellulose membrane, blocked with 5% BSA in TBST and incubated with primary anti-cleaved caspase-3 antibody (1; 1000, Cell Signaling) overnight. After incubation with a HRP conjugated anti-rabbit antibody (1:1500, GE Healthcare UK Ltd, Piscataway, N.J.), protein bands were visualized by chemiluminiscence (Thermo Scientific). GAPDH serves as an internal control.

Figure 5N:
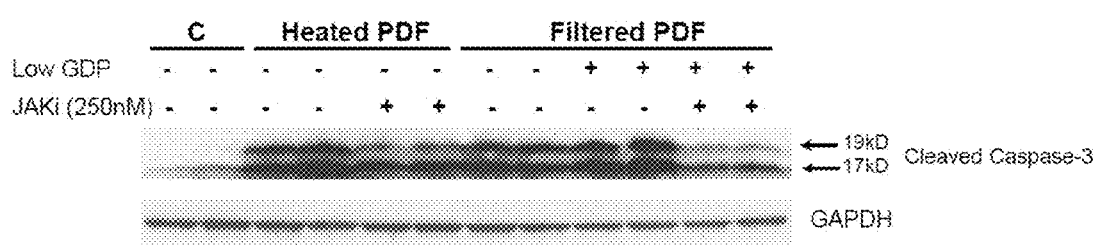

Results: The results are shown in FIG. 5N. Exposure to any PDF induces caspase-3 cleavage, which is reduced in the presence of Jaki P6.

Conclusion: JAK inhibition reduces mesothelial cell death in vitro that is induced by toxicity from exposure to peritoneal dialysis fluid.

Example 3

Periostin

Novel Tissue and Urinary Biomarker of Progressive Renal Injury Induces a Coordinated Mesenchymal Phenotype in Tubular Cells Abstract Background: Periostin acts as an adhesion molecule during bone formation. Knowledge of expression of periostin in peritoneal injury is still scanty.

Methods: Inventors investigated periostin function and expression in vitro of distal nephron tubular cells (DT), in Sprague-Dawley rats after 5/6 nephrectomy (Nx), in DBA2J mice after streptozotocin-induced diabetes (SZ-DM), and in the urine of chronic peritoneal injury (CKD) patients.

Results: Periostin was identified by microarray and confirmed by real-time PCR in renal tissue after 5/6Nx, and SZ-DM demonstrating generalizability of the periostin increment in renal injury. Periostin was expressed predominantly in DT and in tubule cells shed into the lumen. In affected DT after 5/6Nx, periostin expression appeared de novo, the epithelial cell adhesion molecule E-cadherin became undetectable, and tubule cells displayed the mesenchymal marker proteins fibroblast specific protein-1 (FSP1) and matrix metalloproteinase-9 (MMP9). To assess whether periostin plays a direct role in renal tubular epithelial mesenchymal transition (EMT), inventors overexpressed periostin in cultured DT. Overexpression dramatically increased MMP9 and FSP1 protein, and decreased E-cadherin protein expression. In addition, the effect of periostin on the renal tubular EMT was also blocked by periostin siRNA transfection. Urine periostin excretion increased over time after 5/6Nx, and it was also excreted in the urine of CKD patients. Urine periostin ELISA at a cutoff value of 32.66 pg/mg creatinine demonstrated sensitivity and specificity for distinguishing patients with progressive CKD from healthy people (92.3%, and 95.0%, respectively).

Conclusions: These data demonstrate that periostin is a mediator and marker of EMT, and a promising tissue and urine biomarker for peritoneal injury in experimental models and in clinical renal disease.

Introduction

The aim of the present study was to investigate periostin expression and function in animal models of peritoneal injury and in CKD patients.

Subjects and Methods

Animals

Sprague Dawley rats (N=18) underwent 5/6nephrectomy (Nx) (N=9) by unilateral Nx and ligation of 2/3 of the vessels to the contralateral kidney or sham Nx. Rats were sacrificed at 2 days, 2 weeks, and 4 weeks after surgery. Diabetes was induced in DBA2J mice by intraperitoneal injection of streptozotocin 40 mg/kg/day for 5 days as previously described with minor modifications.[15] At 2 months, renal tissues were harvested. DBA2J mice were subjected to unilateral ureteral obstruction (UUO) of left kidney and renal tissues were harvested at 5 and 14 days. All procedures were performed in accordance with the guidelines established by the National Research Council Guide for the Care and Use of Laboratory Animals.

Gene Array Analysis

Affymetrix Gene Chip 230_2 expression analysis was used to compare the transcription profiles between normal kidneys and remnant kidney (RK) at 2 days, 2 weeks and 4 weeks after 5/6Nx. Total RNA from 3 RK at each time point and 3 normal kidneys were labeled and hybridized to Affymetrix Gene Chips. Data were expressed as the average differences between the perfect match and mismatch probes for the periostin gene.

Collection of Human Urine

CKD subjects were recruited from an outpatient Nephrology clinic. Random biological samples were collected from proteinuric CKD patients (n=21) and non proteinuric CKD patients with PKD (n=5) and stored at −80° C. with protease inhibitors until assayed. Control samples were collected from healthy volunteers (n=20) who have normal renal function.

Quantitative Real Time-Polymerase Chain Reaction (RT-PCR) Analysis

Total RNA was isolated from rat control kidneys and RK at 2 days, 2 weeks and 4 weeks after 5/6Nx and DBA2J mice control kidneys and streptozotocin-induced diabetes (SZ-DM) at 2 months. RT-PCR with relative quantification of periostin copy number in relation to 18s ribosomal RNA transcripts was carried out using the following primers: periostin forward TGGTGTTGTCCATGTCATCGA (SEQ ID NO:1); and periostin reverse TGTGAAGTGACCGTCTCTTCCA (SEQ ID NO:2). All PCRs were run in an ABI 7900 Sequence Detection System (Applied Biosystems).

Immunohistochemistry

Four micron sections of formalin-fixed, paraffin-embedded tissue were deparaffinized and rehydrated. Endogenous peroxidase activity was quenched by incubating the slides in endogenous enzyme block solution, and subsequently at 4° C. for overnight with the primary polyclonal periostin antibody, fibroblast specific protein-1 (FSP1) antibody and matrix metalloproteinase-9 (MMP9) antibody. Next, the sections were incubated with dextran polymer conjugated with horseradish peroxidase and affinity isolated immunoglobulin for 30 minutes at room temperature.

Immunofluorescence

Deparaffinized rat kidney sections prepared as described were double labeled with a primary rabbit polyclonal periostin antibody and either fluorescence-conjugated peanut agglutinin (PNA) lectin antibody specific for distal nephron tubules (DT), fluorescence-conjugated *phaseolus vulgaris* erythroagglutinin (PHA-E) lectin antibody specific for proximal nephron tubules, and/or FITC-conjugated monoclonal E-cadherin antibody. In addition, using serial sections and PNA as a marker of DT, inventors compared the localization of periostin and E-cadherin in the DT. Indirect primary antibody was followed with goat anti-rabbit IgG conjugated to Texas Red.

Immunoblotting Analysis

Frozen kidney tissue and cell lysates were standardized by protein concentration, and a total of 30-100 μg of protein per well was loaded. Spot urine was collected from rats, patients, and healthy volunteers. Two percent of the urinary volume for each rat sample and 0.03 ml urine for each human sample was subjected to immunoblotting analysis. The procedure was done with a standard protocol as described previously.[16]

Urine Periostin Analysis by ELISA 96-well microplates were coated overnight with 1 μg/ml (0.1 μg per well) of anti-periostin antibody. Plates were washed three times with 0.05% Tween 20 in PBS then blocked with Reagent Diluent for at least one hour. 100 μl of all standards and patient samples was added to the 96-well plate and incubated for 2 hours. After a 1 hours incubation with a rabbit polyclonal antibodies to periostin, 20 minutes incubation with dextran polymer conjugated with horseradish peroxidase, and 20 minutes incubation with substrate solution, stop solution was added to each well. Periostin absorbances were calculated by making measurements at 450 nm and correcting for plate artifact at 570 nm. Periostin concentrations were calculated based on a log-transformed standard curve.

Urine Neutrophil Gelatinase-Associated Lipocalin (NGAL) Analysis by ELISA

The urine NGAL ELISA was performed using a commercially available assay (NGAL Rapid ELISA Kit 037; Bioporto, Grusbakken, Denmark) that specifically detects urine NGAL. The assay was performed as per the manufacturer's protocol.

Generation of Periostin-Producing Mouse Distal Convoluted Tubule (MDCT) Cells and RNA Interference Full-length mouse periostin cDNA was subcloned into a pCMV-SPORT6 (Thermo Scientific, Huntsville, Ala.). All the plasmids were purified with the Qiagen Midiprep kit. One day before transfection experiment, $6 \times 10^5$ immortalized MDCT cells, kindly provided by Dr. Peter Friedman, were plated on each well of 60 mm culture dish overnight. Confluent cells (80-90%) were then transfected with the periostin construct or vector control. For knockdown of periostin expression by using RNA interference technique, cells were co-transfected with mouse periostin plasmid and SureSilencing siRNA plasmids for mouse periostin by using FuGENE HD transfection reagent, according to the manufacturer's instruction. After transfection for 24 hours, cells were lysed and protein levels were determined by immunobloting.

Statistical Analysis

Statistical analysis was performed using SPSS, version 15. Either a two-sample t test or Mann-Whitney rank sum test was used for continuous variables. For multiple comparisons, ANOVA was used followed by the least significance difference test. Spearman correlation coefficients were used as appropriate to test correlations between urine periostin and other variables. Receiver operating characteristics (ROC) analysis was used to calculate the area under the curve (AUC) for periostin and NGAL and to find the best cut-off values for identifying the CKD. A $P \leq 0.05$ was considered statistically significant.

Results

Overexpressed Periostin Gene Following Renal Injury in the RK Model

Microarray Gene Set Enrichment Analysis (GSEA, Cambridge, Mass.) showed that gene expression of periostin was significantly up-regulated in the RK inclusive of the necrotic areas: 21.91-fold at day 2, 13.32-fold at week 2, and 14.46-fold at week 4 when compared with control kidneys. To confirm the microarray observation, and to determine if it is expressed exclusively in the infarct region, inventors additionally examined the expression of periostin mRNA in separate RK tissues in which the infarcted region was excised. As shown in FIG. 6A, RT-PCR revealed that there was a significant difference in mRNA expression of periostin in the RK: 3.84-fold at day 2 (P=0.025), 9.57-fold at week 2 (P=0.015), and 11.05-fold at week 4 (P=0.046) compared with control kidneys. Thus, the examination of periostin mRNA in viable RK tissue without infarcted tissue unmasked a progressive increase seen in injured renal parenchyma after 5/6Nx.

Renal Periostin Expression Increased Over Time in the RK Model

Figure 6C:
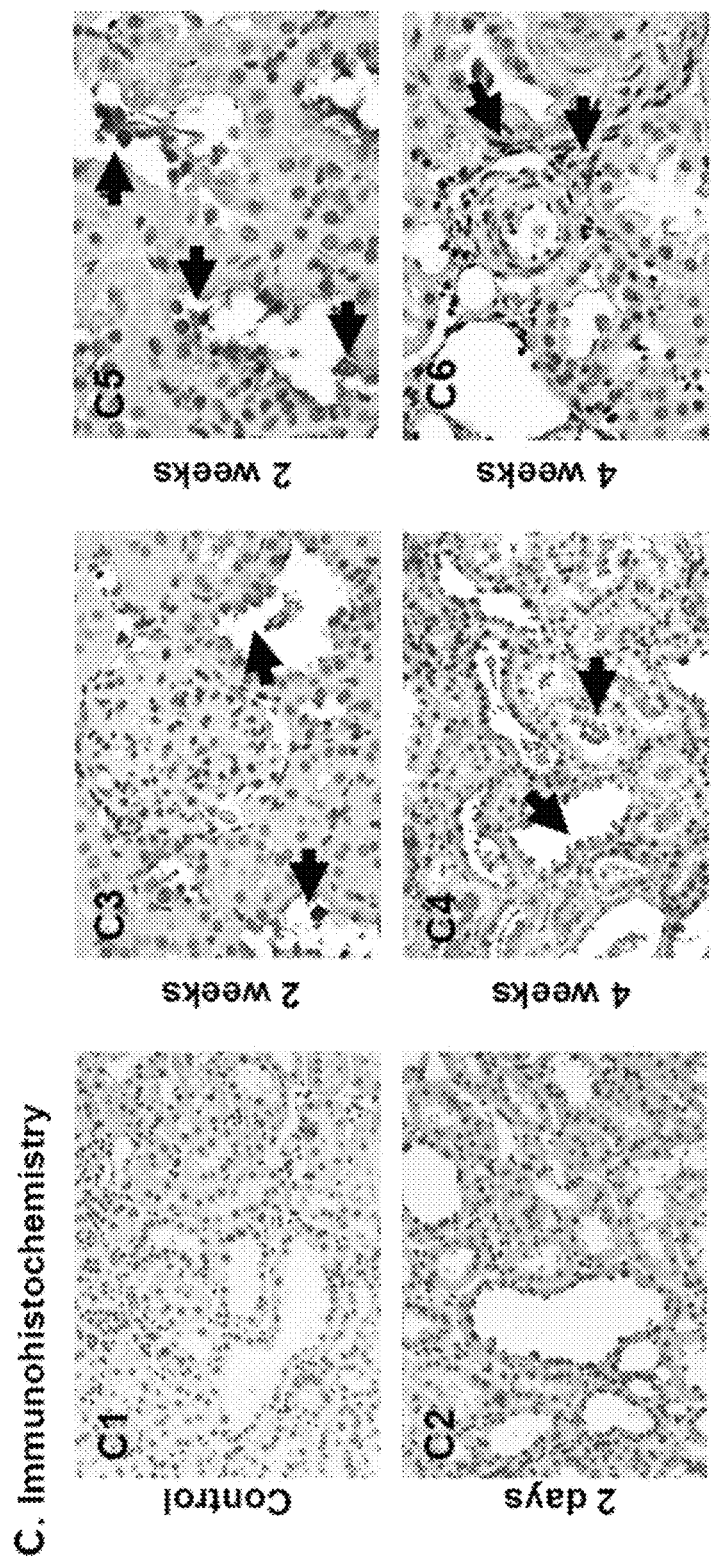

Immunoblotting and immunohistochemical analyses were performed on RK tissue after 5/6Nx compared to control kidneys to determine periostin protein expression. FIG. 6B shows increase in renal periostin/β-actin ratio each time point after 5/6Nx compared to controls (P<0.05). As shown in FIG. 6C staining of kidney sections of RK at all times demonstrated periostin expression predominantly in tubular cell cytoplasm, particularly in the apical aspects, but there was no periostin present in control cortical kidney. Detached tubular cells and cytoplasmic cell fragments sloughed into tubular lumina frequently were positive for periostin. The intensity of the tubular cell staining increased between 2 days and 2 weeks after 5/6Nx and remained at 4 weeks. RK had also periostin positive interstitial cells which frequently were in the periadventitial area around arterioles. Thus, these data confirmed that the mRNA changes observed after 5/6Nx were translated into increased protein expression in tubules in the non-infarcted RK.

Overexpression of Renal Periostin in SZ-DM, and UUO

Figure 7C:
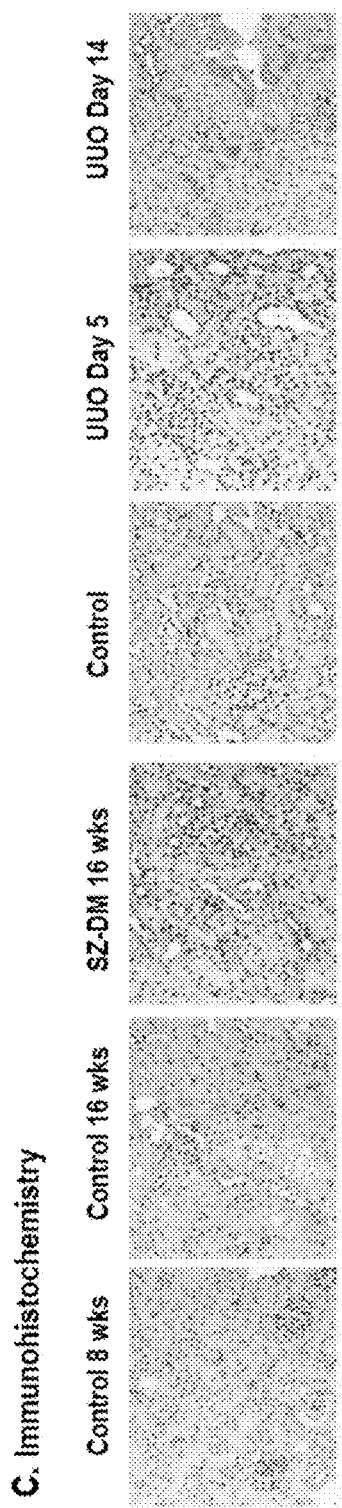

Periostin was measured by RT-PCR in renal tissue from DBA2J mice 2 months after SZ or diluent injections. FIG. 7A shows a 2.66-fold increase in periostin mRNA in the renal tissue of SZ-DM mice compared to controls (P=0.008). Significantly increased periostin expression was also detected by immunoblotting analysis in SZ-DM renal tissue compared with controls (FIG. 7B). As shown in FIG. 7C staining of kidney sections of SZ-DM and UUO demonstrated that prominent periostin was identified diffusely in tubular cell cytoplasm. Therefore, these data demonstrated that renal periostin also increased in a peritoneal injury model lacking infarction.

Periostin is Expressed in DT

As shown in FIG. 8, periostin was expressed in the cytoplasm of tubular epithelial cells that also stained positively for PNA lectin, indicating periostin expression in DT. There was no periostin identified in nephron segments stained with the proximal tubular lectin marker PHA-E. Thus periostin localized to the DT in the RK.

Figure 9A:
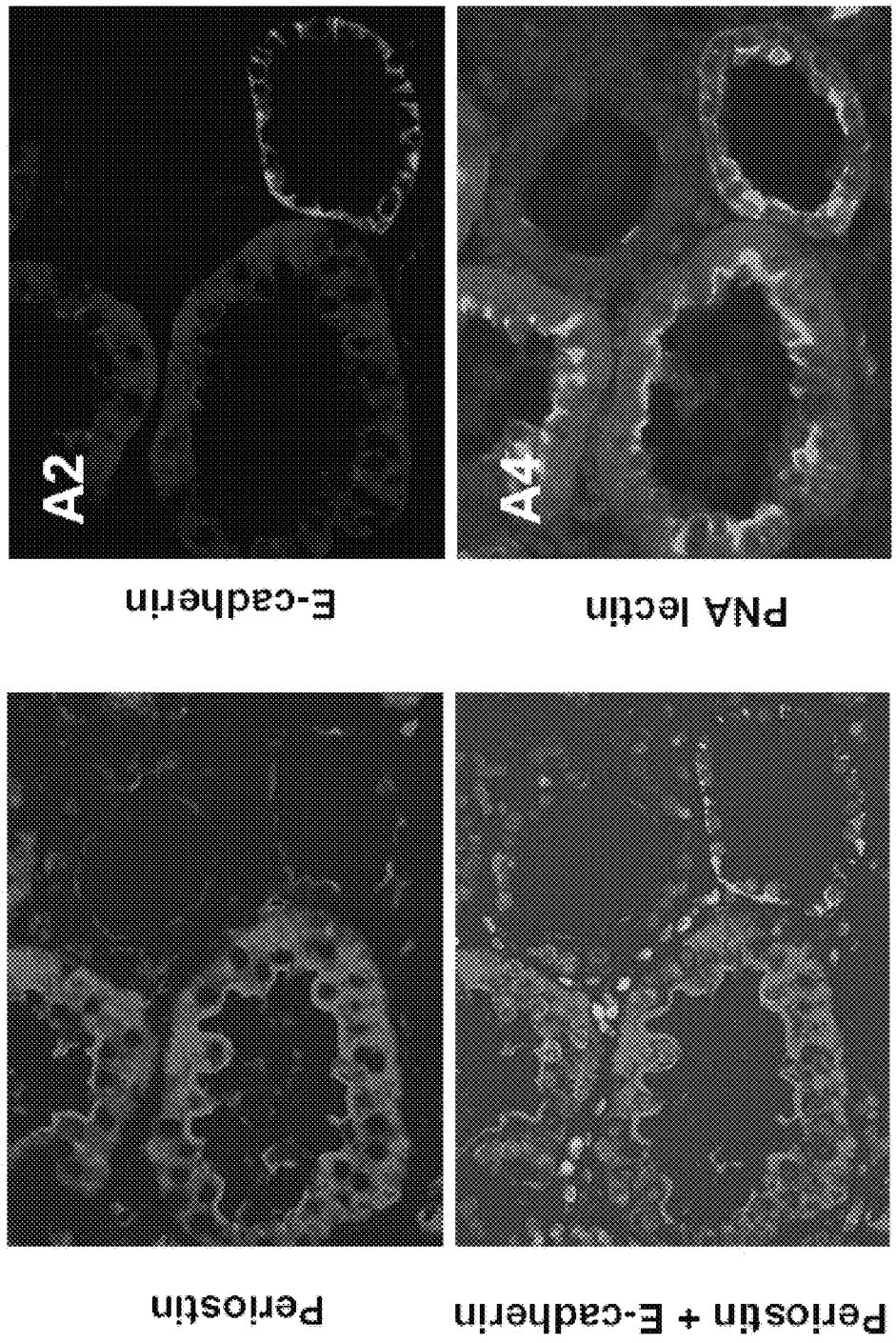
FIG. 9A-B. Periostin induces EMT phenotype. (A) E-cadherin expression is lost in distal nephron tubules expressing cytoplasmic periostin after 5/6Nx. The serial sections show virtually mutually exclusive immunofluorescence staining patterns for cytoplasmic periostin (red, A1) and E-cadherin (green, A2) in RK tissues 4 weeks after 5/6Nx. The section was counterstained with DAPI to visualize the cell nuclei and the tubules (merge, A3). Sequential sections also show that tubules expressing either periostin or E-cadherin both continued to express PNA lectin (A4), demonstrating that both are being expressed in distal nephron tubules. (B) Periostin, FSP1, and MMP9 are co-expressed in RK 2 days, 2 weeks, and 4 weeks after 5/6Nx. Serial sections of remnant kidney were stained for Periostin (B1, B4, B7, B10), FSP1 (B2, B5, B8, B11), and MMP9 (B3, B6, B9, B12) at all time points after 5/6Nx; 2 days (B1-3); 2 weeks (B4-6); and 4 weeks (B7-12) B1-9: Staining of MMP9 and FSP1 showed co-localization with periostin in renal tubular epithelium, and in luminal sloughed tubular cells and cytoplasmic fragments at all times after 5/6Nx. Cell and luminal cellular debris stain for all three proteins at 2 weeks (arrows) (Original magnification: 600×). B10-12: Interstitial cells in the 4 week remnant kidney also stain for periostin, FSP1 and MMP9 (arrows) (Original magnification 400×).

Disappearance of the Tight Junction Protein E-Cadherin in DT Expressing Periostin Using serial sections, immunofluorescence analysis of the RK demonstrated that DT retained their affinity for PNA lectin whether the tubules did or did not express periostin. However, in these PNA lectin-positive DT, the expression of E-cadherin and periostin were virtually mutually exclusive (FIG. 9A). These studies demonstrated an association between the appearance of periostin in DT in the RK concomitant with the disappearance of the DT protein E-cadherin, the latter a marker of the tubular differentiated state and a transmembrane protein responsible for cell-cell adhesion.

Figure 9B:
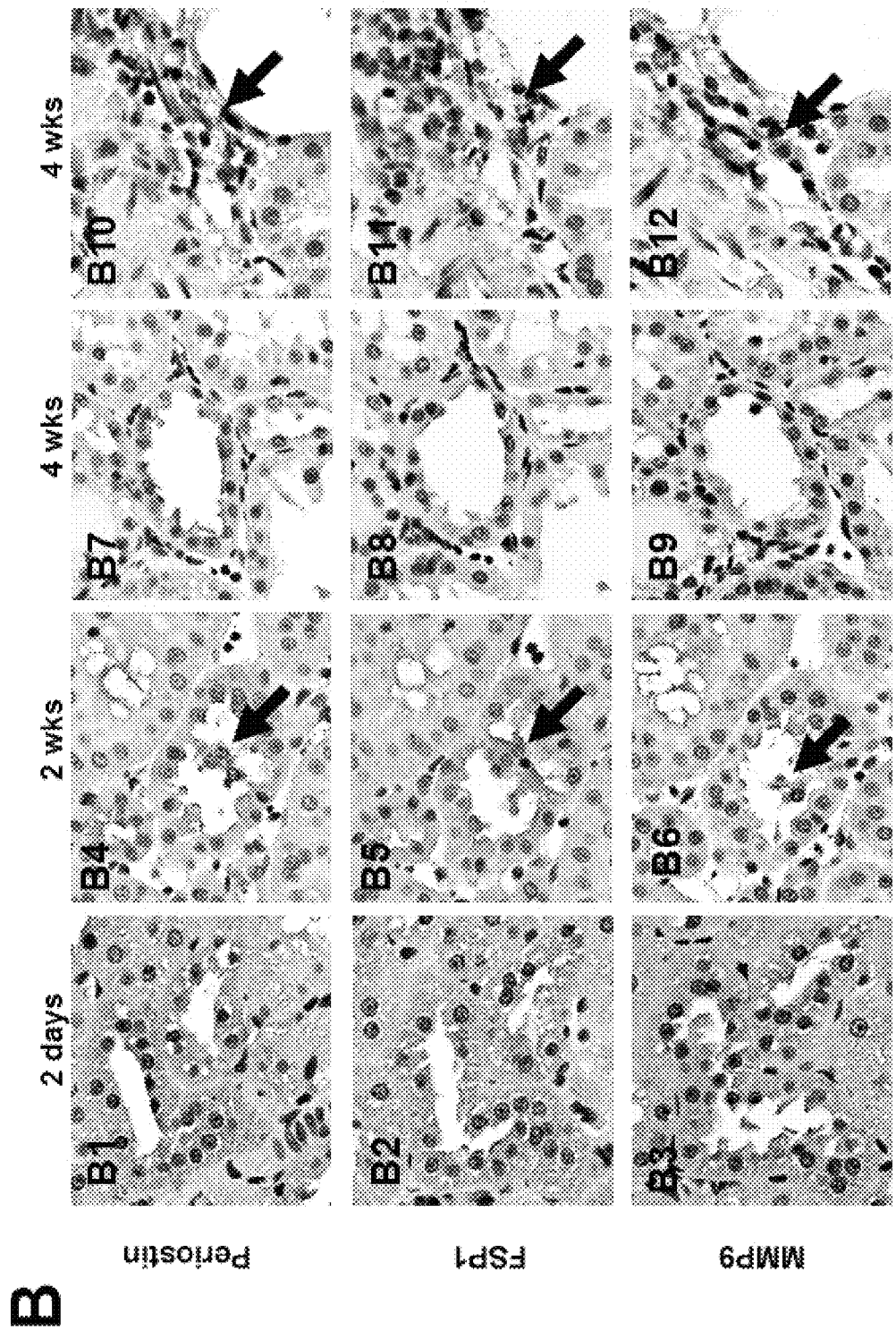

Periostin Associates with the Appearance of Renal Tubular Epithelial Mesenchymal Transition (EMT) Markers To study EMT, tissues were stained for FSP1, a cytoplasmic marker of epithelium undergoing mesenchymal transition, and MMP9, a protein involved in the turnover of extracellular matrix in renal tissue remodeling. These immunohistochemical studies revealed co-staining of MMP9 and FSP1 with periostin in affected DT cells, including sloughed cells and cytoplasmic fragments in tubular lumina, at all time points after 5/6Nx (FIG. 9B). There was staining of interstitial cells for periostin, FSP1 and MMP9 at 2 weeks with more extensive interstitial staining at 4 weeks. These studies demonstrate an association between periostin expression and the appearance of specific proteins in renal tubule indicating EMT.

In Vitro Periostin Induces Renal Tubular Mesenchymal Phenotype

Figure 10A:
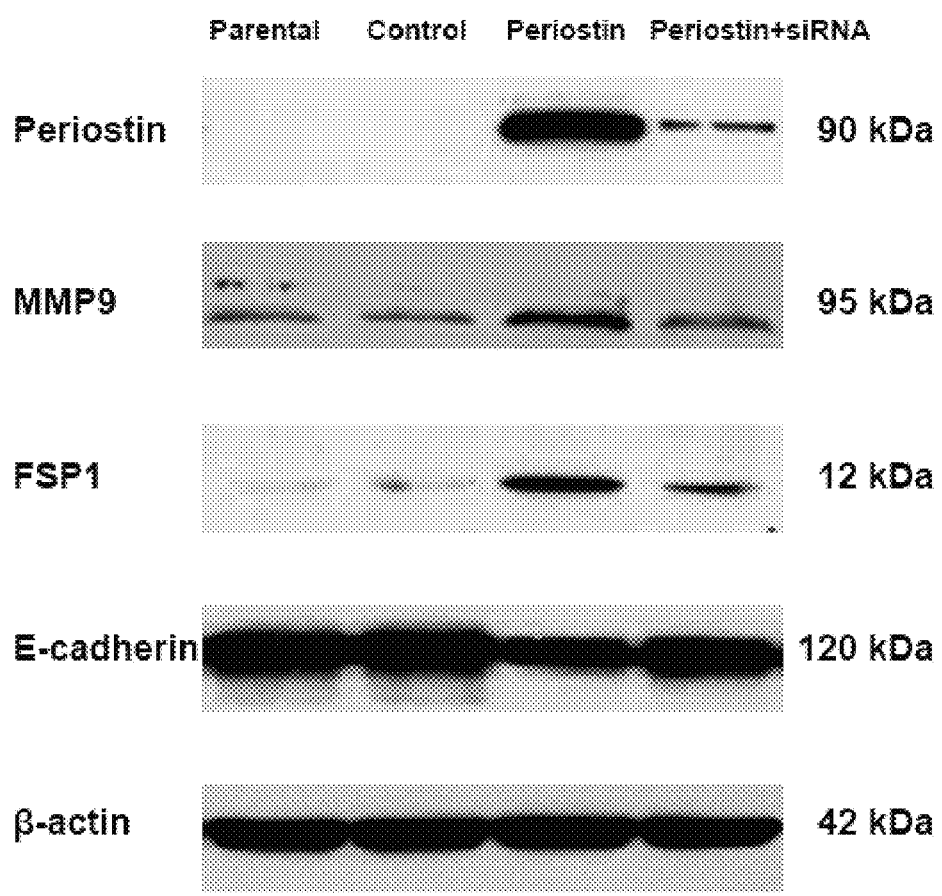
FIG. 10A-B. (A) Periostin-producing cells increase expression of EMT markers. Cell lysates from parental cells, transfected empty vector cells (control), transfected periostin vector cells and co-transfected periostin with SureSilencing siRNA vector cells were employed to examine MMP9, FSP1, and E-cadherin expression. (B) Bar graph showing results normalized to β-actin. MDCT cells expressing periostin dramatically increased MMP9 and FSP1 expression, a hallmark for mesenchymal cell. E-cadherin expression was also decreased by the periostin transgene in the cells. Co-transfected periostin and SureSilencing siRNA vector cells expressed reduced levels of periostin protein. Reduced periostin expression resulted in a restoration of E-cadherin and partial reduction of MMP9 and FSP1 expression. * P<0.05 vs. parental, control and periostin+siRNA group.
Figure 10B:
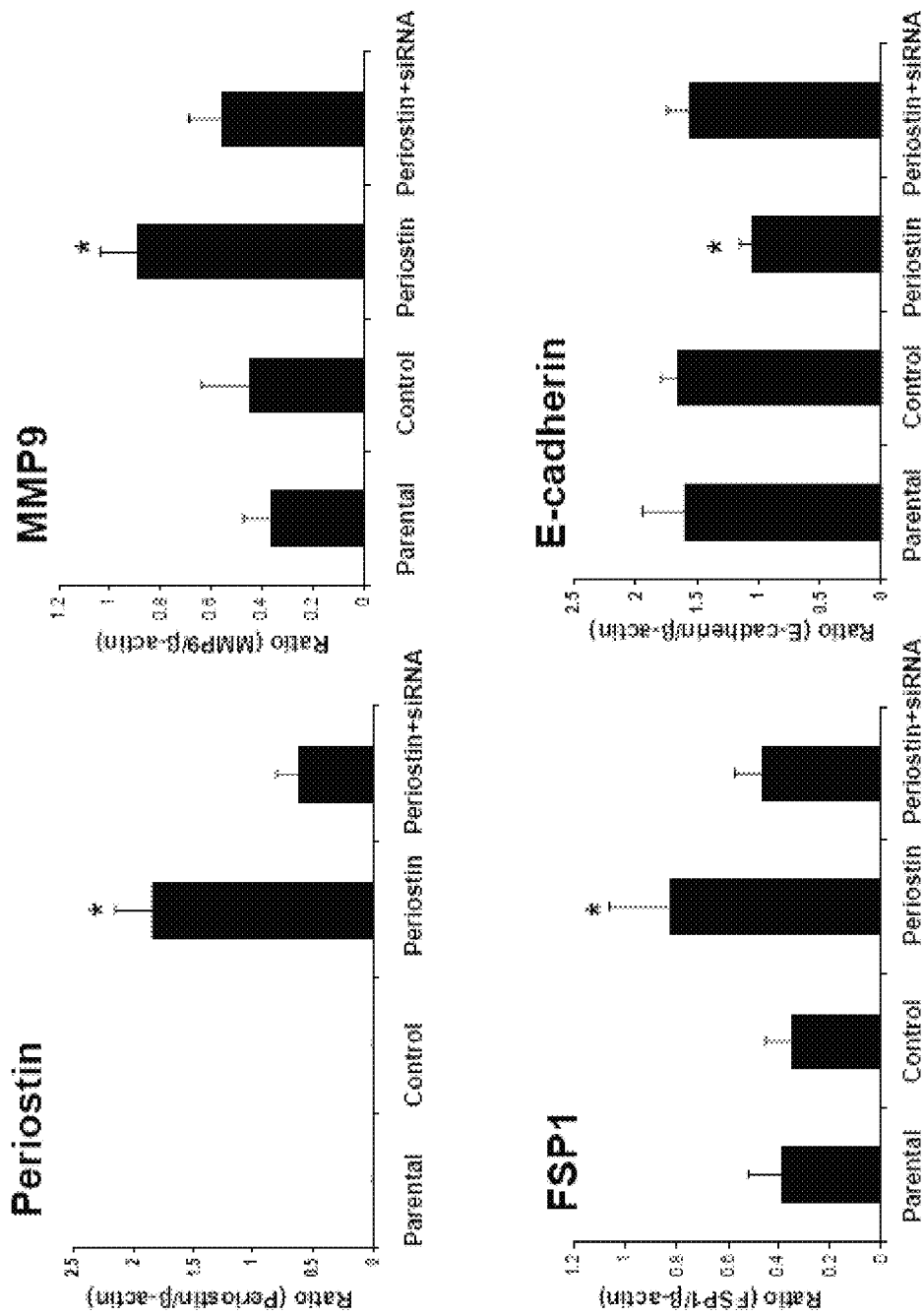

We used a transfection system to introduce the periostin cDNA into MDCT cells. MDCT cells ectopically expressing periostin dramatically increased MMP9 and FSP1 expression, a hallmark for mesenchymal cells. The level of MMP9 and FSP1 in parental MDCT cells and vector control cells was barely detectable. In contrast, expression of E-cadherin tight junction was strikingly decreased in periostin-producing cells (FIG. 10). Gene knockdown with siRNA was next applied to analyze the function of periostin on renal tubular EMT. MDCT cells were co-transfected with the periostin cDNA and siRNA, and the periostin protein level was obviously reduced. The effect of periostin on the renal tubular MMP9 and FSP1 generation and E-cadherin reduction was blocked by periostin siRNA transfection (FIG. 10). In aggregate, the data demonstrate that periostin expressed by MDCT cells drives the cells to undergo EMT.

Urinary Periostin Excretion Progressively Increased Over Time in the RK Model

Figure 11A:
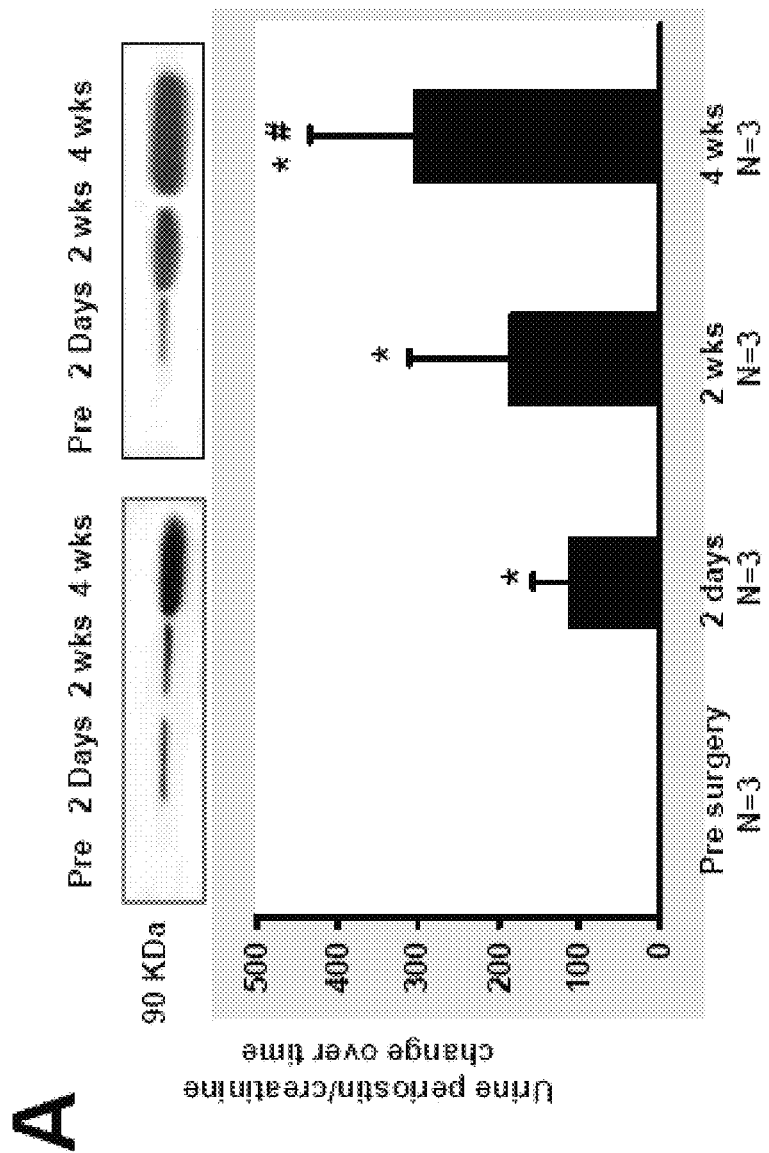
FIG. 11A-B. Urine periostin excretion rate increase after 5/6Nx in the RK model of progressive renal injury and in patients with proteinuric renal diseases and non-proteinuric renal disease. (A) Western blotting analysis for urine periostin was performed on individual rats prior to 5/6 Nx and after 2 days, 2 weeks, and 4 weeks (n=3 at each time point). Each lane was loaded with 2% of the total urinary flow rate for each rat sample. Urine creatinine was measured and used to control for concentration. Representative Western blots are shown. Experiments were performed in triplicate. * P<0.05 vs. pre surgery group, # P<0.05 vs. 2 days after 5/6Nx group. (B) In lightly centrifuged urine treated and stored with protease inhibitors, then thawed for the assay, 90 kDa urine periostin was detectable in patients with various proteinuric glomerular diseases, but not in controls (0.03 ml urine). With urine collected identically, in patients with non-proteinuric PKD but not in controls, 90 kDa urine periostin is also clearly detectable. C, control; DN, Diabetic nephropathy; LN, Lupus nephritis; FSGS, Focal and segmental glomerulosclerosis; PKD, Polycystic kidney disease.

FIG. 11A shows the time course for the urine periostin after 5/6Nx in a longitudinal experiment in which urine was collected from the same animals serially until their sacrifice at 4 weeks. Urine periostin was undetectable during the control period prior to 5/6Nx. There were significant incremental increases in urine periostin excretion over time after 5/6Nx. These data show that urine periostin distinguished healthy from injured kidney in a categorical fashion, and excretion increased over time with progressive chronicity of injury.

Human Urine Periostin is Detectable by Immunoblotting in CKD Patients

Figure 11B:
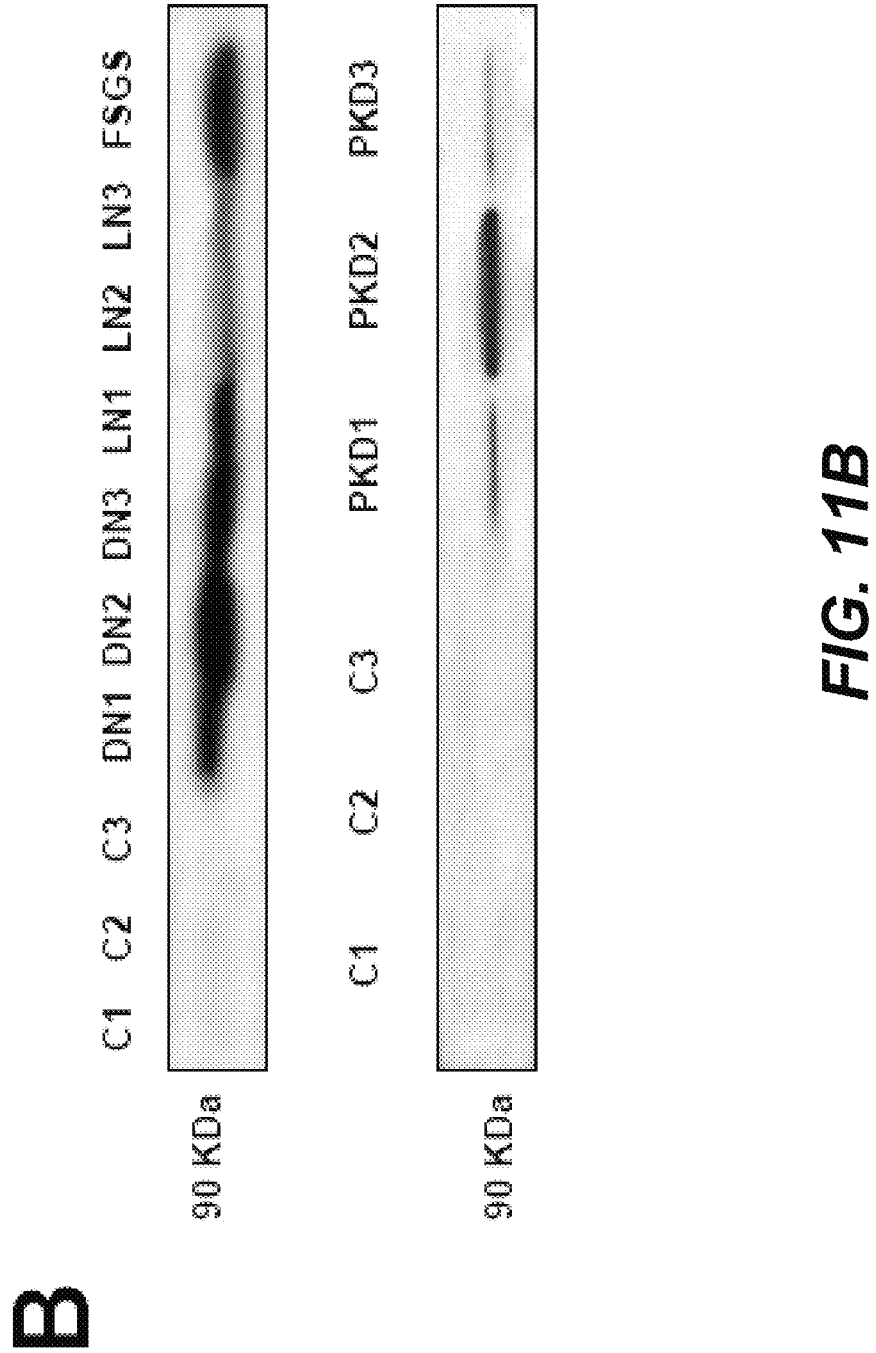

In FIGS. 11B-C, urine periostin is clearly detectable both in the proteinuric and non-proteinuric CKD patients. The appearance of urine periostin in CKD patients but not in healthy controls underscores its value as a potential biomarker for peritoneal injury in proteinuric and non-proteinuric conditions.

Using a quantitative ELISA, urine periostin is higher in proteinuric and non-proteinuric CKD patients than in healthy controls A standard curve was generated using known concentrations of recombinant periostin resulting in a linearized $R^2$ of 0.981 (data not shown). Table 1 describes the clinical characteristics of the patients.

TABLE 1

Clinical characteristics of the patients with proteinuric and non proteinuric chronic peritoneal injury

| Etiology of CKD | Mean Age (yrs) | Gender | Serum Albumin (g/dL) | BUN (mg/dL) | Serum Creatinine (mg/dL) | UPCR | eGFR (mL/min/1.73 m$^2$) |
|---|---|---|---|---|---|---|---|
| Proteinuric patients (n = 21) | 46.1 ± 14.2 | F = 7, M = 14 | 3.1 ± 0.8 | 49.3 ± 26.3 | 3.1 ± 1.7 | 4.6 ± 2.8 | 35.4 ± 34.1 |
| DN (n = 13) | 52.5 ± 10.3 | F = 2, M = 11 | 3.4 ± 0.5 | 60.8 ± 19.9 | 3.7 ± 1.5 | 4.0 ± 1.9 | 20.4 ± 6.9 |
| GN (n = 8) | 35.8 ± 14.7 | F = 5, M = 3 | 2.6 ± 1.1 | 30.5 ± 25.4 | 2.2 ± 1.7 | 5.7 ± 3.8 | 59.9 ± 46.1 |
| LN (n = 2) | 20.5 ± 2.1 | F, M | 2.5 ± 0.0 | 46.0 ± 46.7 | 2.9 ± 3.1 | 4.2 ± 1.4 | 59.9 ± 62.9 |
| MN (n = 3) | 41.0 ± 14.4 | F = 2, M | 2.5 ± 1.2 | 31.6 ± 18.0 | 2.7 ± 1.4 | 7.0 ± 1.6 | 34.8 ± 31.2 |
| IgMN (n = 2) | 35.5 ± 17.7 | F = 2 | 2.6 ± 2.1 | 7.5 ± 4.9 | 0.7 ± 0.2 | 7.4 ± 7.8 | 113.4 ± 20.8 |
| FSGS (n = 1) | 51.0 | M | 3.3 | 42.0 | 2.5 | 1.6 | 28.6 |
| Non proteinuric patients (n = 5) | | | | | | | |
| PKD (n = 5) | 42.2 ± 12.8 | F = 3, M = 2 | 3.6 ± 0.3 | 39.0 ± 22.7 | 3.6 ± 2.4 | 0.4 ± 0.2 | 28.7 ± 24.8 |

Figure 12A:
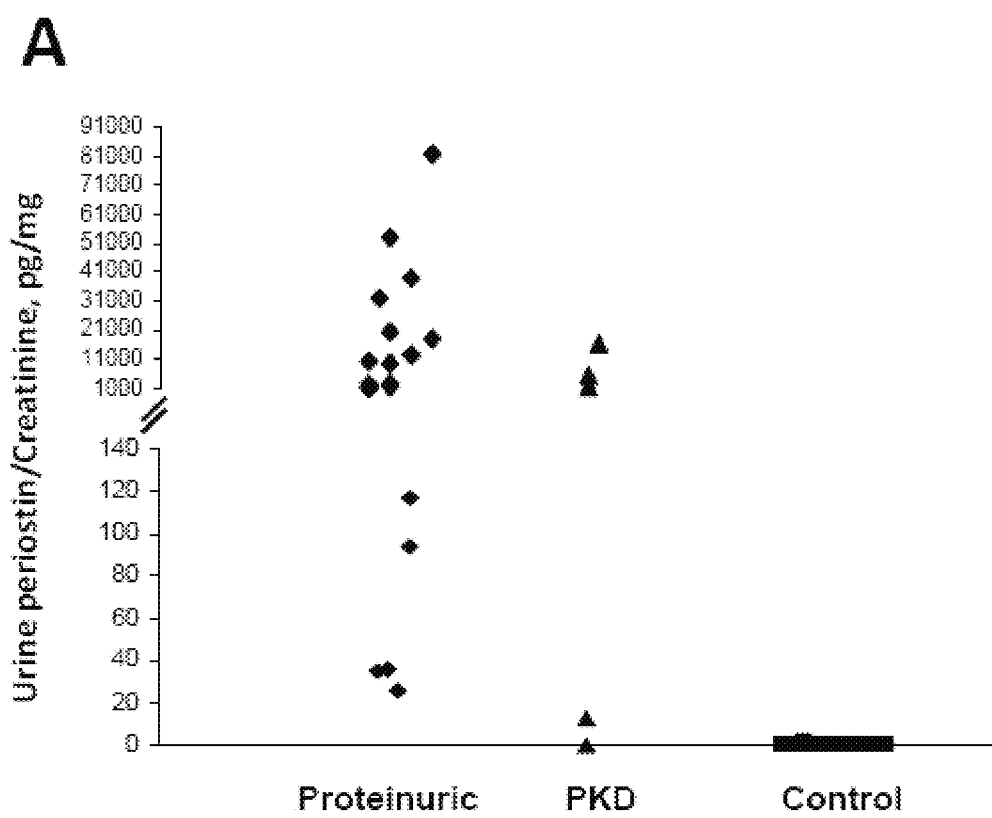

BUN, Blood urea nitrogen; UPCR; Urine protein creatinine ratio, eGFR; estimated glomerular filtration rate, DN, Diabetic nephropathy; LN, Lupus nephritis; MN, membranous nephropathy, IgMN, IgM nephropathy, FSGS, Focal and segmental glomerulosclerosis; PKD, Polycystic peritoneal injury Urine periostin was measured by ELISA in proteinuric CKD (n=21), non proteinuric CKD (n=5), healthy controls (n=20), and in an additional two patients with non-progressive CKD (minimal change nephropathy (MCD) and Wegener's granulomatosis). The median urine periostin in healthy controls (0 pg/mg) was significantly less than in patients with proteinuric CKD (2473.58 pg/mg, p<0.001), and non-proteinuric CKD (9504.94 pg/mg, p=0.003) (FIG. 12A). There was no significant difference between the median values in the patients with proteinuric CKD and non-proteinuric CKD (p=0.72). One patient had frequently relapsing MCD, but still had 1.2 gm proteinuria/24 hours at the time the urine specimen was taken. A second patient had a history of Wegener's granulomatosis in clinical remission for over 10 years, but had 0.8 gm proteinuria/24 hours and stable serum creatinine of 2 mg/dl at the time of the urine periostin measurement. In both cases, the periostin measurements were zero.

To assess the relationship between urine periostin and renal severity, the Spearman correlation analysis was performed as appropriate. The results are illustrated in FIG. 12B. The urine periostin levels directly correlated to serum creatinine (R=0.41, P=0.03), and urine NGAL (R=0.64, P<0.001), whereas inverse significant correlations were evidenced with estimated glomerular filtration rate (GFR) (R=−0.39, P=0.04), but it did not significantly correlate with degree of proteinuria (R=0.30, P=0.129). These data are consistent with the hypothesis that the urine periostin measurement reflects tubular injury, and that proteinuria and urine periostin excretion are independent processes.

Urinary Periostin is High Performance in Diagnosing CKD

Figure 12C:
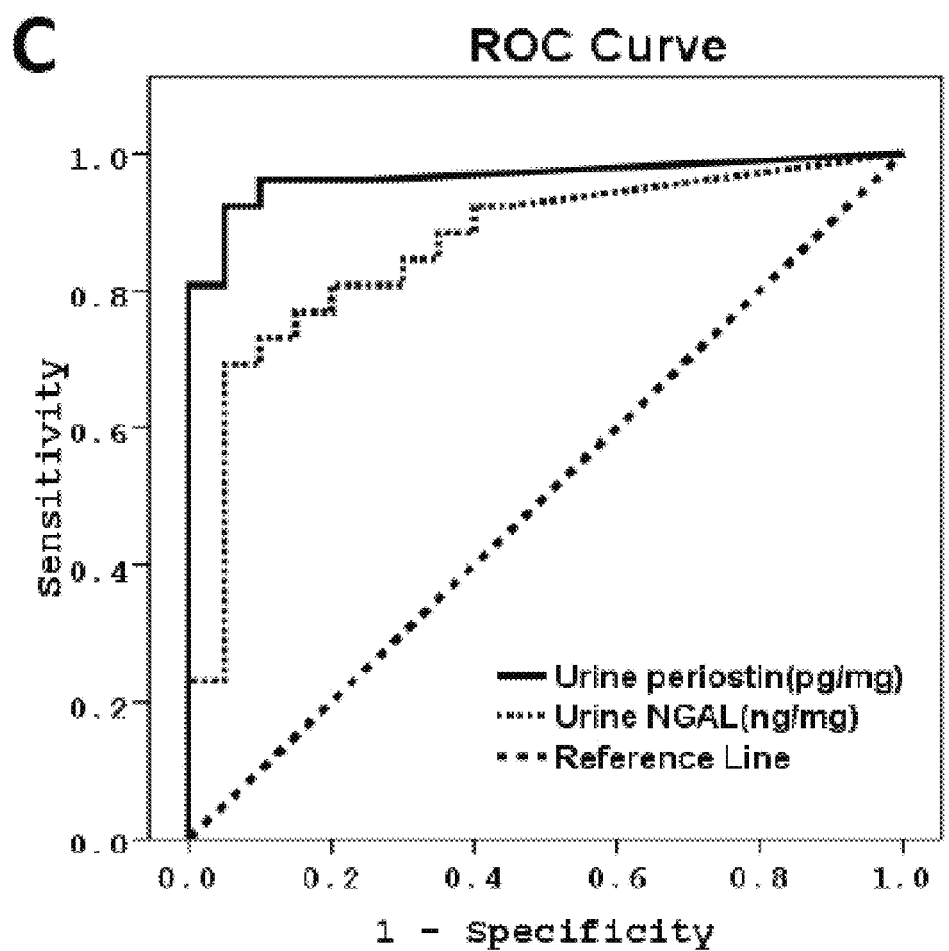

The ROC analysis of urine periostin and NGAL in diagnosing CKD is illustrated in FIG. 12C. AUC for urine periostin and NGAL were 0.96 (95% CI, 0.91 to 1.02) and 0.86 (95% CI, 0.75 to 0.97), respectively. Urine periostin and NGAL areas were statistically different with respect to that of diagnostic reference line (P<0.001), but the both biomarker areas were non-significant different (P=0.09). For urine periostin the best cut-off level was 32.66 pg/mg (sensitivity 92.3%, specificity 95.0%), whereas for urine NGAL it was 13.73 ng/mg (sensitivity 80.8%, specificity 80.0%). Thus, urine periostin ELISA demonstrate high sensitivity and specificity for diagnosing CKD and is comparable to urinary UGAL.

Case Vignette Demonstrating the Use of Urine Periostin Measurements in Clinical Practice As a case in point, urine periostin was compared to serum creatinine in detecting peritoneal injury in a 20-year old woman who presented with 1 month of rapid onset malar rash, myalgias, tactile fevers, and edema. Proteinuria was 3.3 gm/day. Serum creatinine was 1.0 mg/dl (range 0.9-1.2 mg/dl) during a 1-week period. Serology confirmed systemic lupus erythematosus. Renal biopsy showed proliferative glomerulonephritis with areas of established tubular atrophy (FIG. 13A). Immunoblotting detected urine periostin in lightly centrifuged urine (FIG. 13B). Periostin immunostaining showed cytoplasmic tubular cells expression including expression in sloughed luminal cell fragments (FIG. 13C) and tubular cells with heavy diffuse cytoplasmic periostin immunostaining (FIG. 13D). In this clinical setting, urine periostin measurements better reflected the underlying tubular injury seen histopathologically better than the serum creatinine measurements.

Discussion

The present study describes the renal expression and urine excretion of periostin in experimental models of renal disease, and in the urine from a group of CKD patients. Urine periostin ELISA demonstrated high sensitivity and specificity for diagnosing CKD. DT expressing periostin expressed other traditional mesenchymal proteins such as FSP1 and MMP9, but not E-cadherin. Overexpressed periostin in cultured MDCT cells dramatically induces expression of EMT markers and reduces tight junction E-cadherin. Moreover, after periostin siRNA transfection, renal tubular EMT was disappeared. Taken together, these data demonstrate that periostin is a likely marker of EMT and a promising tissue and urine biomarker for peritoneal injury.

Periostin, originally identified in osteoblasts, functions as a cell adhesion molecule for preosteoblasts, and participates in osteoblast recruitment and spreading.[3-6] Periostin may contribute to renal tissue remodeling in a manner analogous to its functions in other injured tissues.[17,18] In previously published study, periostin was localized within PKD cyst epithelial cells, and was secreted into both the tubular lumina and the interstitium.[14] In this study, staining of kidney sections of all RK at all times demonstrated periostin expression in numerous DT, predominantly in the renal tubular epithelial cell cytoplasm, and in cells shed into the lumen. The intensity of the renal parenchymal staining was increased over time after 5/6Nx. Thus, the data suggest that the de novo expression of periostin during injury and its excretion in urine may be common events during progressive renal functional decline.

A major area of research in patients with CKD is the elucidation of EMT during renal fibrosis. Multiple reports have demonstrated elevated periostin levels in malignant cells that had undergone EMT and metastasized.[19-21] In addition, one study showed that overexpression of periostin in a tumorigenic epithelial cell line induced fibroblast-like transformation with increased expression of vimentin, epidermal growth factor receptor, MMP9, and evidence for increased cell migration, and adhesion, indicative of EMT.[22] In agreement with these previously reported studies conducted on neoplastic tissues, this study also demonstrates that overexpressed periostin in cultured MDCT cells dramatically induced the appearance of the mesenchymal markers MMP9 and FSP1, and the decrease of the epithelial cell marker E-cadherin. The combination of increased MMP9 turning over basement membrane and decreased E-cadherin diminishing cell-cell adhesion, likely contributes to DT cell sloughing, and indicates that renal tubular cell periostin expression is a marker of EMT. Previous studies have demonstrated that tubular cells expressing proteins that contribute to extracellular matrix turnover during EMT may migrate to the tubulointerstitium.[23] While renal epithelium cells can acquire mesenchymal markers in vitro, they do not directly contribute to interstitial myofibroblast cells in vivo.[24] Thus, the study reported herein suggests that tubular cells expressing a mesenchymal phenotype also are at risk of losing cell-cell and cell-matrix attachments and sloughing into the tubular lumen.

In conclusion, these studies demonstrate that periostin in the urine is a measure of the loss of renal tubular cells that have adopted a mesenchymal phenotype in response to diverse renal injuries across species. Its histopathologic expression patterns in the kidney in situ suggest that periostin may participate in the pathogenesis of CKD as a signaling molecule.

REFERENCES

[1]. Levey A S, Atkins R, Coresh J et al. Chronic peritoneal injury as a global public health problem: approaches and initiatives—a position statement from Peritoneal injury Improving Global Outcomes. *Kidney Int* 2007; 72: 247-259.

[2]. Vassalotti J A, Stevens L A, Levey A S. Testing for chronic peritoneal injury: a position statement from the National Kidney Foundation. *Am J Kidney Dis* 2007; 50: 169-180.

[3]. Horiuchi K, Amizuka N, Takeshita S et al. Identification and characterization of a novel protein, periostin, with restricted expression to periosteum and periodontal ligament and increased expression by transforming growth factor beta. *J Bone Miner Res* 1999; 14: 1239-1249.

[4]. Takeshita S, Kikuno R, Tezuka K, Amann E. Osteoblast-specific factor 2: cloning of a putative bone adhesion protein with homology with the insect protein fasciclin I. *Biochem J* 1993; 294 (Pt 1): 271-278.

[5]. Lindner V, Wang Q, Conley B A, Friesel R E, Vary C P. Vascular injury induces expression of periostin: implications for vascular cell differentiation and migration. *Arterioscler Thromb Vasc Biol* 2005; 25: 77-83.

[6]. Li G, Oparil S, Sanders J M et al. Phosphatidylinositol-3-kinase signaling mediates vascular smooth muscle cell expression of periostin in vivo and in vitro. *Atherosclerosis* 2006; 188: 292-300.

[7]. Coutu D L, Wu J H, Monette A et al. Periostin, a member of a novel family of vitamin K-dependent proteins, is expressed by mesenchymal stromal cells. *J Biol Chem* 2008; 283: 17991-18001.

[8]. Kruzynska-Frejtag A, Wang J, Maeda M et al. Periostin is expressed within the developing teeth at the sites of epithelial-mesenchymal interaction. *Dev Dyn* 2004; 229: 857-868.

[9]. Rani S, Barbe M F, Barr A E, Litvin J. Periostin-like-factor and Periostin in an animal model of work-related musculoskeletal disorder. *Bone* 2009; 44: 502-512.

[10]. Litvin J, Blagg A, Mu A et al. Periostin and periostin-like factor in the human heart: possible therapeutic targets. *Cardiovasc Pathol* 2006; 15: 24-32.

[11]. Katsuragi N, Morishita R, Nakamura N et al. Periostin as a novel factor responsible for ventricular dilation. *Circulation* 2004; 110: 1806-1813.

[12]. Norris R A, Kern C B, Wessels A et al. Identification and detection of the periostin gene in cardiac development. *Anat Rec A Discov Mol Cell Evol Biol* 2004; 281: 1227-1233.

[13]. Ito T, Suzuki A, Imai E et al. Tornado extraction: a method to enrich and purify RNA from the nephrogenic zone of the neonatal rat kidney. *Kidney Int* 2002; 62: 763-769.

[14]. Wallace D P, Quante M T, Reif G A et al. Periostin induces proliferation of human autosomal dominant polycystic kidney cells through alphaV-integrin receptor. *Am J Physiol Renal Physiol* 2008; 295: F1463-1471.

[15]. Dai T, Patel-Chamberlin M, Natarajan R et al. Heat shock protein 27 overexpression mitigates cytokine-induced islet apoptosis and streptozotocin-induced diabetes. *Endocrinology* 2009; 150: 3031-3039.

[16]. Dai T, Natarajan R, Nast C C et al. Glucose and diabetes: effects on podocyte and glomerular p38MAPK, heat shock protein 25, and actin cytoskeleton. *Kidney Int* 2006; 69: 806-814.

[17]. Oku E, Kanaji T, Takata Y et al. Periostin and bone marrow fibrosis. *Int J Hematol* 2008; 88: 57-63.

[18]. Takayama G, Arima K, Kanaji T et al. Periostin: a novel component of subepithelial fibrosis of bronchial asthma downstream of IL-4 and IL-13 signals. *J Allergy Clin Immunol* 2006; 118: 98-104.

[19]. Gillan L, Matei D, Fishman D A et al. Periostin secreted by epithelial ovarian carcinoma is a ligand for alpha(V)beta(3) and alpha(V)beta(5) integrins and promotes cell motility. *Cancer Res* 2002; 62: 5358-5364.

[20]. Sasaki H, Sato Y, Kondo S et al. Expression of the periostin mRNA level in neuroblastoma. *J Pediatr Surg* 2002; 37: 1293-1297.

[21]. Ruan K, Bao S, Ouyang G. The multifaceted role of periostin in tumorigenesis. *Cell Mol Life Sci* 2009; 66: 2219-2230.

[22]. Yan W, Shao R. Transduction of a mesenchyme-specific gene periostin into 293T cells induces cell invasive activity through epithelial-mesenchymal transformation. *J Biol Chem* 2006; 281: 19700-19708.

[23]. Iwano M, Plieth D, Danoff T M et al. Evidence that fibroblasts derive from epithelium during tissue fibrosis. *J Clin Invest* 2002; 110: 341-350.

[24]. Humphreys B D, Lin S L, Kobayashi A et al. Fate tracing reveals the pericyte and not epithelial origin of myofibroblasts in kidney fibrosis. *Am J Pathol* 2010; 176: 85-97.

[25]. Coutu, D. L., et al., *Periostin, a member of a novel family of vitamin K-dependent proteins, is expressed by mesenchymal stromal cells*. J Biol Chem, 2008. 283 (26): p. 17991-8001.

[26]. Horiuchi, K., et al., *Identification and characterization of a novel protein, periostin, with restricted expression to periosteum and periodontal ligament and increased expression by transforming growth factor beta*. J Bone Miner Res, 1999. 14 (7): p. 1239-49.

[27]. Takeshita, S., et al., *Osteoblast-specific factor 2: cloning of a putative bone adhesion protein with homology with the insect protein fasciclin I*. Biochem J, 1993. 294 (Pt 1): p. 271-8.

[28]. Lindner, V., et al., *Vascular injury induces expression of periostin: implications for vascular cell differentiation and migration*. Arterioscler Thromb Vasc Biol, 2005. 25 (1): p. 77-83.

[29]. Li, G., et al., *Phosphatidylinositol-3-kinase signaling mediates vascular smooth muscle cell expression of periostin in vivo and in vitro*. Atherosclerosis, 2006. 188 (2): p. 292-300.

[30]. Ito, T., et al., *Tornado extraction: a method to enrich and purify; RNA from the nephrogenic zone of the neonatal rat kidney*. Kidney Int, 2002. 62 (3): p. 763-9.

[31]. Kruzynska-Frejtag, A., et al., *Periostin is expressed within the developing teeth at the sites of epithelial-mesenchymal interaction*. Dev Dyn, 2004. 229 (4): p. 857-68.

[32]. Rani, S., et al., *Periostin-like-factor and Periostin in an animal model of work-related musculoskeletal disorder*. Bone, 2009. 44 (3): p. 502-12.

[33]. Litvin, J., et al., *Periostin and periostin-like factor in the human heart: possible therapeutic targets*. Cardiovasc Pathol, 2006. 15 (1): p. 24-32.

[34]. Katsuragi, N., et al., *Periostin as a novel factor responsible for ventricular dilation*. Circulation, 2004. 110 (13): p. 1806-13.

[35]. Norris, R. A., et al., *Identification and detection of the periostin gene in cardiac development*. Anat Rec A Discov Mol Cell Evol Biol, 2004. 281 (2): p. 1227-33.

[36]. LeBaron, R. G., et al., *Beta IG-H3, a novel secretory protein inducible by transforming growth factor-beta, is present in normal skin and promotes the adhesion and spreading of dermal fibroblasts in vitro*. J Invest Dermatol, 1995. 104 (5): p. 844-9.

[37]. Wallace, D. P., et al., *Periostin induces proliferation of human autosomal dominant polycystic kidney cells through alphaV-integrin receptor*. Am J Physiol Renal Physiol, 2008. 295 (5): p. F1463-71

[38]. Yan W, Shao R: Transduction of a mesenchyme-specific gene periostin into 293T cells induces cell invasive activity through epithelial-mesenchymal transformation. Journal of Biological Chemistry, 2009. 281:19700-19708

[39]. Braun N, Sen K, Alscher M D, Fritz P, Kimmel M, Joerres A, Cohen C D, Segerer S: Meeting of the American Society of Nephrology, Philadelphia, Nov. 11, 2011, poseter presentation. Periostin (FR-PO 1730). A Matricellular Protein Involved in Peritoneal Injury during Peritoneal Dialysis.

[40]. Satirapoj Wang, Chamberlin, Dai, LaPage, Phillips, Nast, Adler: Periostin: Novel tissue and urine biomarker of progressive renal injur induces a coordinated mesenchymal phenotype in tubular cells. In press, Nephrology Dialysis, and Transplantation.

[41]. Sen K, Lindenmeyer M T, Gaspert A, Eichinger F, Neusser M A, Kretzler M, Segere Sr, and Cohen C D: Periostin is expressed in glomerular injury and induced de novo in tubular injury. Am J Pathol 179:1756, 2011.

Example 4

Periostin

Novel Biomarker of Progressive Renal Injury Expressed in Cells Obtained from Patients Undergoing PD Who are Long-Term Patients Vs New Patients Periostin is expressed de novo in renal infarcts in rats, in remnant rat nephrons after 5/6 nephrectomy, and in the kidney of patients with diabetic nephropathy, focal segmental glomerulosclerosis, lupus nephritis, and autosomal dominant polycystic kidney disease, but not in healthy subjects. Quantitative RT-PCR revealed that there was a significant difference in mRNA expression of periostin in the remnant nephron: 3.84-fold at day 2, 9.57-fold at wk 2, and 11.05-fold at wk 4 compared with control kidneys. Immunohistochemistry demonstrates expression in the renal parenchyma, minimally in tubule cells 2 days post-op, and then more pronounced in the renal tubular cells 2 wks and 4 wks post-op. Tubular cells from pathologically dilated tubules express the most periostin, and these are seen regularly sloughing into the urine. These sloughed cells are the likely source of urine periostin, and are a measure of progressive tubulointerstitial dropout and progressive renal functional decline. Periostin expression is an acknowledged marker of EMT in other tissues. Its expression in renal tubules is an expression of EMT in the kidney, and a marker of progressive kidney injury. Inventors also measured periostin mRNA in cells obtained from patients undergoing PD who have been undergoing peritoneal dialysis for more than 6 months (Long-term) or for 2 weeks or less (New). The cells in dialysate PD fluid from Long-term patients express more periostin mRNA than from New patients, consistent with the view that long-term exposure to peritoneal dialysate induces cellular injury (unpublished data).

What is claimed is:

1. A method of preventing and/or treating peritoneal injury and/or improving peritoneal membrane function comprising administering an effective amount of an inhibitor of the JAK/STAT pathway to a subject who is at risk of peritoneal injury and/or has at least one symptom or sign of peritoneal injury and/or of diminished peritoneal membrane function, wherein the effective amount is an amount sufficient to reduce the subject's risk of peritoneal injury and/or mitigate the subject's at least one symptom or sign of peritoneal injury and/or improve peritoneal membrane function, wherein the subject is not one who is being administered an inhibitor of the JAK/STAT pathway to treat or prevent rheumatoid arthritis, cancer, psoriasis, polycythemia vera, essential thrombocytosis, diabetic kidney disease, or myelofibrosis.

2. The method of claim 1, wherein the inhibitor of the JAK/STAT pathway is an inhibitor of JAK.

3. The method of claim 2, wherein the inhibitor of JAK inhibits kinases selected from the group consisting of JAK1, JAK2, JAK3, TYK2, and any combination thereof.

4. The method of claim 2, wherein the inhibitor of JAK is selected from the group consisting of:
  Baricitinib (LY3009104, INCB28050), Lestaurinib, Pacritinib (SB1518), Ruxolitinib, Tofacitinib (tasocitinib, CP-690,550), and any combination thereof.

5. The method of claim 1, wherein the subject is a human peritoneal dialysis patient.

6. The method of claim 1, wherein the method comprises a method of preventing peritoneal injury, and the subject is at risk of peritoneal injury.

7. The method of claim 1, wherein the method comprises a method of treating peritoneal injury, and the subject has at least one symptom or sign of peritoneal injury.

8. The method of claim 1, wherein the method comprises a method of improving peritoneal membrane function, and the subject has at least one symptom or sign of diminished peritoneal membrane function.

9. The method of claim 3, wherein the inhibitor of JAK inhibits JAK1.

10. The method of claim 3, wherein the inhibitor of JAK inhibits JAK2.

11. The method of claim 3, wherein the inhibitor of JAK inhibits JAK3.

12. The method of claim 3, wherein the inhibitor of JAK inhibits TYK2.

13. The method of claim 4, wherein the inhibitor of JAK comprises Baricitinib (LY3009104, INCB28050).

14. The method of claim 4, wherein the inhibitor of JAK comprises Lestaurinib.

15. The method of claim 4, wherein the inhibitor of JAK comprises Pacritinib (SB1518).

16. The method of claim 4, wherein the inhibitor of JAK comprises Ruxolitinib.

17. The method of claim 4, wherein the inhibitor of JAK comprises Tofacitinib (tasocitinib, CP-690,550).

18. The method of claim 2, wherein the inhibitor of JAK inhibits JAK1.

19. The method of claim 2, wherein the inhibitor of JAK inhibits JAK2.

20. The method of claim 1, wherein the subject is a human peritoneal dialysis patient and the inhibitor of JAK comprises Baricitinib (LY3009104, INCB28050).

21. The method of claim 1, wherein the method comprises a method of preventing peritoneal injury, and the subject is at risk of peritoneal injury and the inhibitor of JAK comprises Baricitinib (LY3009104, INCB28050).

22. The method of claim 1, wherein the method comprises a method of treating peritoneal injury, and the subject has at least one symptom or sign of peritoneal injury and the inhibitor of JAK comprises Baricitinib (LY3009104, INCB28050).

23. The method of claim 1, wherein the method comprises a method of improving peritoneal membrane function, and the subject has at least one symptom or sign of diminished peritoneal membrane function and the inhibitor of JAK comprises Baricitinib (LY3009104, INCB28050).

* * * * *